United States Patent
Bouillé et al.

(10) Patent No.: US 9,567,634 B2
(45) Date of Patent: Feb. 14, 2017

(54) METHOD FOR DETECTING OR MEASURING THE IMPACT OF A VIRAL VECTOR COMPOSITION ON EUKARYOTIC CELLS AND BIOMARKERS USED THEREOF

(71) Applicant: VECTALYS, Toulouse (FR)

(72) Inventors: Pascale Bouillé, Escalquens (FR); Régis Gayon, Ramonville Saint Agne (FR); Alexandra Iché, Corronsac (FR)

(73) Assignee: VECTALYS, Toulouse (FR)

( * ) Notice: Subject to any disclaimer, the term of this patent is extended or adjusted under 35 U.S.C. 154(b) by 0 days.

(21) Appl. No.: 14/417,332

(22) PCT Filed: Jul. 26, 2013

(86) PCT No.: PCT/IB2013/002085
§ 371 (c)(1),
(2) Date: Jan. 26, 2015

(87) PCT Pub. No.: WO2014/016690
PCT Pub. Date: Jan. 30, 2014

(65) Prior Publication Data
US 2015/0197803 A1    Jul. 16, 2015

Related U.S. Application Data

(60) Provisional application No. 61/676,098, filed on Jul. 26, 2012.

(51) Int. Cl.
*C12Q 1/68*    (2006.01)

(52) U.S. Cl.
CPC ....... *C12Q 1/6876* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

2007/0270455 A1*   11/2007   Gudkov ............... A61K 31/473
                                                              514/297

OTHER PUBLICATIONS

Kasamatsu A. et al.,"Identification of candidate genes associated with salivary adenoid cystic carcinomas using combined comparative genomic hybridization and oligonucleotide microarray analyses" International Journal of Biochemistry and Cell Biology, pp. 1869-1880, vol. 37, No. 9 (Sep. 2005).

"Affymetrix Human Genome U133 Plus 2.0 Array comprises probes for CXCL2" URL:http://www.affymetrix.com;estore;analysis/index.affx?category=34005&categoryidClicked=34005&rootCategoryid=34005&navMode=34005&aid=netAffxNav> (Jan. 2005).

Affymetrix Human Genome U133 Plus 2.0 Array comprises probes for EREG URL:http://www.affymetrix.com;estore;analysis/index.affx?category=34005&categoryidCicked=34005&rootCategoryid=34005&navMode=34005&aid=netAffxNav> (Jan. 2005).

Jitao Zhang et al., "qPCR Identification of Genes Involved in Apoptosis and Cell Cycle Regulation" Biochemica, pp. 21-24, vol. 2 (Jan. 2009).

Heiko et al., "RealTime ready qPCR Assay Design and Configuration Portal Content", URL:http:ffwww.roche-applied-science.com;wcsstore/RASCatalogAssetStore/Articles/RTRWhitepaper 03.11.pdf, (Mar. 2011).

M Dietrich et al., "RealTime ready RT-qPCR Assay Development and Qualification", URL:http:ffwww.roche-applied-science.com;wcsstore/RASCatalogAssetStore/Articles/RTR04.11.pdf, (Mar. 2011).

V Baekelandt et al., "Optimized lentiviral vector production and purification procedure prevents immune response after transduction of mouse brain Laboratory for Experimental" Gene Therapy, pp. 1933-1940, vol. 10 (Jan. 2003).

Rodrigues T et al., "Scaleable purification process for gene therapy retroviral vectors" Journal of Gene Medicine, pp. 233-243, vol. 9, No. 4, (Apr. 2007).

Rodrigues T et al.,"Purification of retroviral vectors for clinical application: Biological implications and technological challenges", Journal of Biotechnology, pp. 520-541, vol. 127, No. 3 (Dec. 2006).

Y Zhao et al., "Comparative studies on cellular gene regulation by HIV-1 based vectors: implications for quality control of vector production" Gene Therapy, pp. 311-319, vol. 12, No. 4 (Nov. 2004).

Zhao et al., "Comparison of toxicogenomic profiles of two murine strains treatedwith HIV-1-based vectors for gene therapy", Toxicology and Applied Pharmacology, pp. 189-197, vol. 225, No. 2 (Nov. 2007).

Agilent Whole Human Genome Oligo Microarray Kit with SurePrint Technology, Catalog 60-mer Oligo, Agilent Technologies (2004).

* cited by examiner

*Primary Examiner* — Catherine S Hibbert
(74) *Attorney, Agent, or Firm* — Browdy and Neimark, PLLC

(57) ABSTRACT

The present invention relates to methods and compositions for characterization of global cellular changes in response to introduction of viral vector compositions into target cells. It more particularly refers to a method for assessing the quality of a viral vector composition for a transgene transfer into target cells comprising measuring the expression level of at least one biomarker selected in the group consisting of CXCL2 and EREG and/or of at least one biomarker selected in the group consisting of ASPM, AURKB, CENPA, CENPF, CKS1B, E2F8, ERCC6L, FAM83D, KIFC1, MKI67, NEK2, NUSAP1, OIP5, PRC1, RRM2, SGOL1, SPC25, TOP2A and TTK.

9 Claims, 23 Drawing Sheets

FIG. 1C

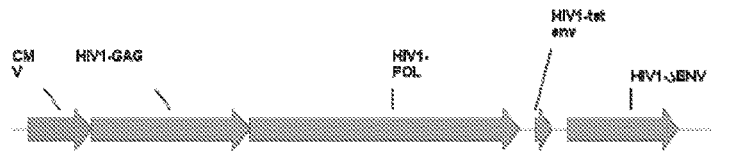

pGag Pol

Plasmid harboring gag and pol genes

Figure 1A:
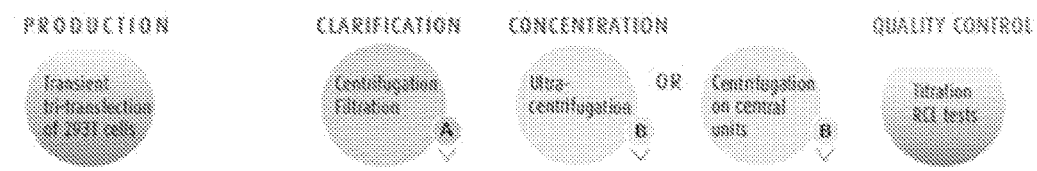

| FEATURES | Length (bp) | |
|---|---|---|
| promoter | 602 | /label=CMV |
| CDS | 1502 | /label=HIV1_gag |
| CDS | 2737 | /label=HIV1-pol |
| CDS | 1173 | /label=HIV1-env deleted |
| protein_bind | 204 | /label=HIV1_RRE |

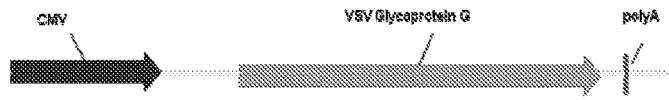

pEnv

Envelope expressing helper plasmid

| FEATURES | Length (bp) | |
|---|---|---|
| Promoter | 677 | /label=CMV |
| CDS | 1642 | /label=VSV_glycoprotein\_G |
| polyA_signal | 768 | /label=HBB2 |

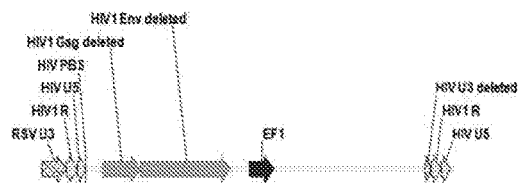

pLVEF1

Transgene expression plasmid without cDNA

| FEATURES | Length (bp) | |
|---|---|---|
| repeat_region | 230 | /label=RSV_U3 |
| Feature | 119 | /label= packaging signal |
| CDS | 362 | /label=HIV1_gag_deleted |
| Promoter | 236 | /label=EF1_promoter |
| Feature | 18 | /label=Primer Binding Site PBS |
| repeat_unit | 55 | /label=HIV_U3 deleted |
| repeat_unit | 95 | /label=HIV_R |
| repeat_unit | 85 | /label=HIV_U5 |

| | Titer (TU/mL) (1) | PP/TU (2) |
|---|---|---|
| rLV-EF1 batch B | 4.7E+08 | 104 |
| rLV-EF1 batch C | 8.9E+09 | 67 |

FIG. 2A

Selection of Fold Change ≥1,5

Selection of Fold Change ≥1,5

Downregulated probes in cells transduced
with batch B at MOI150
versus non-transduced cells.

Downregulated probes in cells transduced
with batch C at MOI150
versus non-transduced cells

FIG. 6B

| Gene (1) | Batch (2) | RT-qPCR FC versus NT (3) | Microarray FC versus NT (4) |
|---|---|---|---|
| AURKB | MOI 150 batch C | -7,5 | -5,2 |
| | MOI 150 batch B | -17,4 | -10,1 |
| NEK2 | MOI 150 batch C | -8,0 | -5,8 |
| | MOI 150 batch B | -16,8 | -10,4 |
| E2F8 | MOI 150 batch C | -9,8 | -12,1 |
| | MOI 150 batch B | -25,9 | -19,6 |
| MKI67 | MOI 150 batch C | -8,3 | -5,6 |
| | MOI 150 batch B | -17,4 | -8,6 |
| CENPA | MOI 150 batch C | -7,9 | -6,2 |
| | MOI 150 batch B | -17,7 | -11,5 |

Modulated probes in cells transduced
with batch B-S at MOI150
versus non-transduced cells.
FC≥1.5

Modulated probes in cells transduced
with batch C at MOI40
versus non-transduced cells.
FC≥1.5

| rLV-EF1-GFP Batch | Titer (TU/ml) (1) | PP/TU (2) |
|---|---|---|
| C | 7,57E+07 | 195 |
| B | 9,26E+07 | 361 |
| B-S | 2,48E+08 | 293 |
| UC | 1,12E+08 | 348 |

MOI 40

MOI 150

| | p-value (t-test) cells vs. cells transduced with batch C on ΔΔCt |
|---|---|
| NT | 0,00 |
| B MOI 40 | 0,00 |
| B-S MOI 40 | 0,05 |
| UC MOI 40 | 0,00 |

|  | p-value (t-test) cells vs. cells transduced with batch C on ΔΔCt | p-value (t-test) cells transduced vs. non-transduced cells on ΔΔCt |
|---|---|---|
| NT | 0,00 |  |
| B MOI 40 | 0,00 | 0,00 |
| B-S MOI 40 | 0,95 | 0,00 |
| UC MOI 40 | 0,00 | 0,00 |
| C MOI 40 |  | 0,00 |

|  | p-value (t-test) cells vs. cells transduced with batch C on ΔΔCt | p-value (t-test) cells transduced vs. non-transduced cells on ΔΔCt |
|---|---|---|
| NT | 0,01 |  |
| B MOI 150 | 0,00 | 0,00 |
| B-S MOI 150 | 0,00 | 0,00 |
| UC MOI 150 | 0,00 | 0,00 |
| C MOI 150 |  |  |

METHOD FOR DETECTING OR MEASURING THE IMPACT OF A VIRAL VECTOR COMPOSITION ON EUKARYOTIC CELLS AND BIOMARKERS USED THEREOF

The invention relates generally to the field of viral vector mediated gene therapy and recombinant gene expression. More particularly, the present invention relates to methods and compositions that utilize a particular panel of gene products ("biomarkers") and their differential expression patterns ("expression signatures"), wherein the expression patterns correlate with the impact a viral vector composition may have on any given target cell, in particular on any given eukaryotic cell. The invention is based on the identification of a specific set of biomarkers that are differentially expressed in viral vector transduced cells and which are useful in predicting the quality, i.e., purity and/or concentration, of a viral vector composition. The gene panel is also useful in designing specific adjuvant modalities with improved therapeutic efficiency.

Virus-based vectors are a tool commonly used to deliver genetic material into cells. Such vectors were originally developed as an alternative to transfection of naked DNA for molecular genetics experiments and for therapeutic uses such as gene therapy or vaccines. Viral vectors fall into two main categories: integrating vectors, which insert themselves into the recipient genome and non-integrating vectors, which usually form an extra chromosomal genetic element. Integrating vectors such as gamma-retroviral vectors (RV) and lentiviral vectors (LV) are stably inherited. Non-integrating vectors, such as adenoviral vectors (ADV) and adeno-associated virus (AAV) vectors are quickly lost from cells that divide rapidly.

In particular, retroviral vectors are derived from viruses belonging to the Retroviridiae family that comprises enveloped RNA viruses with a complex macromolecular structure having an hydrodynamic diameter of approximately 150 nm (Salmeen et al. 1975). Due to the large size the viral particles have low diffusivity (10-8 $cm^2$/s); their density is about 1.15-1.16 g/cm3 as determined by sucrose gradient ultra-centrifugation (Coffin et al. 1997). They are composed by 60-70% protein, 30-40% lipid (derived from the plasma membrane of the producer cells), 2-4% carbohydrate and 1% RNA (Andreadis et al. 1999). Retroviral particles consist of two identical copies of single-stranded positive sense RNA, plus integrase and reverse transcriptase enzymes, contained within a protein capsid surrounded by a lipid bilayer membrane. The lipid bilayer is studded with glycoprotein projections. Retroviral vectors are negatively charged particles in a broad pH range since their isoelectric point occurs at very low pH values. The envelope proteins and the lipid bilayer are probably the main contributors to the negative charge at the virus surface (Rimai et al. 1975).

The use of virus-based vectors has become a crucial delivery method for in vitro applications in drug discovery, for in vivo and ex vivo clinical assays, for gene therapy and animal model development. The lentiviral vectors, such as HIV-derived vectors, are currently the preferred tools for gene transfer, both in vitro and in vivo, due to their capacity to transduce immortalized cells or primary cells, both quiescent or proliferating cells, and to the resulting stable integration of the transgene in the genome. These advantages make them not only a valuable tool in both the therapeutic context, as well as in functional genomics, but also for the production of molecules of interest for human use. The benefit of such vectors for their use in gene therapy has been confirmed by the recent success obtained in the treatment of Adrenoleukodystrophy (N. Cartier, S. Hacein-Bey-Abina, et al. 2009) or human β-thalassaemia (Marina Cavazzana-Calvo et al. 2010).

Current research in regenerative medicine also uses virus-based vectors, especially for the production and differentiation of induced pluripotent stem cells (iPS) (Sommer et al. 2009). Although it is possible to reprogram somatic cells into iPS using crude vector compositions (Takahashi K. and Yamanaka S. 2006), the use of purified and concentrated vector compositions for reprogramming leads to a greater increase in yields and in clonal survival and quality (Vallier et al. 2009). Moreover, virus-based vectors are commonly used to generate cellular models as a part of the validation of therapeutic targets for drug discovery and production of recombinant proteins for therapeutic purposes. In this context, it is essential to finely characterize the changes induced in the transduced cells by the viral-based vectors. As demonstrated by Banito A et al. (2009), cell manipulation like cell reprogramming may be slow and stochastic, suggesting the existence of barriers limiting its efficiency or stability. Here they identify senescence as one such barrier and show that ablation of different senescence effectors improves the efficiency of reprogramming. To that end, purified vectors allow one to avoid any negative impact of the viral-based vector compositions on target cells.

The cellular responses generated following infection with HIV have been extensively studied, including the transcriptional changes caused by the virus in immune cells (Giri et al. 2006). In contrast, there are few studies on transcriptional changes caused by HIV-derived lentiviral vectors. The studies to date have focused on the impact of certain stages of transduction, such as integration into the genome of the transduced cell. Some studies, i.e Zhao et al. 2004 and Mitchell et al. 2003, have characterized the global changes in expression profile induced in response to a lentiviral vector. However, all of these studies focus on specific conditions (transgene specific cell type) that do not allow one to draw a general conclusion. Particularly, no study has been conducted on the global impact and toxicity of viral vectors such as lentiviral vectors and the consequences of production process parameters, such as concentration and purification of viral vector composition, on the transcription profile of the transduced cells.

Factors influencing the choice of a particular vector include its packaging capacity, its host range, its gene expression profile, its transduction efficiency and its capacity to elicit immune responses, which is particularly problematic if repeated administrations or transductions are needed. Some of these parameters can be adjusted or controlled. One parameter or particular importance is the use of highly concentrated and highly purified vectors that allow for efficient cell transduction and avoidance of specific cell responses due to impurities in the viral vector compositions. Development of gene therapy, in vivo and ex vivo clinical assays, and drug discovery applications, highlight the need to have tools to measure or detect the effect of a viral vector composition on eukaryotic cells and also to increase the safety associated with the production of proteins for human uses through the use of such viral vectors.

Until now, the question of the toxicity associated with the use of viral vector compositions has not been globally explored nor solved. The present invention is related to the characterization and selection of transcriptional signatures, referred as biomarkers, related to potential deleterious effects in cells upon transduction by viral vector compositions. The present invention discloses assays designed to characterize the safety and quality of viral vector compositions obtained by any process as well as of genetically modified cells transduced by such viral vector compositions. The identification and modulation of genes influencing or interfering with transduction efficiency, which could affect the level of transgene expression, may be targeted to optimize the transduction process.

The present invention provides methods and compositions for characterization of global cellular changes in response to introduction of viral vector compositions into target cells and in particular into eukaryotic cells. Such global changes may be induced by the viral vector itself or may result from the environment in which the viral vector is found such as the level of purity or concentration of the viral vector compositions. As described in detail below, the methods and compositions of the invention utilize a particular panel of gene products ("biomarkers") and their differential expression patterns ("expression signatures"), wherein the expression patterns correlate with the quality of the viral vector composition impact on any given transduced eukaryotic cells.

The present invention provides a method to measure or detect the effect of a viral vector composition on eukaryotic cells by detecting modified gene expression profiles and by screening for modifications in the expression level of at least one biomarker in said cultured cells.

The present invention relates to methods and compositions that utilize a particular panel of biomarkers and their expression signatures, wherein the expression signatures correlate with the effect that a viral vector composition may have on any given target cell, in particular eukaryotic cell. The invention is based on the identification of a specific set of biomarkers that are differentially expressed in viral vector transduced eukaryotic cells and which are useful in predicting the quality of the viral vector composition. Accordingly, the present invention provides methods of predicting the cellular response in cells transduced with a viral vector composition. Specifically, a method is provided for detecting a cellular response in target cells, in particular eukaryotic cells contacted with a viral vector composition comprising (i) measuring the expression level of one or more biomarkers in a eukaryotic cell that has not been contacted with a viral vector composition; (ii) measuring the expression level of one or more biomarkers in a eukaryotic cell following contact with a viral vector composition; and (iii) comparing the biomarker(s) expression in (i) to the biomarker(s) expression in (ii) wherein a change in biomarker expression level between (i) and (ii) indicates a cellular response and wherein said cellular response is correlated to the quality of the viral vector composition. In step (iii) the change in expression may be either an increase or decrease in biomarker expression. In a specific embodiment of the invention, the change in biomarker expression level between (i) and (ii) is established at a minimal absolute value of 1.3 FC (fold change ≥1.3) in expression, either a 1.3 fold increase in expression or a 1.3 decrease in expression. The FC value is correlated to the quality (concentration/purification) of the viral vector composition and to the conditions of transduction, in particular to the MOI.

The identified correlation between biomarker expression and viral vector transduction provides a method for determining the quality of the viral vector composition. The methods of the invention rely on measurement of the expression level of one or more predictive RNA transcripts or their expression products in a transduced cell wherein the predictive RNA transcript or their product is the transcript or product of one or more genes selected from the group consisting of the genes of Tables 2, 3, 4, 5, 6, 7 or 8.

In an embodiment of the present invention, the impact of a viral vector composition on target cells, in particular eukaryotic cells transduced with a viral vector composition is evaluated. In a specific embodiment of the present invention, the cultured cells are transduced by lentiviral vectors. In another embodiment of the invention, the eukaryotic cells are immortalized, primary or stem cells.

In one embodiment of the present invention, the expression level of a biomarker involved in senescence biological processes is measured. In a preferred embodiment, the biomarker involved in senescence is a SASP family member. In a more preferred embodiment, the senescence gene is one or more genes selected from Table 7.

In another embodiment of the present invention, the expression level of a biomarker involved in cell cycle is measured. In a preferred embodiment, the cell cycle biomarker is one or more genes selected from Table 2, Table 3, and Table 4.

In another embodiment of the present invention, the expression level of a biomarker selected from Table 8 is measured.

In another embodiment of the present invention, the invention further provides a method for assessing the quality of a viral vector composition for a transgene transfer into target cells comprising measuring the expression level of at least one biomarker selected in the group consisting of CXCL2 and EREG and/or of at least one biomarker selected in the group consisting of ASPM, AURKB, CENPA, CENPF, CKS1B, E2F8, ERCC6L, FAM83D, KIFC1, MKI67, NEK2, NUSAP1, OIP5, PRC1, RRM2, SGOL1, SPC25, TOP2A and TTK.

In a particular embodiment, the present invention provides a method for assessing the quality of a viral vector composition for a transgene transfer into target cells comprising:

(a) measuring the expression level of at least one biomarker selected in the group consisting of CXCL2 and EREG in target cells that has not been contacted with the viral vector composition;

(b) measuring the expression level of said at least one biomarker in target cells following contact with said viral vector composition; and (c) comparing said biomarker(s) expression in (b) to the biomarker(s) expression in (a) wherein an significant upregulation in biomarker expression level in (b) compared to (a) indicates that the quality of the viral vector composition is insufficient.

More particularly, a significant upregulation at high MOI is a two fold upregulation compared to (a).

The method according to the present invention can further comprise a step of:

(d) measuring the expression level of at least one biomarker selected in the group consisting of ASPM, AURKB, CENPA, CENPF, CKS1B, E2F8, ERCC6L, FAM83D, KIFC1, MKI67, NEK2, NUSAP1, OIP5, PRC1, RRM2, SGOL1, SPC25, TOP2A and TTK in target cells that has not been contacted with the viral vector composition;

(e) measuring the expression level of said at least one biomarker in target cells following contact with said viral vector composition; and (f) comparing said biomarker(s) expression in (e) to the biomarker(s) expression in (d) wherein an significant downregulation in biomarker expression level in (e) compared to (d) indicates that the quality of the viral vector composition is insufficient.

More particularly, a significant downregulation at optimal MOI is a 1.5 fold downregulation compared to (d).

It should be noted that alternatively, steps (d), (e), (f) can be performed before or simultaneously with step (a), (b) and (c).

The method according to the present invention can further comprise a step of:

(g) measuring the expression level of at least one biomarker selected in the group consisting of CXCL2 and EREG in target cells following contact with a control viral vector composition; and (h) comparing said biomarker(s) expression in (g) to the biomarker(s) expression in (a), wherein no significant differential expression in biomarker(s) has to be detected in (g) compared to (a).

The method according to the present invention can further comprise a step of:

(j) measuring the expression level of at least one biomarker selected in the group consisting of ASPM, AURKB, CENPA, CENPF, CKS1B, E2F8, ERCC6L, FAM83D, KIFC1, MKI67, NEK2, NUSAP1, OIP5, PRC1, RRM2, SGOL1, SPC25, TOP2A and TTK in target cells following contact with a control viral vector composition; and (k) comparing said biomarker(s) expression in (j) to the biomarker(s) expression in (d) wherein a potential downregulation in biomarker expression level in (j) compared to (d) has to be detected.

More particularly, the potential downregulation in biomarker expression level in (j) compared to (d) is at least 1.5 times less than the downregulation in biomarker expression level in (e) compared to (d) at high MOI.

The method according to the present invention can further comprise beforehand a step of titration of the viral vector composition and the control viral vector composition.

Advantageously, in the method for assessing the quality of a viral vector composition for a transgene transfer into target cells, the measures of the biomarker expression level are performed before the cells reach confluency.

Preferably, the target cells are eukaryotic cells and are transduced by a lentiviral vector composition.

The invention also provides kits for measuring the level of biomarker expression in a sample of transduced cells. The kits may include one or more reagents corresponding to the biomarkers described herein, e.g., antibodies that specifically bind the biomarkers, recombinant proteins that bind biomarker specific antibodies, nucleic acid probes or primers that hybridize to the biomarkers, etc. In some embodiments, the kits may include a plurality of reagents, e.g., on an array, corresponding to the biomarkers described herein. The kits may include detection reagents, e.g., reagents that are detectably labeled. The kits may include written instructions for use of the kit in predicting the quality of a viral vector composition, and may include other reagents and information such as control or reference standards, wash solutions, analysis software, etc.

In a preferred embodiment, the kit comprises one or more reagents able to measure the expression level of at least one biomarker selected in the group consisting of CXCL2 and EREG.

Advantageously, said kit further comprises one or more reagents able to measure the expression level of at least one biomarker selected in the group consisting of ASPM, AURKB, CENPA, CENPF, CKS1B, E2F8, ERCC6L, FAM83D, KIFC1, MKI67, NEK2, NUSAP1, OIP5, PRC1, RRM2, SGOL1, SPC25, TOP2A and TTK.

Preferably, said kit can also further comprise a control viral vector composition.

The present invention further provides a biochip consisting of at least a biomarker selected in the group consisting of CXCL2 and EREG and at least one biomarker selected in the group consisting of ASPM, AURKB, CENPA, CENPF, CKS1B, E2F8, ERCC6L, FAM83D, KIFC1, MKI67, NEK2, NUSAP1, OIP5, PRC1, RRM2, SGOL1, SPC25, TOP2A and TTK with optionally a ubiquitous gene.

The present invention still further provides a RT-qPCR plate comprising primers of at least a biomarker selected in the group consisting of CXCL2 and EREG and primers of at least one biomarker selected in the group consisting of ASPM, AURKB, CENPA, CENPF, CKS1B, E2F8, ERCC6L, FAM83D, KIFC1, MKI67, NEK2, NUSAP1, OIP5, PRC1, RRM2, SGOL1, SPC25, TOP2A and TTK.

The present invention further relates to a biomarker composition useful for the measurement or detection of the effect of a viral vector composition on eukaryotic cells in order to determine the quality of such compositions. In a preferred embodiment of the present invention, the biomarker composition useful for the measurement or detection of the effect of a viral vector composition on eukaryotic cells comprises at least one of the products selected among the genes or the polypeptides present in Tables 2, 3, 4, 5, 6, 7 and 8. In a more preferred embodiment, the biomarker composition comprises at least one of the products selected among the genes or the polypeptides present in Tables 3, 4, 7 and 8.

DETAILED DESCRIPTION OF THE INVENTION

The present invention provides a specific set of biomarkers that are differentially expressed in viral vector transduced cells. Such biomarkers, as described in detail below, may be used in methods designed to predict the quality of viral vector compositions.

In the present application, terms are employed with their usual meaning, except when precised otherwise.

DEFINITIONS

The term 'viral vector composition' refers to any viral derived composition obtained from, but not limited to, retrovirus, lentivirus, adenoviral, adeno-associated virus and all compositions containing viral vectors thereof. In a preferred embodiment of the invention, the viral vector compositions are based on viruses belonging to the Retroviridiae family that comprises enveloped RNA viruses including, for example, lentiviral (LV) and gamma-retroviral (RV) vectors. Viral vector compositions can be produced using any of the methods known to those of skill in the art. In a specific embodiment of the invention, viral vector compositions to be tested using the methods of the present invention may be obtained by processes such as those described in FIGS. 1A, 1B and 1C.

The term 'measuring or detecting the impact of a viral vector composition' means evaluating the expression of a biomarker following contact of a target cell or a eukaryotic cell with a viral vector composition.

The terms 'biomarker' or 'biological marker' mean an indicator of a biological state. It is a characteristic that is objectively measured and evaluated as an indicator of normal biological processes, pathogenic processes, or pharmacologic responses to a therapeutic intervention. As used herein a "biomarker" is a molecular indicator of a specific biological property and as used herein is a nucleic acid molecule (e.g., a gene or gene fragment) or an expression product thereof (e.g., a RNA, microRNA, a polypeptide or peptide fragment or variant thereof) whose differential expression (presence, absence, over-expression or under-expression relative to a reference) within a cell predicts the quality of a viral vector composition. An "expression product" as used herein is a transcribed sense or antisense RNA molecule (e.g., an mRNA), or a translated polypeptide corresponding to or derived from a polynucleotide sequence. A "panel" of biomarkers is a selection of two or more combinations of biomarkers.

Biomarkers for characterizing a viral vector composition, according to the invention, include those listed in Tables 2, 3, 4, 6, 7 and 8. Such markers include genes that are found to be regulated by transduction of viral vector compositions into a cell. One or more of these biomarkers, or up to all of the biomarkers, may be used together in any combination in the methods according to the invention.

The terms 'nucleic acid' or "polynucleotide" are intended to include DNA molecules such as cDNA or genomic DNA, and RNA molecules, such as mRNA or any fragment of DNA or RNA of interest. These terms refers to deoxyribonucleotides or ribonucleotides and polymers thereof in either single- or double-stranded form including, for example, genomic DNA, cDNA, and mRNA. This term encompasses nucleic acid molecules of both natural and synthetic origin as well as molecules of linear, circular, or branched configuration representing either the sense or antisense strand, or both, of a native nucleic acid molecule. It is understood that such nucleic acids can be unpurified, purified, or attached, for example, to a synthetic material such as a bead or column matrix. The term also encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), polymorphisms, alleles, and complementary sequences as well as the sequence explicitly indicated. The term nucleic acid is used interchangeably with gene, cDNA, and mRNA encoded by a gene or a fragment thereof which is selected as functionally equivalent to the complete molecule.

Accordingly, the present invention provides compositions comprising biomarkers, e.g., nucleic acid molecules and expression products thereof, or means for detecting said biomarkers, wherein the biomarkers are found to be differentially expressed in viral vector transduced cells as compared to non-transduced cells.

Nucleic acid sequences encoding the biomarkers of the invention, are publicly available (for example, accessible in Genbank), known to those of skill in the art, and incorporated herein in their entirety. As described in detail below, such nucleic acid sequences may be used to design probes or primers for use in assays for measuring the levels of biomarker expression in a transduced cell.

Biomarkers according to the invention include substantially identical homologues and variants of the nucleic acid molecules and expression products thereof described herein, for example, a molecule that includes nucleotide sequences encoding polypeptides functionally equivalent to the biomarkers of the invention, e.g, sequences having one or more nucleotide substitutions, additions, or deletions, such as allelic variants or splice variants or species variants or molecules differing from the nucleic acid molecules and polypeptides referred to in the Tables 2, 3, 4, 6, 7, or 8 herein due to the degeneracy of the genetic code.

Other nucleic acids for use in the practice of the invention include those that have sufficient homology to those described herein to detect expression by use of hybridization techniques. Such polynucleotides preferably have about or 95%, about or 96%, about or 97%, about or 98%, or about or 99% identity with the biomarker sequences as described herein. The other polynucleotides for use in the practice of the invention may also be described on the basis of the ability to hybridize to polynucleotides of the invention under stringent conditions of about 30% v/v to about 50% formamide and from about 0.01M to about 0.15M salt for hybridization and from about 0.01M to about 0.15M salt for wash conditions at about 55 to about 65° C., or higher, or conditions equivalent thereto.

The terms 'polypeptide' or 'protein' refers to a polymer of amino acids without regards to the length of the polymer. Thus, peptides, oligopeptides and proteins are included within the definition of polypeptide. Also included within the definition are polypeptides which contain one or more analogs of an amino acid, polypeptides with substituted linkages, as well as other modifications known in the art, both naturally occurring and non-naturally occurring.

The term 'cultured cells' means eukaryotic cells grown under controlled conditions, generally outside of their natural environment, including primary cells, cells lines and transgenic cells The cultured cells may, or may not be, transduced by a viral vector composition. The term 'target cells' means cells that are tested for expression of biomarkers by the method of the invention, or the kit of the invention. Target cells are preferably eukaryotic cells, more preferably immortalized cells, primary cells or stem cells. Same type, same culture conditions. For example, target cells are foreskin cells.

In particular, target cells can be permissive or non-permissive cells. The term << permissive cells >> are target cells which are transduced with a viral vector composition at optimal Multiplicity of Infection (MOI) value less than or equal 40. The term << non-permissive cells >> are target cells which are transduced with a viral vector composition at optimal MOI value more than 40.

Multiplicity of infection (MOI) is a frequently used term in virology which refers to the number of virions that are added per cell during infection.

The term "optimal MOI" means the appropriate MOI to transduce target cells. The optimal MOI is determined by a range of MOI on target cells, using a reporter gene expressing viral vector such as reporter gene expressing lentiviral vector. Reporter gene is but not limited to fluorescent reporter gene such as GFP or luminescent reporter gene such as luciferase.

The optimal MOI can be determined by the skilled person, based on several criteria such as, but not limited to:
Percentage of transduced cells with a reporter gene expression level,
Viability of transduced cells, and/or
Reporter gene expression level.

Percentage of transduced cells and reporter gene expression level are determined by methods that are known to one ordinary skill in the art. In a preferred embodiment of the invention, the optimal MOI is determined by the MOI corresponding to the highest percentage of transduced cells, a reporter gene expression level sufficient to be detectable and a non-alteration of the viability of transduced cells compared to the viability of non-transduced cells.

For example, optimal MOI for fibroblast cells, such as foreskin fibroblast cells (also called "foreskin cells"), is 40.

The term "transfection" refers to the process of deliberately introducing nucleic acids into cells. The term is used strictly for non-viral methods in eukaryotic cells. Transfection is used in the process of viral vector production when gag-pol and env expressing plasmids are transfected on producer cells to get viral vectors in the supernatant.

The term "transduction" is the process of deliberately introducing nucleic acids into cells. The term is used for viral based methods in eukaryotic cells. Viral vectors are harvested from the producer cells and are contacted with the eukaryotic cells to obtain the finally transduced cells.

The terms "fold change" or "FC" represent the ratio between the expression level of cells transduced with a viral vector composition versus expression level of non-transduced cells or transduced with different batches of viral vector compositions.

The term 'cellular senescence' refers to stable cell cycle arrest accompanied by a set of characteristic morphological and physiological features that distinguish senescent cells from proliferating cells, as well as arrested quiescent or terminally differentiated cells (Kosar et al. 2011).

The term 'SASP' means "Senescence-Associated Secretory Phenotype" and is defined as a set of proteins secreted by cells undergoing cellular senescence.

The term "cell cycle" means the sequence of events within the cell between mitotic (cell) divisions. The cell cycle is conventionally divided into five phases: G0 (the gap); G1, (the first gap); S (the synthesis phase, during which the DNA is synthesized and replicated); G2 (the second gap); and M (mitosis).

The present invention provides a novel method for evaluating or measuring the effect of viral vector compositions on target cells, preferably eukaryotic cells by screening for modifications in the expression level of at least one biomarker in said target or eukaryotic cells. The method of the invention can be used to assess the quality of the viral vector compositions by establishing whether the viral vector composition has an impact on cultured cells. The target or eukaryotic cells can be cultured cells transfected to produce the viral vector compositions or cultured cells transduced with the viral vector compositions. The biomarkers can be cellular nucleic acids and/or cellular proteins or their selected fragments. The goal is to determine if viral vector composition itself, rather than the transgene carried by the viral vector, affects cultured cells wherein said affect can depend on the concentration and purity of the viral vector composition. Indeed, to date methods have been lacking for the skilled artisan to compare the effect of viral vector compositions on the viability and/or toxicity of the target or eukaryotic cells.

Moreover, viral vector compositions can have different concentrations and titers. The titre of the composition is a very important parameter of the composition as it determines the Multiplicity of Infection (MOI) applied to cultured cells. The titre determination depends on several factors, i.e the measurement techniques and data processing. Typically, investigators have focused on vector pseudotyping or transduction protocol optimizations to improve the transduction efficiency (Janssens et al., 2003) although the use of higher MOI is the clue to reaching high transduction levels. However, since such a batch B-S induces cell toxicity (Selvaggi et al., 1997; Reiser, 2000; Baekelandt et al., 2003), the results of transduction efficiency with this type of product B-S are always a balance between the transduction level and the resulting toxicity on target cells. Furthermore, another drawback of published retroviral or lentiviral vectors concentrated by classical techniques is the inability of transduced stem cells, particularly for hematopoietic stem cells, to progress down differentiation pathways after transduction. Thus, the present invention provides methods for determining the effect of viral vector compositions, at different MOIs, on transduced cells. The present invention allows one to determine the range of MOI corresponding to a given viral vector composition and also optimize the protocols used for cell transduction. Particularly, the use of biomarkers of the present invention permits one to define the appropriate range of MOI that allows an efficient transduction without inducing deleterious or undesirable effects on transduced cells, as cell cycle arrest or cellular senescence.

To study the mechanisms underlying the cellular response of transduced cells to viral vector compositions, a model system was developed based on the discovery of differentially expressed biomarkers in transduced cells, wherein the pattern of biomarker expression correlates with the quality of the viral vector composition (viral vector without cDNA). Accordingly, the present invention is based on the identification and validation of a number of biomarkers whose expression is modified after contacting with a viral vector composition. The invention is based on data generated with different viral vector compositions (different levels of concentration/purity) and different values of MOI to identify reliable biomarkers to measure the impact of viral vector compositions on cultured eukaryotic cells. In particular, the differences on expression levels of transduced cells genes has been compared between expression levels of non-transduced cells genes versus transduced cells genes with a viral vector without cDNA. Some genes identified as biomarkers are retested via microarrays experiments and/or RT-qPCR quantification of expression level in cells transduced with viral vectors compositions compared to non-transduced cells. For these validation experiments, a particular attention is given to the titration of viral vectors compositions. For example, viral vector compositions are titrated three times at different moments.

The present invention concerns a profile of biomarkers corresponding to molecules which are up or down regulated in transduced target cells, preferably eukaryotic cells, by a viral vector composition according to the invention. In a preferred embodiment of the invention, the change in biomarker expression level between non-transduced cells and transduced cells is established at a minimal absolute value of 1.3 FC (fold change ≥1.3) in expression, either a 1.3 fold increase in expression or a 1.3 decrease in expression. The FC value is correlated to the quality of the viral vector composition and to the conditions of transduction, in particular to the MOI. The profile of biomarkers is useful to characterize the biological specific state of the transduced cells according to the invention. The profile comprises the biomarkers of the Table 2, Table 3, Table 4, Table 6, Table 7 and Table 8.

Comparison of gene expression levels between pre-transduced and post-transduced cells identified a gene expression signature composed of over-expressed and under-expressed genes. Accordingly, the present invention provides methods for assessing the quality of a viral vector composition. The methods of the invention rely on measurement of the expression level of one or more predictive RNA transcripts or their expression products in a transduced cell, normalized against the expression level of the RNA transcripts or their expression products in an untransduced cell, or against a reference set of RNA transcripts or their expression products, wherein the predictive RNA transcript is the transcript of one or more genes selected from the group consisting of the genes listed in Table 2, Table 3, Table 4, Table 6, Table 7, Table 8. While individual biomarkers are useful in assessing the quality of a viral vector composition, the combination of biomarkers as proposed herein, enables a more accurate determination of the quality of a biomarker composition.

Expression levels of the biomarkers in a sample may be determined by comparison to a suitable "control" or "reference" sample. For example, the relative expression level of markers in viral vector transduced cell may be determined with reference to the expression level of the same markers in a non-viral vector transduced cell. If the expression level of markers is greater or less than that of the reference, markers expression may be said to be "increased" or "decreased", respectively. Additionally, it is possible that the expression levels may remain constant between the control or reference and the sample.

The term "significant" change (upregulation or down-regulation) is a change in the expression level which is important enough to be interpreted by the skilled person as meaningful. In particular, the change in the expression level is significant when the expression level of the transduced cells doesn't correspond to the expression level in the non-transduced cells taking into account the margin of error. In a preferred embodiment of the invention, a significant change in biomarker expression level between non-transduced cells and transduced cells is established at a minimal absolute value of 1.3 FC (fold change ≥1.3) in expression, either a 1.3 fold increase in expression or a 1.3 decrease in expression. This minimal absolute value of 1.3 FC was considered for the first analysis with biochips. For validation experiment, independent t-tests were performed with Benjamini-Hochberg multiple test correction and a corrected p-value<0.05. Probes with absolute value of fold changes (FC)≥1.5 were retained as differentially expressed for both up and down-regulated probes.

Samples for analysis in such methods can be any target cell, preferably eukaryotic cell or eukaryotic cell extract. Such eukaryotic cells include cell lines, cultured cells, primary cells, stem cells.

As described in detail below, expression of the biomarkers within a cell may be evaluated by any suitable means. For example, expression may be evaluated using DNA microarrays. Alternatively, RNA transcripts may be measured using real time PCR, or, when RNA corresponds to a coding gene, protein products may be detected using suitable antibodies. Methods of determining expression levels of genes by these and other methods are known in the art.

In the interest of brevity, Applicants are not expressly listing every possible combination of gene products suitable for use in the methods of the invention. Nevertheless, it should be understood that every such combination is contemplated and is within the scope of the invention. It is specifically envisioned that any combination of gene products listed in Tables 2, 3, 4, 6, 7 or 8 that were found to be differentially expressed between a control or reference, for example, untransduced cells, and the transduced cells may be particularly useful for analysis.

In a particular embodiment, the present invention further provides a method for assessing the quality of a viral vector composition for a transgene transfer into target cells comprising:

(a) measuring the expression level of at least one biomarker selected in the group consisting of CXCL2 and EREG in target cells that has not been contacted with the viral vector composition;

(b) measuring the expression level of said at least one biomarker in target cells following contact with said viral vector composition; and (c) comparing said biomarker(s) expression in (b) to the biomarker(s) expression in (a) wherein an significant upregulation in biomarker expression level in (b) compared to (a) indicates that the quality of the viral vector composition is insufficient.

By "transgene", it is more specifically intended any nucleic acid of interest. A transgene is but not limited to reporter gene (GFP, luciferase . . . ), any gene or combination of gene(s) portion(s) or sequence of interest such as shRNA (short hairpin RNA) or miRNA (micro RNA).

The term "insufficient" quality means that the viral vector composition to be tested modifies some characteristics of the transduced cells compared to non-transduced cells. Examples of modified characteristics are but not limited to the proliferation and/or the viability of the transduced cells compared to non-transduced cells. In particular, these characteristics are not modified when the viral vector composition is a concentrated and purified viral vector composition, such as a viral vector composition produced without serum, concentrated and purified by tangential ultrafiltration and diafiltration, such as obtained by the method described in patent application WO 2013/014537.

More specifically, said method for production of viral vector composition comprises the steps of:
  transfection of a producer cell, modified to complement deletions in the RNA viral genome upon which the viral vector is based, and culturing the producer cells under suitable conditions to permit the production of viral vector particles, wherein said culturing following transfection is conducted in serum free medium;
  collecting the supernatant containing said viral vector particles; and
  purifying the supernatant by tangential ultrafiltration and diafiltration, the ultrafiltration being preferably operated on polysulfone hollow-fiber cartridges.

In particular, this method of production of viral vector composition doesn't comprise any step of sodium butyrate induction.

Advantageously, the supernatant collection is performed by multiple steps comprised between 3 and 6, at specific time intervals. The supernatant collection is followed by clarification by centrifugation.

The method of production may further comprise a step of ion-exchange chromatography.

This method of production allows obtaining a purified viral vector composition comprising less than 2% of initial protein contaminants and 10 to 30%, preferably less than 10%, of initial DNA contaminants, compare to the crude viral vector composition as present in the cell serum free medium.

In particular, said viral vector composition is capable of transducing target cells, in particular eukaryotic cells, without affecting cell viability and/or have little to no effect on cell proliferation, viability, and/or the ability of cells, such as stem cells to differentiate or such as primary cells to be reprogrammed into pluripotent cells.

More particularly, in the viral vector composition obtained by the above mentioned production method, the physical particles/transducing units (PP/TU) is usually comprised of between 100:1 up to 900:1, preferably between 100:1 up to 600:1, more preferably between 100:1 up to 400:1.

In the present method for assessing the quality of a viral vector composition for a transgene transfer into target cells, a significant upregulation at high MOI is preferably a two fold upregulation compared to (a).

Advantageously, the expression level of the at least one biomarker can be measured by reverse transcription quantitative PCR (RT-qPCR)

The term "high MOI" means a very higher MOI than the optimal MOI. The high MOI is determined by a range of MOI using a reporter gene expressing viral vector such as reporter gene expressing lentiviral vector. Reporter gene is but not limited to fluorescent reporter gene such as GFP or luminescent reporter gene such as luciferase.

Preferably, the high MOI corresponds to:
at least three times the optimal MOI for non-permissive cells,
at least four times for permissive cells.

For example, high MOI for fibroblast cells, such as foreskin fibroblast cells, is at least 120, such as 150.

The method for assessing the quality of a viral vector composition for a transgene transfer into target cells can further comprise a step of:

(d) measuring the expression level of at least one biomarker selected in the group consisting of ASPM, AURKB, CENPA, CENPF, CKS1B, E2F8, ERCC6L, FAM83D, KIFC1, MKI67, NEK2, NUSAP1, OIP5, PRC1, RRM2, SGOL1, SPC25, TOP2A and TTK in target cells that has not been contacted with the viral vector composition;

(e) measuring the expression level of said at least one biomarker in target cells following contact with said viral vector composition; and (f) comparing said biomarker(s) expression in (e) to the biomarker(s) expression in (d) wherein an significant downregulation in biomarker expression level in (e) compared to (d) indicates that the quality of the viral vector composition is insufficient.

More particularly, a significant downregulation at optimal MOI is a 1.5 fold downregulation compared to (d).

Advantageously, the expression level of the at least one biomarker can be measured by reverse transcription quantitative PCR (RT-qPCR).

The method according to the present invention can further comprise a step of:

(g) measuring the expression level of at least one biomarker selected in the group consisting of CXCL2 and EREG in target cells following contact with a control viral vector composition; and (h) comparing said biomarker(s) expression in (g) to the biomarker(s) expression in (a), wherein no significant differential expression in biomarker(s) has to be detected in (g) compared to (a).

This significant differential expression in biomarker(s) has not to be detected even at high MOI.

The term "control viral vector composition" means a highly concentrated and purified viral vector composition. It can be obtained by, but not limited to single or successive tangential ultrafiltration diafiltration, by ion-exchange chromatography, exclusion chromatography. In a preferred embodiment of the invention, the control viral vector composition is such as obtained by the process of production described in patent application WO 2013/014537 (see for example "batch C" in this PCT application) and/or described above.

The method according to the present invention can further comprise a step of:

(j) measuring the expression level of at least one biomarker selected in the group consisting of ASPM, AURKB, CENPA, CENPF, CKS1B, E2F8, ERCC6L, FAM83D, KIFC1, MKI67, NEK2, NUSAP1, OIP5, PRC1, RRM2, SGOL1, SPC25, TOP2A and TTK in target cells following contact with a control viral vector composition; and (k) comparing said biomarker(s) expression in (j) to the biomarker(s) expression in (d) wherein a potential downregulation in biomarker expression level in (j) compared to (d) has to be detected.

More particularly, the potential downregulation in biomarker expression level in (j) compared to (d) is at least 1.5 times less than the downregulation in biomarker expression level in (e) compared to (d) at high MOI.

The method according to the present invention can further comprise beforehand a step of titration of the viral vector composition and the control viral vector composition.

Titers of viruses in general, and lentiviral based vectors in particular, depend on the method and cells used for titration. The quantification of vector particles capable of achieving the steps of the transduction pathway from cell entry to gene integration and gene expression depends on the vector itself and cell characteristics.

Concerning the cells used for vector titration, it is important to ensure that the target cells are readily permissive, as it was demonstrated that the permissivity of all the cell types are not equivalent. Another point is that the transduction efficiency must be easily monitored for reliable quantification for any transgenes and vectors over time. Here, in each titration experiment a standard GFP expressing lentiviral vector is quantified in terms of efficient units both by FACS (represented by the number of Transducing Units per ml TU/ml) and qPCR (represented by the number of Integrated Genome per ml IG/ml) after HCT116 transduction with serial dilutions of the vectors according to the material and methods as set forth above. Both results give a relative number of efficient particles for transduction but their respective absolute numbers do not give the same titer depending on the PCR itself and the target sequence used for amplification. These data show that it can be difficult to compare precisely these different approaches based on the functional titers in the absence of standardized methods. It can thus be of interest to include a control viral vector composition in the present method. Said control viral vector composition is thus a reference batch with preferably a known titer and a define target cell type.

In parallel, the determination of total particles is quantified with the P24 Elisa kit to estimate the total vector particles, even those that do not contain any genomic RNA and/or that are devoid of envelope proteins. Both titers are useful to determine the ratio between the physical particles PP that reflect the total particles and the biological titer that gives the real transduction ability. This ratio gives an estimation of the vector purity and integrity. Another ratio is used to reflect the vector integrity or infectivity and is expressed as the number of IG per ng P24 (1 ng of P24 corresponds to 107 PP).

Advantageously, in the method according to the invention, the measures of the biomarker expression level are performed before the cells reach confluency.

Preferably, the target cells are eukaryotic cells and are transduced by a lentiviral vector composition.

To determine the (increased, decreased) expression levels of the above described biomarkers in the practice of the present invention, any method known in the art may be utilized. In one preferred embodiment of the invention, expression based on detection of RNA which hybridizes to a "probe" or "primer" specific for the biomarkers described herein is used. A "probe" or "primer" is a single-stranded DNA or RNA molecule of defined sequence that can base pair to a second DNA or RNA molecule that contains a complementary sequence (the target). The stability of the resulting hybrid molecule depends upon the extent of the base pairing that occurs, and is affected by parameters such as the degree of complementarity between the probe and target molecule, and the degree of stringency of the hybridization conditions. The degree of hybridization stringency is affected by parameters such as the temperature, salt concentration, and concentration of organic molecules, such as formamide, and is determined by methods that are known to those skilled in the art.

Probes or primers specific for the nucleic acid biomarkers described herein, or portions thereof, may vary in length by any integer from at least 8 nucleotides to over 500 nucleotides depending on the purpose for which, and conditions under which, the probe or primer is used. Probes or primers specific for the nucleic acid biomarkers described herein may have greater than 20-30% sequence identity, or at least 55-75% sequence identity, or at least 75-85% sequence identity, or at least 85-99% sequence identity, or 100% sequence identity to the nucleic acid biomarkers described herein. Probes or primers may be derived from genomic DNA or cDNA, for example, by amplification, or from cloned DNA segments, and may contain either genomic DNA or cDNA sequences representing all or a portion of a single gene from a single individual. Probes or primers may be chemically synthesized.

A probe or primer may hybridize to a nucleic acid biomarker under high stringency conditions as described herein. "Stringent hybridization conditions" as used herein mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. Lower than the thermal melting point (Tm) for the specific sequence at a defined ionic strength pH. The Tm may be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

Probes or primers can be detectably-labeled, either radioactively or non-radioactively, by methods that are known to those skilled in the art. By "detectably labeled" is meant any means for marking and identifying the presence of a molecule, e.g., an oligonucleotide probe or primer, a gene or fragment thereof, or a cDNA molecule. Methods for detectably-labeling a molecule are well known in the art and include, without limitation, radioactive labeling (e.g., with an isotope such as 32P or 35S) and nonradioactive labeling such as, enzymatic labeling (for example, using horseradish peroxidase or alkaline phosphatase), chemiluminescent labeling, fluorescent labeling (for example, using fluorescein), bioluminescent labeling, or antibody detection of a ligand attached to the probe. Also included in this definition is a molecule that is detectably labeled by an indirect means, for example, a molecule that is bound with a first moiety (such as biotin) that is, in turn, bound to a second moiety that may be observed or assayed (such as fluorescein-labeled streptavidin). Labels also include digoxigenin, luciferases, and aequorin.

Probes or primers can be used in biomarker detection methods involving nucleic acid hybridization, such as nucleic acid sequencing, nucleic acid amplification by the polymerase chain reaction (e.g., RT-PCR), single stranded conformational polymorphism (SSCP) analysis, restriction fragment polymorphism (RFLP) analysis, Southern hybridization, northern hybridization, in situ hybridization, electrophoretic mobility shift assay (EMSA), fluorescent in situ hybridization (FISH), and other methods that are known to those skilled in the art.

A preferred biomarker detection method is reverse transcription quantitative PCR (RT-qPCR).

A preferred embodiment using a nucleic acid based assay to determine biomarker expression is by immobilization of one or more biomarker sequences identified herein on a solid support, including, but not limited to, a solid substrate as an array or to beads or bead based technology as known in the art. Alternatively, solution based expression assays known in the art may also be used. The immobilized sequence(s) may be in the form of polynucleotides as described herein such that the polynucleotide would be capable of hybridizing to a DNA or RNA corresponding to the biomarker sequence(s).

The immobilized polynucleotide(s) may be used to determine the biomarker expression signature in a sample of transduced and non-transduced cells. The immobilized polynucleotide(s) need only be sufficient to specifically hybridize to the corresponding nucleic acid molecules derived from the sample (and to the exclusion of detectable or significant hybridization to other nucleic acid molecules).

In embodiments where only one or a few biomarkers are to be analyzed, the nucleic acid derived from a sample isolated from cells may be preferentially amplified by use of appropriate primers such that only the genes to be analyzed are amplified to reduce contaminating background signals from other genes expressed in the cell. Alternatively, and where multiple genes are to be analyzed or where very few cells (or one cell) is used, the nucleic acid from the sample may be globally amplified before hybridization to the immobilized polynucleotides. Of course RNA, or the cDNA counterpart thereof may be directly labeled and used, without amplification, by methods known in the art.

A biochip may be used in the practice of the invention.

In particular, the present invention provides a biochip consisting of at least a biomarker selected in the group consisting of CXCL2 and EREG and at least one biomarker selected in the group consisting of ASPM, AURKB, CENPA, CENPF, CKS1B, E2F8, ERCC6L, FAM83D, KIFC1, MKI67, NEK2, NUSAP1, OIP5, PRC1, RRM2, SGOL1, SPC25, TOP2A and TTK with optionally a ubiquitous gene.

The biochip may comprise a solid substrate comprising an attached probe or plurality of probes described herein. The probes may be capable of hybridizing to a target sequence under stringent hybridization conditions. The probes may be attached at spatially defined sites on the substrate. More than one probe per target sequence may be used, with either overlapping probes or probes to different sections of a particular target sequence. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, Teflon J, etc.), polysaccharides, nylon or nitrocellulose, resins, silica or silica-based materials including silicon and modified silicon, carbon, metals, inorganic glasses and plastics. The substrates may allow optical detection without appreciably fluorescing.

Biomarker expression may also be measured based on detection of a presence, increase, or decrease in protein levels or activity may also be used. Antibody based detection methods are well known in the art and include sandwich and ELISA assays as well as Western blot and flow cytometry based assays as non-limiting examples. Antibodies for use in such methods of detection include polyclonal antibodies and monoclonal antibodies that specifically bind to the biomarkers of Tables 2, 3, 4, 6, 7 and 8.

Preferably, the antibodies for use in such methods of detection include polyclonal antibodies and monoclonal antibodies that specifically bind to at least one biomarker selected in the group consisting of CXCL2 and EREG and/or at least one biomarker selected in the group consisting of ASPM, AURKB, CENPA, CENPF, CKS1B, E2F8, ERCC6L, FAM83D, KIFC1, MKI67, NEK2, NUSAP1, OIP5, PRC1, RRM2, SGOL1, SPC25, TOP2A and TTK.

Such antibodies, as well as fragments thereof (including but not limited to Fab fragments) function to detect such biomarkers in cells by virtue of their ability to specifically bind to such polypeptides to the exclusion of other polypeptides to produce a detectable signal. Recombinant, synthetic, and hybrid antibodies with the same ability may also be used in the practice of the invention.

In a preferred embodiment, biomarker expression may also be measured by RT-qPCR. The present invention still further provides a RT-qPCR plate comprising primers of at least a biomarker selected in the group consisting of CXCL2 and EREG and primers of at least one biomarker selected in the group consisting of ASPM, AURKB, CENPA, CENPF, CKS1B, E2F8, ERCC6L, FAM83D, KIFC1, MKI67, NEK2, NUSAP1, OIP5, PRC1, RRM2, SGOL1, SPC25, TOP2A and TTK.

Example of primers that can be used in the RT-qPCR plate for EREG and CXCL2 are given in Table 10.

The present invention is based on the identification and the validation of target cell biomarkers that can be used to assess the quality of a viral vector composition. In a preferred embodiment, the biomarkers are selected from those genes listed in Table 2, Table 3, Table 4, Table 6, Table 7, Table 8. As described in detail below, three families of biomarkers were identified: (i) biomarkers associated with senescence, (ii) biomarkers associated with the cell cycle, and (iii) others biomarkers found to be associated with the quality of the viral vector compositions.

To identify these biomarkers, gene expression was determined using different viral vector compositions obtained as follows. Producer cells were tri-transfected with plasmids constructs as described in FIG. 1C, according to standard techniques well known to those skilled in the art. Such techniques include, for example, the calcium phosphate technique, the DEAE-dextran technique, electroporation, methods based on osmotic shock, microinjection or methods based on the use of liposomes. In a specific embodiment of the invention, the cells may be transfected using a calcium precipitation method. Such a method is preferred when 293T cells are the producer cells of choice but equivalent cells may also be used.

Figure 1B:
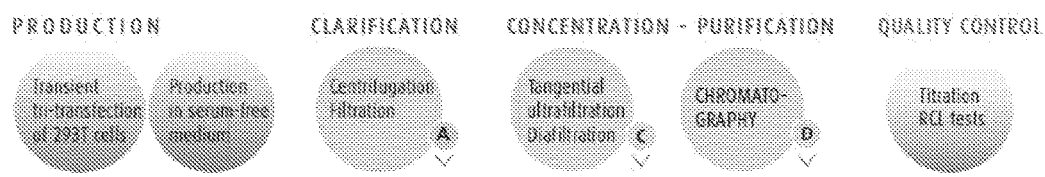

Following transfection, the cells are incubated in serum free media for production of batch A, B C and D (FIG. 1B). Batch B-S is produced with 10% serum (FIG. 1A) Cells are incubated for a time sufficient to allow for the efficient production of viral particles. The incubation time following transfection, depends on a combination of factors including, for example, the type of viral vector used and the producer cell line of choice. In a specific embodiment of the invention, multiple harvests may take place following incubation. For example, four or more vector harvests may take place. To determine, the most productive incubation conditions, small batch experiments may be performed to determine optimized conditions for generating the highest titre and purest batch of viral particles.

The initial culture supernatant, containing viral vector particles, is referred to herein as, batch A. The batch B is obtained by commonly used prior art concentration methods (FIG. 1A) such as a concentration step by ultrafiltration using centrifugation ready-to-use units on the post clarification harvest. The method of obtaining a viral vector composition may further comprise the step of tangential ultrafiltration diafiltration of the batch A product for further purification of viral vector particles. Such an ultrafiltration diafiltration step is a type of membrane filtration in which hydrostatic pressure forces a liquid against a semi-permeable membrane. Suspended solids and solutes of higher molecular weight than the membrane cut off are retained, while water and lower molecular weight than the membrane cut off solutes pass through the membrane. Ultrafiltration technique is carried out by tangential flow ultrafiltration using polysulfone hollow-fiber cartridges. Such a technique allows for monitoring and adapting the pressure to ensure the maintenance of vector integrity and viability. Such a step provides for concentration of the vector particles, as well as acting as a purification step for removal of initial contaminants, such as host cell proteins and nucleic acids, from the collected batch. Such a batch is referred to herein as batch C.

In yet another embodiment of the invention, following the tangential ultrafiltration and/or diafiltration step, the method of obtaining a viral vector composition may further comprise the step of ion-exchange chromatography which may be performed to further concentrate and purify the viral vector particles. Such a batch is referred to herein as batch D.

Biomarkers have been identified by analyzing microarray experiments targeting the nucleic acids of cells, for example, human foreskin fibroblast cells transduced with batches B (obtained by process B), C (obtained by process C), B-S (obtained by process B with serum), UC or UC-S (obtained in presence of serum and concentrated by ultracentrifugation) or non-transduced (NT).

In a specific embodiment of the invention, genes involved in cellular senescence have been identified as useful biomarkers for determining the quality of a viral vector composition. Senescence is a permanent state of cell cycle arrest that, unlike quiescence, is unresponsive to growth factors (Young et al.). Originally described in terms of the replicative exhaustion of cultured fibroblasts, it has since been shown that senescence can occur prematurely upon a plethora of cellular stresses. Cellular senescence occurs in culture and in vivo as a response to excessive extracellular or intracellular stress. Induction of DNA damage response and chromatin remodeling of the INK4a/ARF locus are two of the mechanisms behind senescence induction. Li et al. (2009) demonstrated that cell culture conditions during reprogramming enhance the expression of the Ink4/Arf locus, further highlighting the importance of silencing this locus to allow proliferation and efficient reprogramming. Limiting senescence by using a highly purified vector suspension to overexpress combinations of factors such as Oct4, Sox2, Klf4, and c-Myc may have a profound positive effect on the efficiency of iPS cell generation, increasing both the kinetics of reprogramming and the number of emerging iPS cell colonies.

The present invention discloses the use of genes involved in the senescence phenotype to evaluate the impact of viral vector compositions on target cells. In a preferred embodiment of the present invention, the biomarker involved in cellular senescence phenotype listed in Table 5 or Table 6.

The senescent phenotype is not limited to an arrest of cell proliferation. A senescent cell is a potentially persisting cell that is metabolically active and has undergone widespread changes in protein expression and secretion, ultimately developing the senescence-associated secretory phenotype or SASP (Coppé et al. 2010). The SASP includes several families of soluble and insoluble factors. SASP factors can be soluble signaling factors (interleukins, chemokines, and growth factors), secreted proteases, and secreted insoluble proteins/extracellular matrix components (Coppé et al. 2010). Senescent cells develop altered secretory activities that may induce changes in the tissue microenvironment, relaxing its control over cell behavior and promoting tumorigenesis (Coppé et al. 2010). In cell culture, cell cycle arrest typically leads to senescence, because the cell is over-stimulated by serum, nutrients, oncogenes and so on (Blagosklonny, 2011). The present invention discloses the use of genes involved in SASP to evaluate the impact of viral vector compositions on target cells in contact with such compositions. In a preferred embodiment of the present invention, biomarkers associated with SASP, include those listed in Table 7.

In a specific embodiment of the invention, genes involved in cell cycle have been identified as useful biomarkers for determining the quality of a viral vector composition. Cell division consists of two consecutive processes, mainly characterized by DNA replication and segregation of replicated chromosomes into two separate cells. Originally, cell division was divided into two stages: mitosis (M), i.e. the process of nuclear division; and interphase, the interlude between two M phases. Stages of mitosis include prophase, metaphase, anaphase and telophase. Under the microscope, interphase cells simply grow in size, but different techniques revealed that the interphase includes G1, S and G2 phases. Replication of DNA occurs in a specific part of the interphase called S phase. S phase is preceded by a gap called G1 during which the cell is preparing for DNA synthesis and is followed by a gap called G2 during which the cell prepares for mitosis. G1, S, G2 and M phases are the traditional subdivisions of the standard cell cycle. Cells in G1 can, before commitment to DNA replication, enter a resting state called G0. Cells in G0 account for the major part of the non-growing, non-proliferating cells in the human body. The present invention discloses the use of genes involved in cell cycle to evaluate the impact of viral vector compositions on target cells in contact with such compositions. In a preferred embodiment of the present invention, biomarkers associated with cell cycle, include those listed in Table 2, Table 3, Table 4. In a more preferred embodiment of the present invention, the screening of the modification is realized on expression level of at least one biomarker associated to cell cycle, listed in Table 4.

The present invention further discloses a class of biomarkers whose expression level in the target cells is modulated depending on the quality, i.e concentration and purification, of the viral vector compositions used. The impact of viral vector compositions having different qualities and obtained by different processes was investigated to select a novel class of biomarkers. The viral vector compositions were obtained by the processes described in FIGS. 1A and 1B. In a preferred embodiment of the present invention, the use of genes listed in Table 8, may be used to evaluate the impact of viral vector compositions on target cells in contact with such compositions.

The invention also provides kits for measuring the level of biomarker expression in a sample of transduced cells. The kits may include one or more reagents corresponding to the biomarkers described herein, e.g., antibodies that specifically bind the biomarkers, recombinant proteins that bind biomarker specific antibodies, nucleic acid probes or primers that hybridize to the biomarkers, etc. In some embodiments, the kits may include a plurality of reagents, e.g., on an array, corresponding to the biomarkers described herein. The kits may include detection reagents, e.g., reagents that are detectably labeled. The kits may include written instructions for use of the kit in predicting the quality of a viral vector composition, and may include other reagents and information such as control or reference standards, wash solutions, analysis software, etc.

The present invention discloses a method for screening or detecting a nuclear or a cellular response in eukaryotic cells transduced with a viral vector composition comprising (i) measuring the expression level of one or more biomarkers in a eukaryotic cell that has not been contacted with a viral vector composition; (ii) measuring the expression level of one or more biomarkers in a eukaryotic cell following contact with a viral vector composition; and (iii) comparing the biomarker(s) expression in (i) to the biomarker(s) expression in (ii) wherein a change in biomarker expression level between (i) and (ii) indicates a cellular response and wherein said cellular response is correlated to the quality of the viral vector composition. In a preferred embodiment of the invention, the expressed one or more biomarker is a nucleic acid expressed within the eukaryotic cells in contact with a viral vectors composition.

In another embodiment of the invention, the expressed one or more biomarker is a polypeptide expressed within the eukaryotic in contact with viral vectors composition.

In a specific embodiment of the invention, the biomarker is a gene involved in the senescence biological process. Preferably, the biomarker involved in senescence is a gene of the SASP family. More preferably, the biomarker is selected from Table 7.

In a specific embodiment of the invention the biomarker is a gene of cell cycle family. Particularly, the biomarker is a gene selected from Table 2, Table 3, Table 4. More particularly, the biomarker is selected from the genes listed in Table 8.

In another embodiment of the invention, the biomarker is selected from Table 2, Table 3, Table 4, Table 7 and/or Table 8.

In one embodiment of the invention the viral vector composition is transduced into the eukaryotic cell. In another embodiment of the invention, eukaryotic cells are transduced by a lentiviral vector composition. In a specific embodiment of the invention, the eukaryotic cells are immortalized cells, primary cells or stem cells.

The present invention discloses a method for measuring or detecting the effects of a viral vector composition on eukaryotic cells according to claim 1 comprising:

(i) contacting said cells with a viral composition of interest, (ii) measuring the level of biomarker expression in said cultured cells; and (iii) optionally characterizing the biomarkers specific of the modifications of the nuclear or of the cytoplasmic expressions in said cells.

The present invention discloses a kit for measuring the expression of a biomarker associated with the transduction of a viral vector composition comprising one or more reagents corresponding to recognition of the biomarkers of Table 2, 3, 4, 5, 6, 7 or 8. Preferably, the reagent corresponds to the recognition of nucleic acids encoding the biomarkers of Table 2, 3, 4, 5, 6, 7 or 8. More preferably, the reagent corresponds to the recognition of polypeptides of Table 2, 3, 4, 5, 6, 7 or 8.

In a preferred embodiment, the kit comprises one or more reagents able to measure the expression level of at least one biomarker selected in the group consisting of CXCL2 and EREG.

Advantageously, said kit further comprises one or more reagents able to measure the expression level of at least one biomarker selected in the group consisting of ASPM, AURKB, CENPA, CENPF, CKS1B, E2F8, ERCC6L, FAM83D, KIFC1, MKI67, NEK2, NUSAP1, OIP5, PRC1, RRM2, SGOL1, SPC25, TOP2A and TTK.

Preferably, said kit can also further comprise a control viral vector composition.

The present invention discloses a biomarker composition useful for the measurement or detection of the effect of a viral vector composition on eukaryotic cells comprising at least one of the products selected among the genes or the polypeptides present in Table 2, Table 3, Table 4, Table 5, Table 6, Table 7, Table 8. Preferably, the biomarker composition comprises at least one of the products selected among the genes or the polypeptides present in Table 3, Table 4, Table 7, Table 8.

Examples below are given with reference to the following figures and tables:

FIGURES

FIG. 1A. Common vector production method with serum by state of art processes. FIG. 1B. Viral vector concentration and purification process used to obtain the viral vector compositions B and C. The different processes are sequential (from A to D corresponding to the obtaining of batches A to D) to meet the target cells concentration and purification requirements: immortalized cells (A), primary and stem cells (C) and in vivo injection (D). Process B (corresponding to obtained batch B) represents the state of the art process. FIG. 1C. Plasmid harboring gag and pol genes, envelope expressing helper plasmid and transgene expression plasmid without cDNA.

Figure 2B:
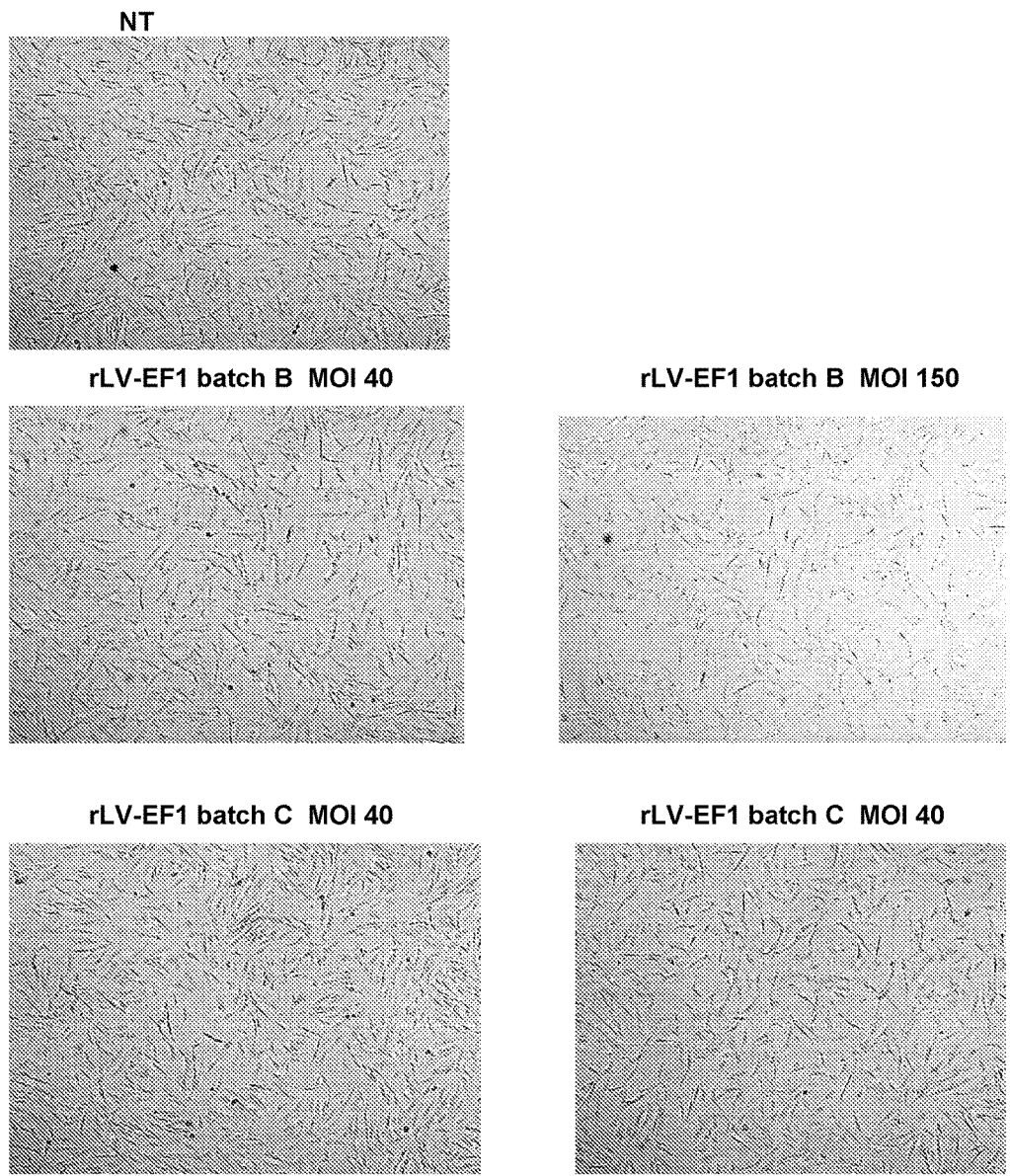

FIG. 2A. Summary of batch B and C titers used for the transcriptomics study. Characteristics of rLV-EF1 without cDNA batches B and C used for the transcriptomics study. (1) Transducing units (TU) were determined by qPCR. (2) Physical particles (PP) were quantified by HIV-p24 ELISA in order to determine PP/TU ratio. FIG. 2B. Foreskin cells growth 48 h post-transduction with batch B and C vectors. Foreskin cells 48 hours after transduction with an empty cassette carrying lentiviral vector (rLV-EF1 without cDNA) at MOI 40 or MOI 150. Batch B and C of rLV-EF1 were derived from the same crude harvest.

Figure 3A:
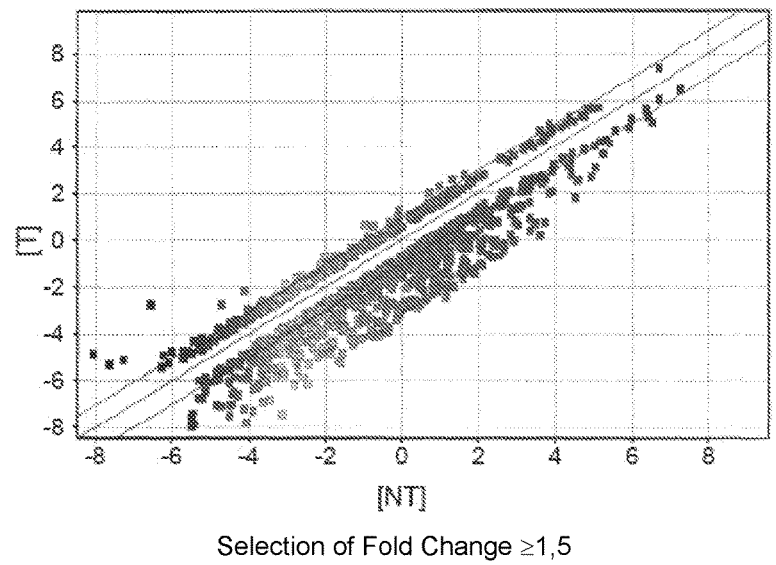
Figure 3B:
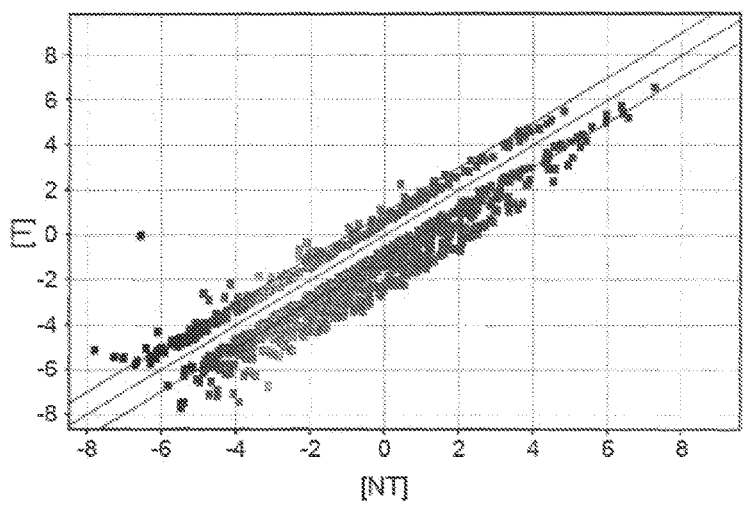

FIG. 3A. Scatterplot of differential probes in cells transduced with batch B at MOI 150 vs non-transduced cells. Scatterplot representing differentially expressed probes, with an absolute value of FC≥1.5, in rLV-EF1 batch B transduced cells at MOI 150 versus non-transduced cells. X-axis represents normalized intensities for Non-Transduced (NT) cells, and Y-axis normalized intensities for Transduced (T) cells. Very light grey tone lines are fold change lines representing fold changes values of −2, 1 and 2. FIG. 3B. Scatterplot of differential probes in cells transduced with batch C at MOI 150 vs non-transduced cells. Scatterplot representing differentially expressed probes, with an absolute value of FC≥1.5, in rLV-EF1 batch C transduced cells at MOI 150 versus non-transduced cells. X-axis represents normalized intensities for Non-Transduced (NT) cells, and Y-axis normalized intensities for Transduced (T) cells. Very light grey tone lines are fold change lines representing fold changes values of −2, 1 and 2.

Figure 4:
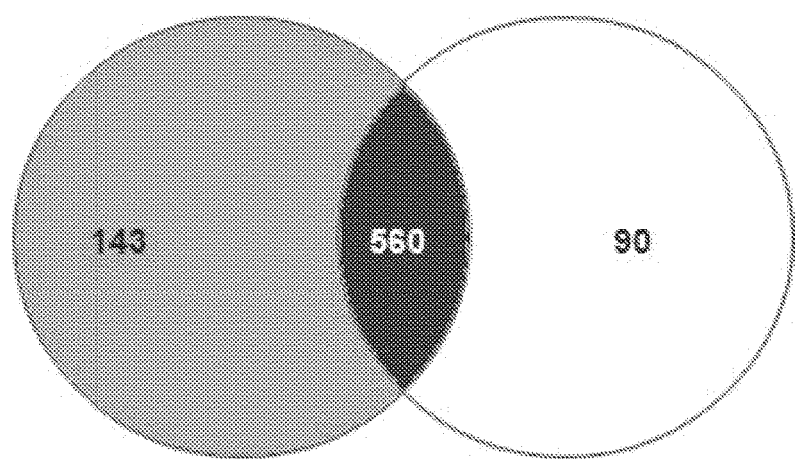

FIG. 4. Venn diagram: downregulated probes in cells transduced with batch B vs non-transduced cells and downregulated probes in cells transduced with batch C vs non-transduced cells MOI 150. Venn diagram showing the intersection between the list of downregulated probes (FC≤−1.5) in cells transduced with batch B at MOI 150 compared to non-transduced cells, and the list of downregulated probes (FC≤−1.5) in cells transduced with batch C at MOI 150 compared to non-transduced cells.

Figure 5:
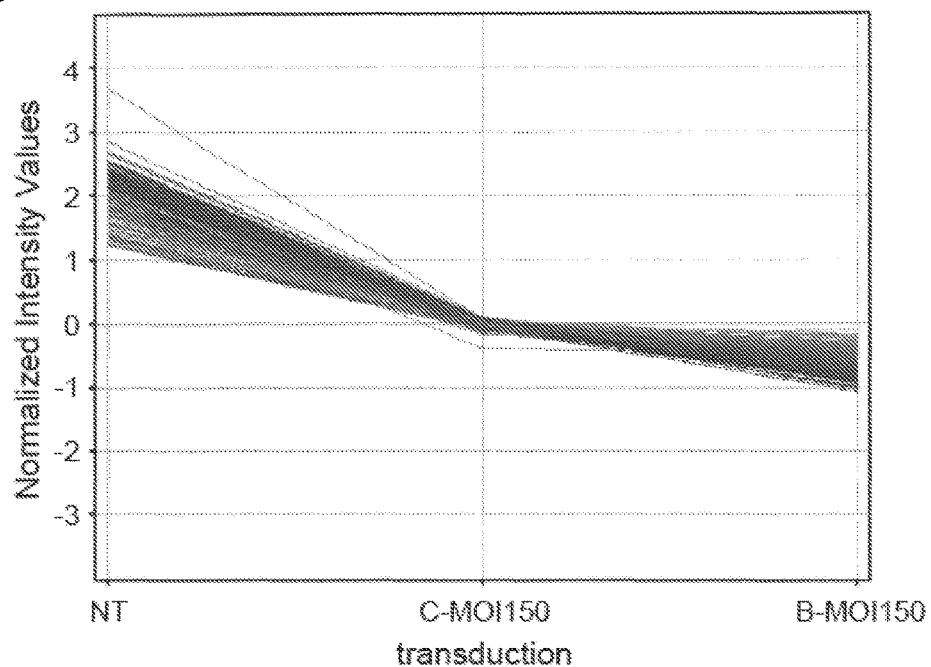

FIG. 5. Profile plot of cell cycle probes in cells transduced with batch B versus non-transduced cells at MOI 150 with FC≤−3. Profile plot representing differential probes having FC≤−3 when comparing batch B transduced cells at MOI 150 with non-transduced cells. A baseline transformation was applied on intensity values before representing data. Normalized intensity values are plotted in the following conditions: batch B transduced at MOI 150 cells, batch C transduced cells at MOI 150, non-transduced cell.

Figure 6A:
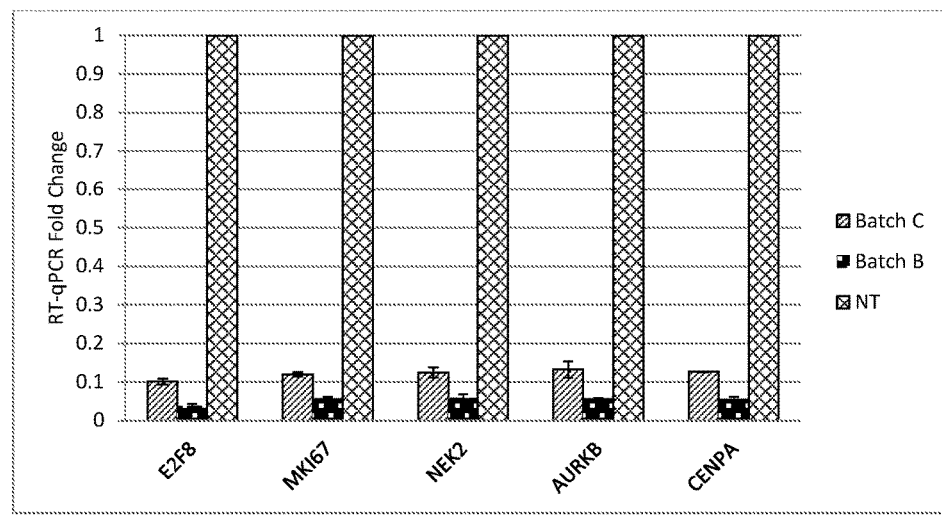

FIG. 6A. RT-qPCR validation of the downregulation of 5 cell cycle genes in cells transduced with rLV-EF1 batch B at MOI 150 and cells transduced with rLV-EF1 batch C at MOI 150 compared to non-transduced cells. RT-qPCR was performed on RNA from rLV-EF1 batch B and rLV-EF1 batch C transduced cells at MOI 150 and RNA from non-transduced cells. RT-qPCR fold changes, calculated from threshold cycle (Ct) values in each condition versus values in non-transduced cells, using the 2-ΔΔCT method, are plotted in the 3 conditions (NT: Non-Transduced cells, Batch C: rLV-EF1 batch C transduced cells at MOI 150, Batch B: rLV-EF1 batch B transduced cells at MOI 150). FIG. 6B. Comparison of Fold Changes values obtained with RT-qPCR and from microarray experiments for the 5 previously cited validated genes. All fold changes are calculated comparing expression values in cells transduced with rLV-EF1 batch B or batch C at MOI 150 versus expression values in the non-transduced cells. (1) HUGO Gene symbol, (2) Batch used for transduction at MOI 150, (3) Fold Change value calculated from Ct values using the 2-ΔΔCT method and transformed into equivalent negative value (−1/FC), (4) Fold change value from microarray experiment.

Figure 7A:
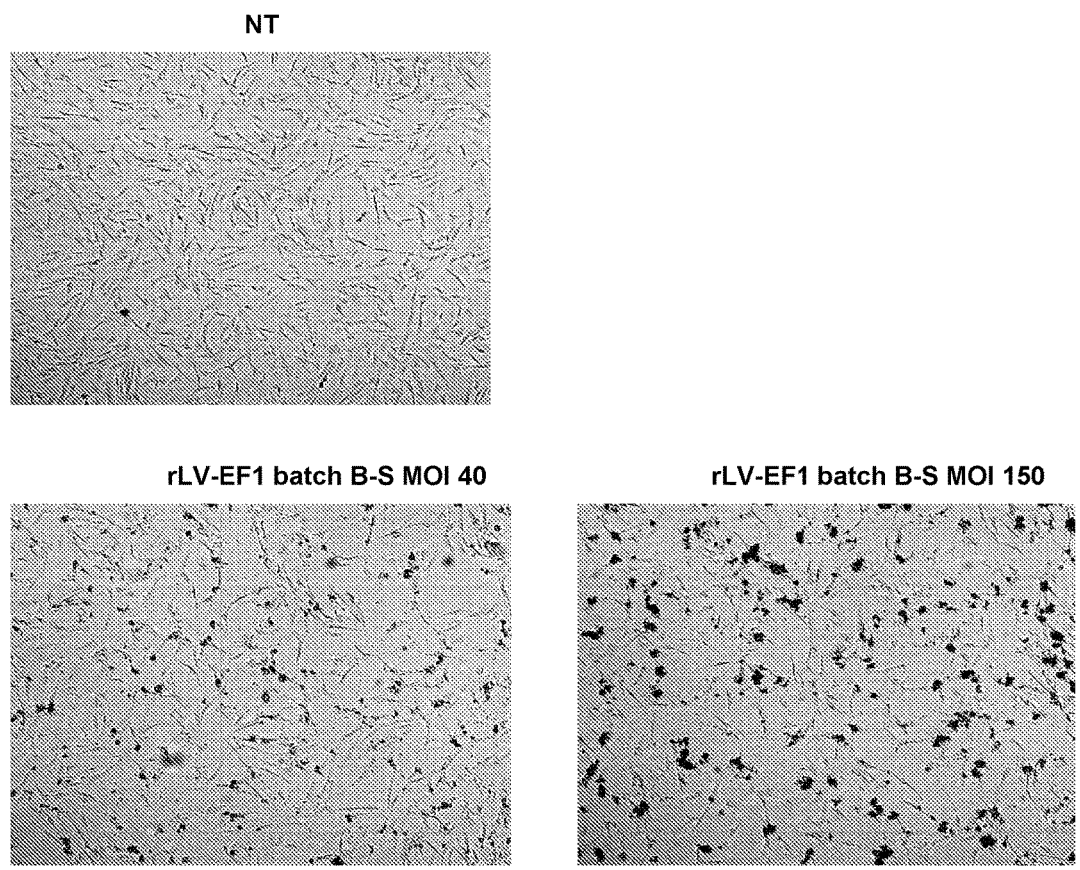

FIG. 7A. Cells transduced with batch B obtained with serum (batch B-S) compared to non-transduced cells. Foreskin cells 48 hours after transduction with an empty cassette carrying lentiviral vector (rLV-EF1 without cDNA) produced in the presence of serum at MOI 40 and MOI 150.

Figures 7B, 8:
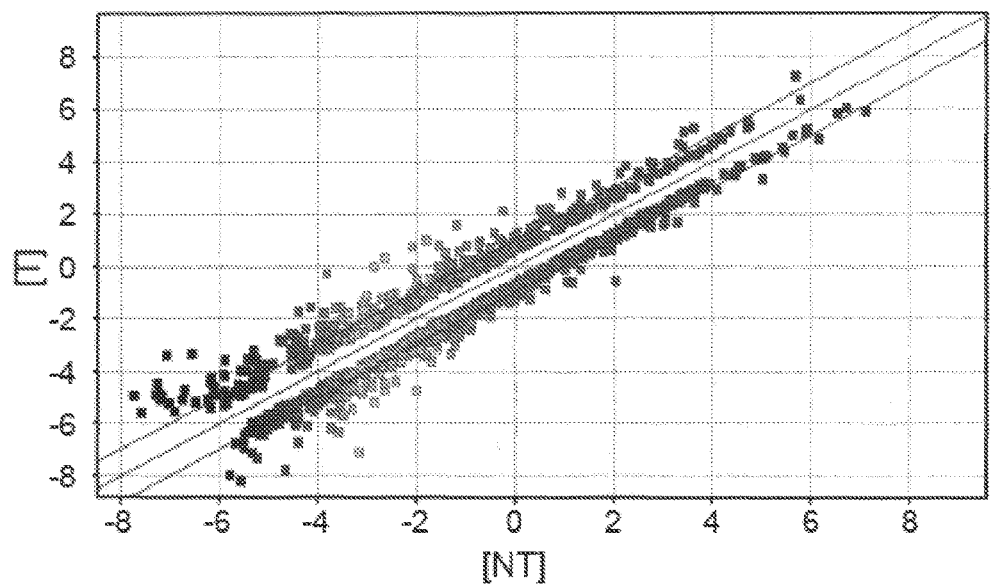

FIG. 7B. Characteristics of batch B-S of rLV-EF1 without cDNA used for the transcriptomics study. (1) Transducing units (TU) were determined by qPCR. (2) Physical particles (PP) were quantified by HIV-p24 ELISA in order to determine PP/TU ratio.

FIG. 8. Scatterplot of differential probes in cells transduced with batch B obtained with serum (B-S) versus non-transduced cells at MOI 150. Scatterplot representing differentially expressed probes, with an absolute value of FC≥1.5, in rLV-EF1 without cDNA batch B-S transduced cells at MOI 150 versus non-transduced cells. X-axis represents normalized intensities for Non-Transduced (NT) cells, and Y-axis normalized intensities for Transduced (T) cells. Very light grey tone lines are fold change lines representing fold changes values of −2, 1 and 2.

Figure 9:
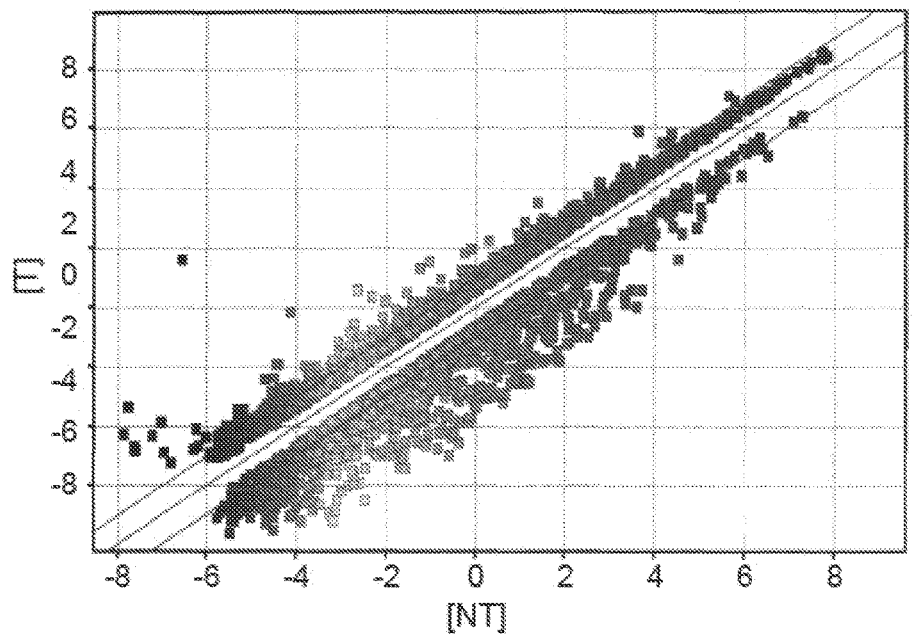

FIG. 9. Scatterplot of differential probes in cells transduced with batch B obtained with serum (B-S) versus non-transduced cells at MOI 40. Scatterplot representing differentially expressed probes, with an absolute value of FC≥1.5, in rLV-EF1 without cDNA batch B-S transduced cells at MOI 40 versus non-transduced cells. X-axis represents normalized intensities for Non-Transduced (NT) cells, and Y-axis normalized intensities for Transduced (T) cells. Very light grey tone lines are fold change lines representing fold changes values of −2, 1 and 2.

Figure 10:
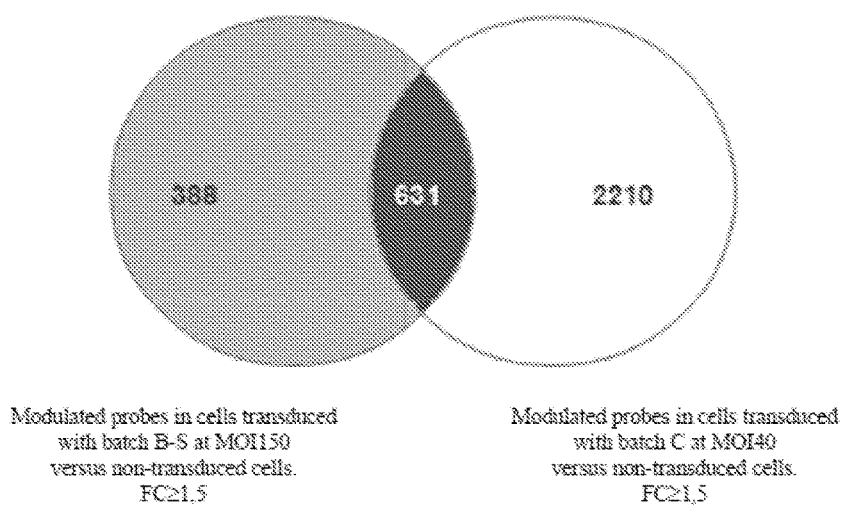

FIG. 10. Venn diagram: Modulated probes in cells transduced with batch B obtained with serum (B-S) at MOI 150 vs non-transduced cells and modulated probes in cells transduced with batch B obtained with serum (B-S) at MOI 40 vs non-transduced cells. Venn diagram showing the intersection between the list of differentially expressed probes (absolute value of FC≥1.5) in cells transduced with batch B-S at MOI 150 compared to non-transduced cells, and the list of differentially expressed probes (absolute value of FC≥1.5) in cells transduced with batch B-S at MOI 40 compared to non-transduced cells.

Figures 11, 12:
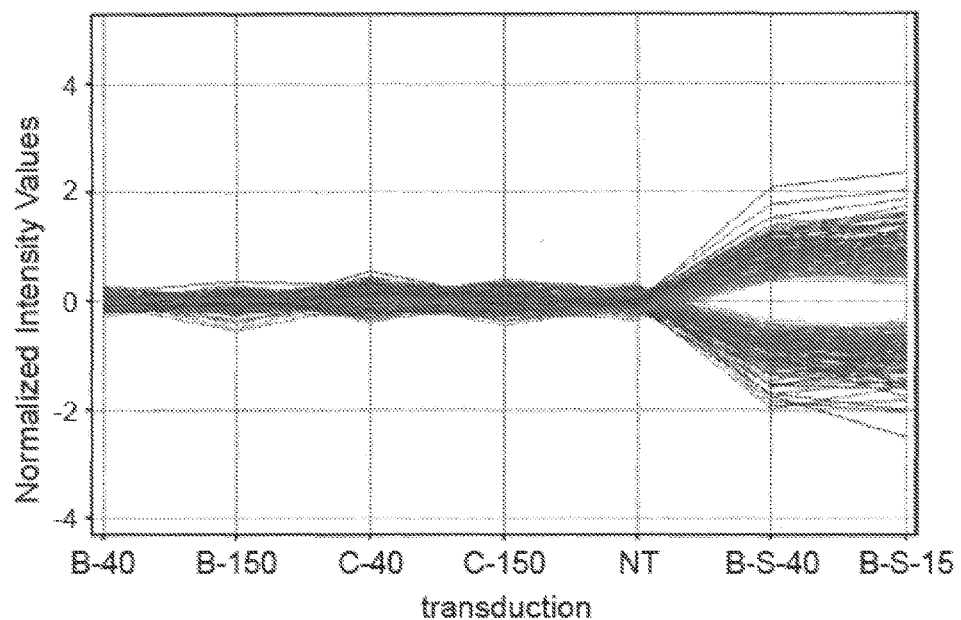

FIG. 11. Profile plot representing probes impacted in cells transduced with batch B obtained with serum (B-S) at MOI40 and 150 and not differential in cells transduced with batches B and C, at MOI40 and 150. Profile plot representing probes that were differentially expressed in cells transduced with rLV-EF1 without cDNA batch B-S at MOI 40 and MOI 150 compared to non-transduced (NT) cells, and that were not differential in cells transduced with rLV-EF1 without cDNA batch B and C transduced cells at MOI 40 and 150 compared to non-transduced cells. By "not differential", is meant that the FC absolute value is <1.3. A baseline transformation was applied on intensity values before representing data. B-40: cells transduced with batch B at MOI40. B-150: cells transduced with batch B at MOI150. C-40: cells transduced with batch C at MOI40. C-150: cells transduced with batch C at MOI 150. NT: non transduced cells. B-S-40: cells transduced with batch B obtained with serum at MOI 40. B-S-150: cells transduced with batch B obtained with serum at MOI 40.

FIG. 12. Characterization of rLV-EF1-GFP vectors batch used (B, C, B-S and UC).

Figure 13:
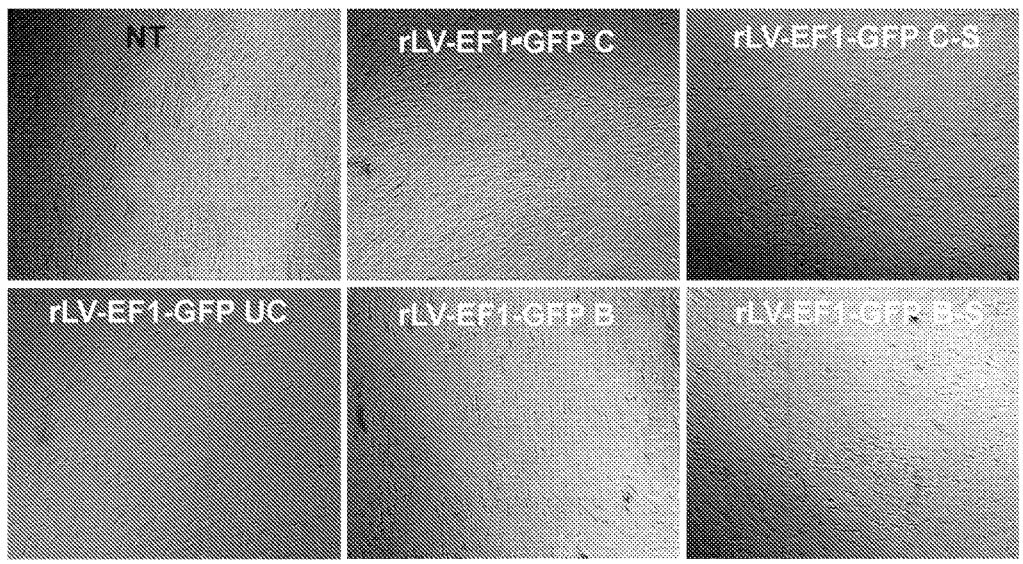
Figure 13:
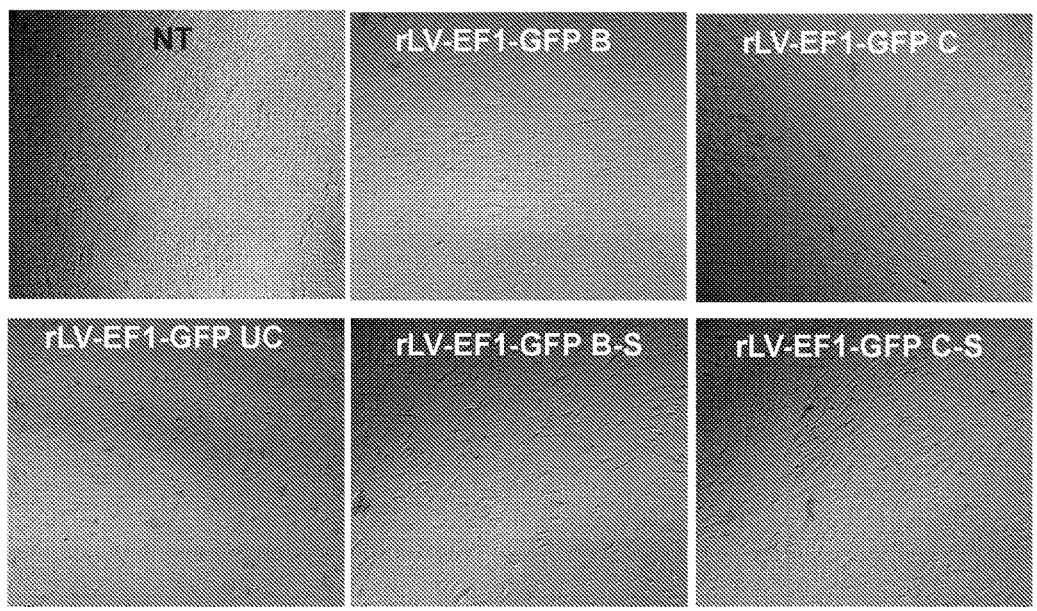

FIG. 13. Photos of Foreskin fibroblast cells transduced with rLV-EF1-GFP vectors. Cells were observed 48 hours after transduction.

Figure 14:
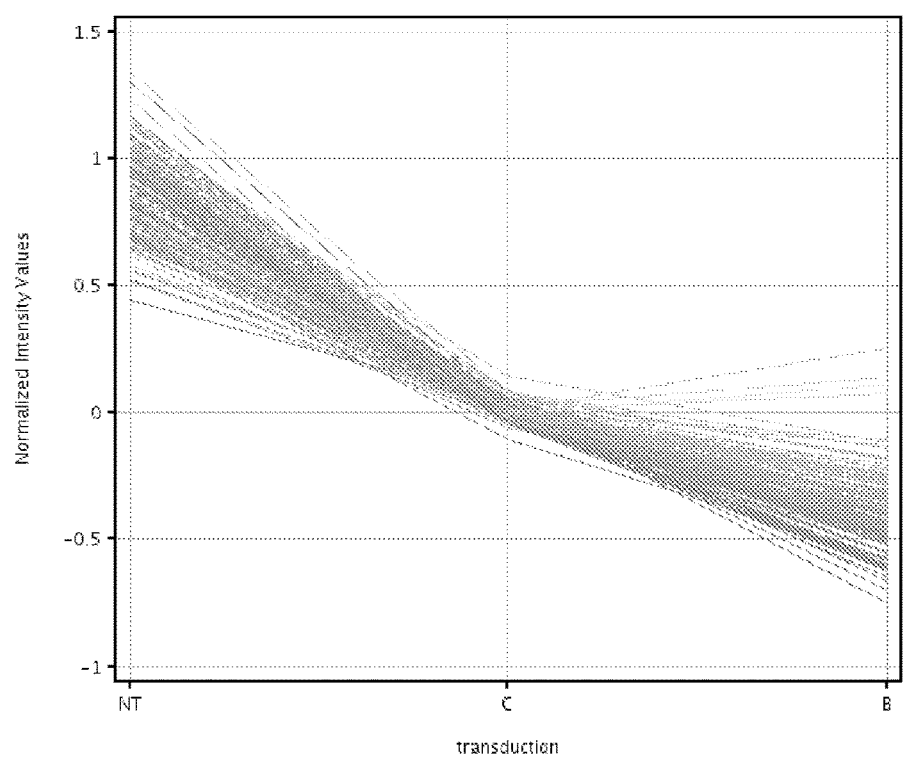

FIG. 14. Probe selected in FIG. 5 (downregulated cell cycle genes with FC<=−3 with B-MCS-MOI150 vs NT) represented in the following conditions: NT, B-GFP-MOI40, C-GFP-MOI40.

Figure 15:
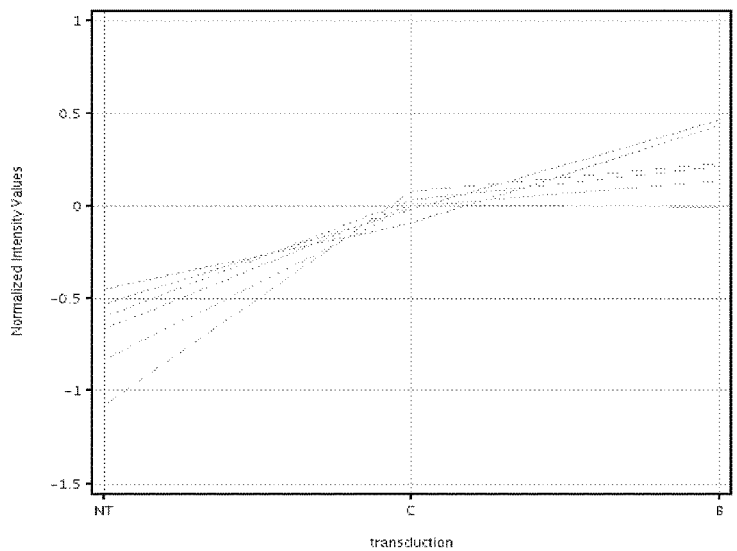

FIG. 15. Profile plot showing behavior of probes corresponding to table 3 after transduction with rLV-EF1-GFP batch B and C at MOI 40 versus Non Transduced (NT) cells.

Figure 16:
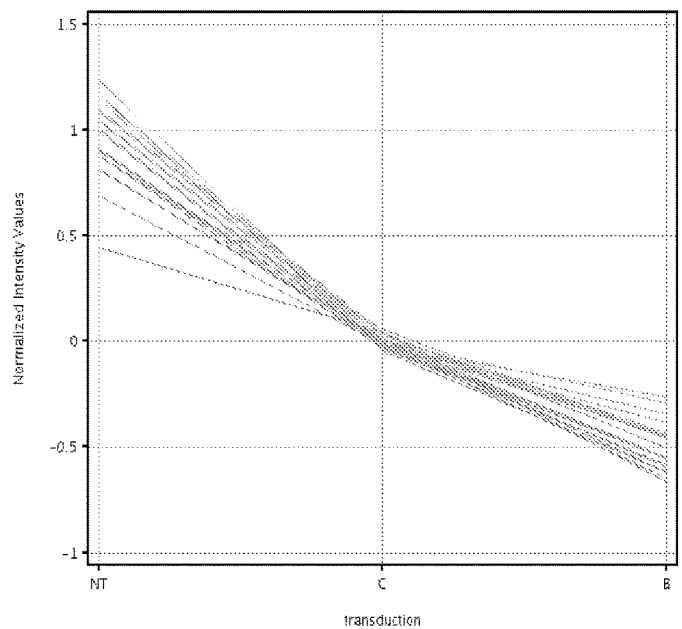

FIG. 16. Profile plot representing the probes corresponding to the 18 genes from table 4 and MKI67 after transduction with rLV-EF1-GFP vector at MOI 40.

Figure 17:
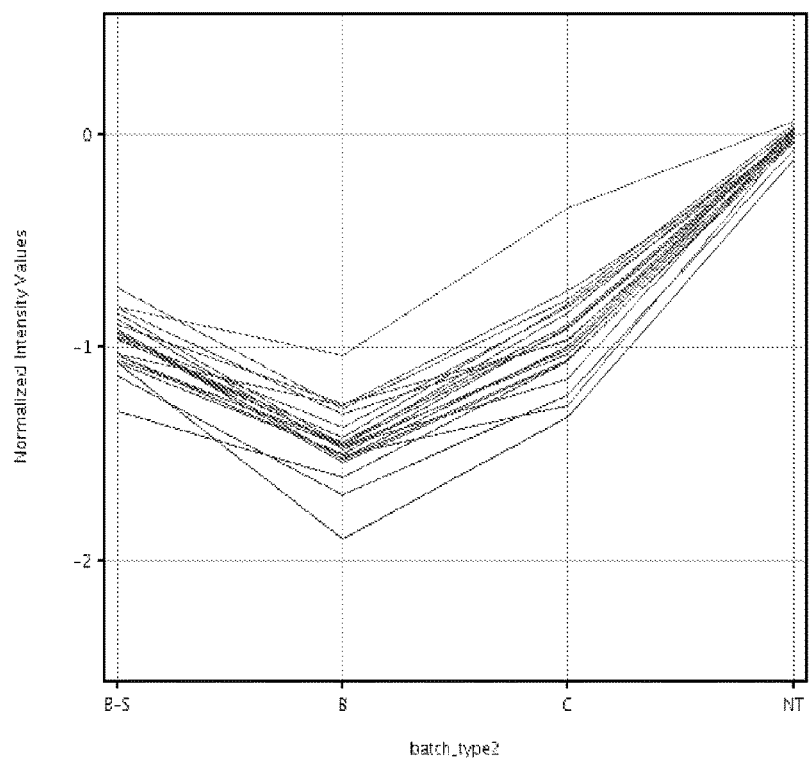
Figure 18A:
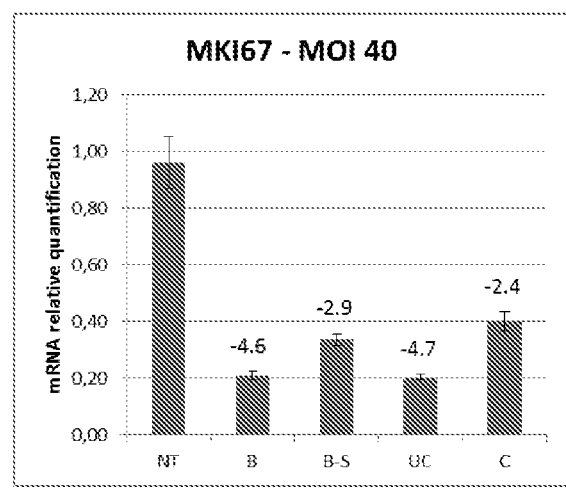
Figure 18B:
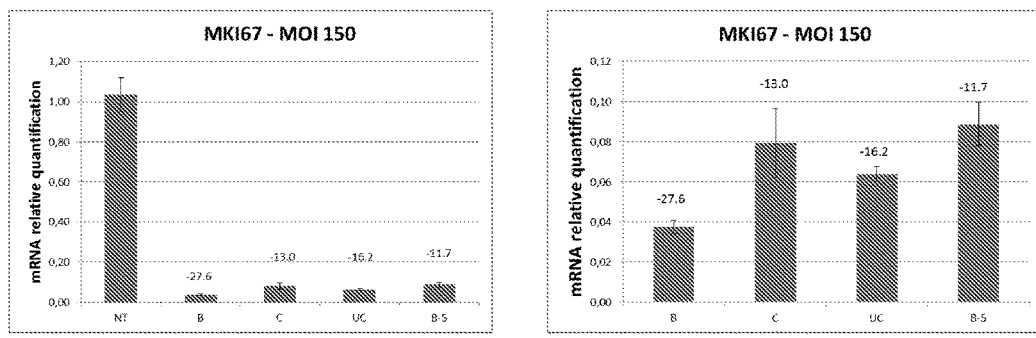
Figure 18C:
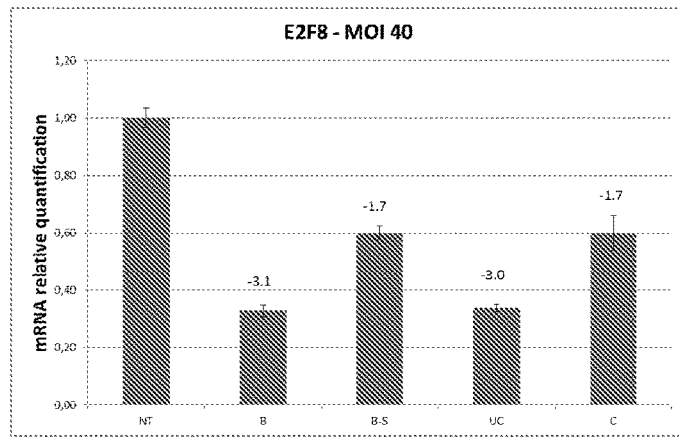
Figure 18D:
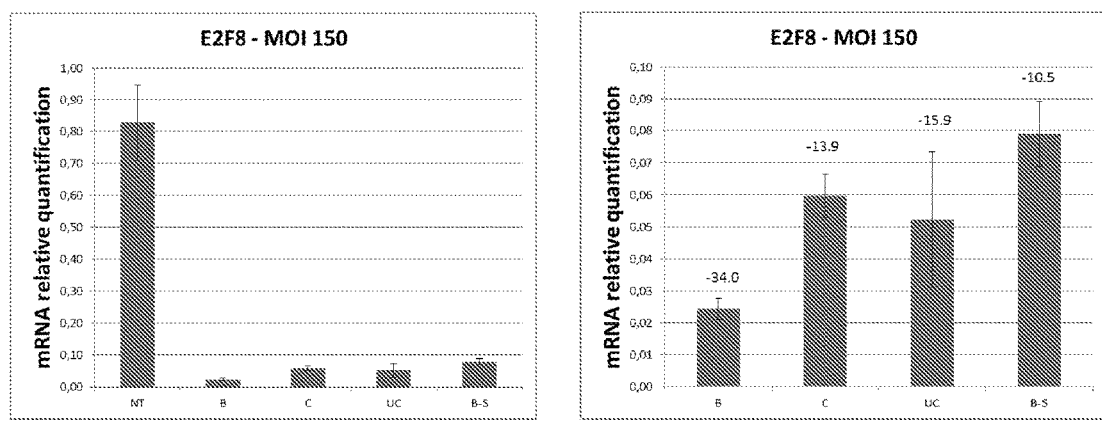

FIG. 17. Profile plot representing the 18 cell cycle genes from table 4 and MKI67 after transduction with rLV-EF1-GFP vector (B, B-S and C) at MOI 40.

FIGS. 18A-18D. Validation of some cell cycle genes as biomarkers by RT-qPCR. mRNA relative quantification values are represented as mean±SD calculated from 3 samples per condition. Fold change values for each condition compared to NT are indicated above each diagram bar when differences are significant (t-test unpaired, p-value<0.05).

Figure 19A:
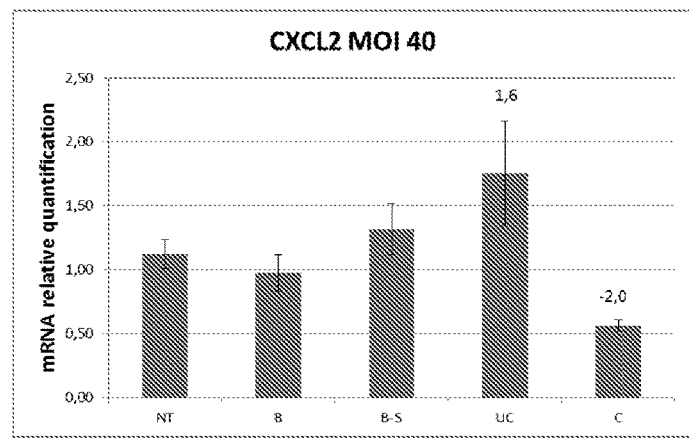
Figure 19B:
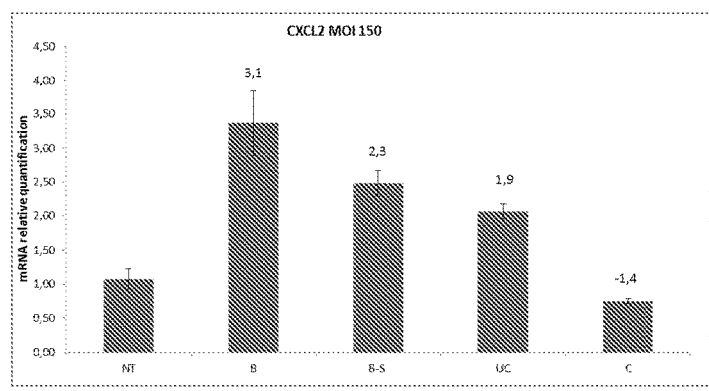
Figure 19C:
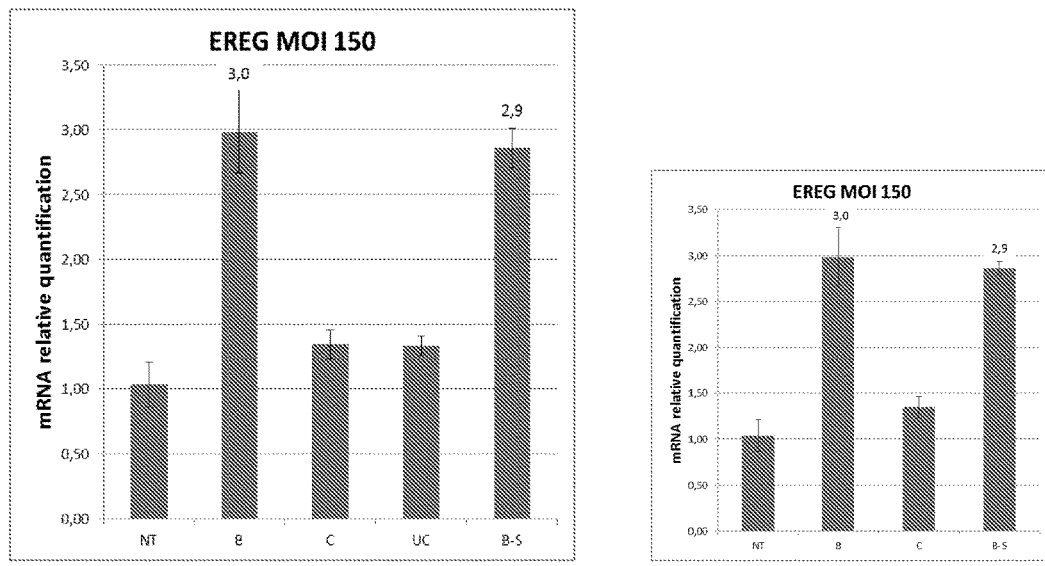

FIGS. 19A-19C. Validation of CXCL2 and EREG genes as biomarkers by RT-qPCR. mRNA relative quantification values are represented as mean±SD calculated from 3 samples per condition. Fold change values for each condition compared to NT are indicated above each diagram bar when differences are significant (t-test unpaired, p-value<0.05).

TABLES

Table 1.
Primers used for RT-qPCR validations. For each tested gene and the GAPDH reference gene (represented by their respective gene symbol), the sequences of the forward and reverse primers are shown.

| Gene symbol | Forward primer sequence | SEQ ID No. | Reverse primer sequence | SEQ ID No. |
|---|---|---|---|---|
| CENPA | TATTGGCCCTACAAGAGGCAGCAG | 22 | GCCAGTTGCACATCCTTTGGGAAG | 23 |
| E2F8 | ACGAAGTGGCAGAGGAACTTAATG | 24 | AGGCGGCTCACCATATGTAAACTC | 25 |
| MKI67 | AGCACCTGCTTGTTTGGAAGGG | 26 | ACACAACAGGAAGCTGGATACGG | 27 |
| NEK2 | AGATCCGGAGGAAGAGTGATGG | 28 | TGTTTCTCAGCTTCTGTCATGGAG | 29 |
| AURKB | TGAGAGTGCATCACACAACGAGAC | 30 | GGGAACTTTAGGTCCACCTTGACG | 31 |
| GADPH | GAGTCAACGGATTTGGTCGT | 32 | GACAAGCTTCCCGTTCTCAG | 33 |

Table 2.
Cell cycle genes sorted by increasing Fold Change. Cell cycle genes downregulated in cells transduced with rLV-EF1 without cDNA batch B and batch C at MOI 150 compared to non-transduced cells. (1) HUGO gene symbol (2) Gene description from NCBI (National Center for Biotechnology Information) (3) Agilent Probe Identifier, (4) Nucleic sequence Accession Number from the NCBI database RefSeq RNA, (5) Gene Ontology (GO) category "M phase of mitotic cell cycle", (6) GO "G1 phase" category, (7) GO "G2 phase" category, (8) GO "S phase" category, (9) GO "G1/S transition of mitotic cell cycle" category, (10) GO "G2/M transition of mitotic cell cycle" category, (11) GO "M/G1 transition of mitotic cell cycle" category. Genes are sorted by increasing values of Fold Change in batch B transduced cells at MOI 150 versus non-transduced cells.

| HUGO Gene Symbol (1) | Description (2) | ProbeName (3) | RefSeq Nucleic Accession (4) | RefSeq Protein Accession (5) | GO "M phase of mitotic cell cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| E2F8 | *Homo sapiens* E2F transcription factor 8 (E2F8), mRNA [NM_024680] | A_23_P35871 | NM_024680 | NP_078956 | | | | | | | |
| SPC25 | *Homo sapiens* SPC25, NDC80 kinetochore complex component, homolog (S. cerevisiae) (SPC25), mRNA [NM_020675] | A_23_P51085 | NM_020675 | NP_065726 | x | | | | | | |
| CENPA | *Homo sapiens* centromere protein A (CENPA), transcript variant 1, mRNA [NM_001809] | A_24_P413884 | NM_001809 | NP_001800 | x | | | | | | |
| ESCO2 | *Homo sapiens* establishment of cohesion 1 homolog 2 (S. cerevisiae) (ESCO2), mRNA [NM_001017420] | A_24_P323598; A_33_P3326210 | NM_001017420 | NP_001017420 | | | | | | | |
| NCAPG | *Homo sapiens* non-SMC condensin I complex, subunit G (NCAPG), mRNA [NM_022346] | A_33_P3230254 | NM_022346 | NP_071741 | x | | | | | | |
| TTK | *Homo sapiens* TTK protein kinase (TTK), transcript variant 1, mRNA [NM_003318] | A_23_P259586 | NM_003318 | NP_003309 | | | | | | | |
| NEK2 | *Homo sapiens* NIMA (never in mitosis gene a)-related kinase 2 (NEK2), mRNA [NM_002497] | A_24_P319613; A_23_P35219 | NM_002497 | NP_002488 | | | | | | x | |
| AURKB | *Homo sapiens* aurora kinase B (AURKB), mRNA [NM_004217] | A_23_P130182 | NM_004217 | NP_004208 | x | | | | | | |
| CDC2 | *Homo sapiens* cell division cycle 2, G1 to S and G2 to M (CDC2), transcript variant 1, mRNA [NM_001786] | A_23_P138507 | NM_001786 | NP_001777 | x | | | | x | x | |
| DLGAP5 | *Homo sapiens* discs, large (Drosophila) | A_23_P88331 | NM_014750 | NP_055565 | x | | | | | | |

-continued

| HUGO Gene Symbol (1) | Description (2) | ProbeName (3) | RefSeq Nucleic Accession (4) | RefSeq Protein Accession (5) | GO "M phase of mitotic cell cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| | homolog-associated protein 5 (DLGAP5), transcript variant 1, mRNA [NM_014750] | | | | | | | | | | |
| E2F2 | Homo sapiens E2F transcription factor 2 (E2F2), mRNA [NM_004091] | A_23_P408955 | NM_004091 | NP_004082 | | x | | | | | |
| CENPF | Homo sapiens centromere protein F, 350/400ka (mitosin) (CENPF), mRNA [NM_016143] | A_23_P401; A_24_P96780 | NM_016343 | NP_057427 | x | | x | | | | |
| NUSAP1 | Homo sapiens nucleolar and spindle associated protein 1 (NUSAP1), transcript variant 1, mRNA [NM_016359] | A_33_P3350488 | NM_016359 | NP_057443 | x | | | | | | |
| NUF2 | Homo sapiens NUF2, NDC80 kinetochore complex component, homolog (S. cerevisiae) (NUF2), transcript variant 1, mRNA [NM_145697] | A_23_P74349 | NM_145697 | NP_663735 | x | | | | | | |
| TOP2A | Homo sapiens topoisomerase (DNA) II alpha 170kDa (TOP2A), mRNA [NM_001067] | A_23_P118834 | NM_001067 | NP_001058 | | | | | | x | |
| KIFC1 | Homo sapiens kinesin family member C1 (KIFC1), mRNA [NM_002263] | A_23_P133956 | NM_002263 | NP_002254 | x | | | | | | |
| SGOL1 | Homo sapiens shugoshin-like 1 (S. pombe) (SGOL1), transcript variant A2, mRNA [NM_001012410] | A_23_P29723 | NM_001012410 | NP_001012410 | x | | | | | | |
| CDC25C | Homo sapiens cell division cycle 25 homolog C (S. pombe) (CDC25C), transcript variant 1, mRNA [NM_01790] | A_23_P70249 | NM_001790 | NP_001781 | x | x | | | | x | |

-continued

| HUGO Gene Symbol (1) | Description (2) | ProbeName (3) | RefSeq Nucleic Acid Accession (4) | RefSeq Protein Accession (5) | GO "M phase of mitotic cell cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| KIF2C | Homo sapiens kinesin family member 2C (KIF2C), mRNA [NM_006845] | A_23_P34788 | NM_006845 | NP_006836 | x | | | | | | |
| HJURP | Homo sapiens Holliday junction recognition protein (HJURP), mRNA [NM_018410] | A_33_P3807062 | NM_018410 | NP_060880 | | | | | | | |
| SKA1 | Homo sapiens spindle and kinetochore associated complex subunit 1 (SKA1), transcript variant 1, mRNA [NM_001039535] | A_24_P322354 | NM_001039535 | NP_001034624 | x | | | | | | |
| MKI67 | Homo sapiens antigen identified by monoclonal antibody Ki-67 (MKI67), transcript variant 1, mRNA [NM_002417] | A_24_P346855; A_33_P3374205; A_33_P3374210 | NM_002417 | NP_002408 | | | | | | | |
| FAM83D | Homo sapiens family with sequence similarity 83, member D (FAM83D), mRNA [NM_030919] | A_23_P323751 | NM_030919 | NP_112181 | x | | | | | | |
| CEP55 | Homo sapiens centrosomal protein 55kDa (CEP55), transcript variant 1, mRNA [NM_018131] | A_23_P115872; A_33_P3291831 | NM_018131 | NP_060601 | x | | | | | | |
| KIF20A | Homo sapiens kinesin family member 20A (KIF20A), mRNA [NM_005733] | A_23_P256956 | NM_005733 | NP_005724 | x | | | | | | |
| PBK | Homo sapiens PDZ binding kinase (PBK), mRNA [NM_018492] | A_32_P62997 | NM_018492 | NP_060962 | x | | | | | | |
| NDC80 | Homo sapiens NDC80 homolog, kinetochore complex component (S. cerevisiae) (NDC80), mRNA [NM_006101] | A_23_P50108 | NM_006101 | NP_006092 | x | | | | | | |
| SKA3 | Homo sapiens spindle and kinetochore associated complex subunit 3 (SKA3), transcript variant 1, mRNA [NM_145061] | A_33_P3216008 | NM_145061 | NP_659498 | x | | | | | | |

-continued

| HUGO Gene Symbol (1) | Description (2) | ProbeName (3) | RefSeq Nucleic Acession (4) | RefSeq Protein Accession (5) | GO "M phase of mitotic cell cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| CDCA3 | *Homo sapiens* cell division cycle associated 3 (CDCA3), mRNA [NM_031299] | A_24_P218979 | NM_031299 | NP_112589 | x | | | | | | |
| BUB1 | *Homo sapiens* budding uninhibited by benzimidazoles 1 homolog (yeast) (BUB1), mRNA [NM_004336] | A_23_P124417 | NM_004336 | NP_004327 | x | | | | | | |
| ASPM | *Homo sapiens* asp (abnormal spindle) homolog, microcephaly associated (Drosophila) (ASPM), mRNA [NM_018136] | A_33_P3288159; A_23_P52017 | NM_018136 | NP_060606 | x | | | | | | |
| IQGAP3 | *Homo sapiens* IQ motif containing GTPase activating protein 3 (IQGAP3), mRNA [NM_178229] | A_33_P3321293 | NM_178229 | NP_839943 | | | | | x | | |
| PLK1 | *Homo sapiens* polo-like kinase 1 (Drosophila) (PLK1), mRNA [NM_005030] | A_23_P118174; A_33_P3298387 | NM_005030 | NP_005021 | x | | | | | x | |
| | Kinetochore protein Spc24 (hSpc24) [Source: UniProtKB/Swiss-Prot; Acc: Q8NBT2] [ENST00000293743] | A_24_P314571 | | #N/A | x | | | | | | |
| ANLN | *Homo sapiens* anillin, actin binding protein (ANLN), mRNA [NM_018685] | A_23_P356684 | NM_018685 | NP_061155 | x | | | | | | |
| CDCA8 | *Homo sapiens* cell division cycle associated 8 (CDCA8), mRNA [NM_018101] | A_23_P375 | NM_018101 | NP_060571 | x | | | | | | |
| GTSE1 | *Homo sapiens* G-2 and S-phase expressed 1 (GTSE1), mRNA [NM_016426] | A_23_P57588 | NM_016426 | NP_057510 | | | x | | | | |
| PRC1 | *Homo sapiens* protein regulator of cytokinesis 1 (PRC1), transcript variant 1, mRNA [NM_003981] | A_23_P206059 | NM_003981 | NP_003972 | | | | | | | |
| CDC45L | *Homo sapiens* CDC45 cell division | A_23_P57379 | NM_003504 | NP_003495 | | | | x | x | | x |

-continued

| HUGO Gene Symbol (1) | Description (2) | ProbeName (3) | RefSeq Nucleic Acid Accession (4) | RefSeq Protein Accession (5) | GO "M phase of mitotic cell cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| | cycle 45-like (*S. cerevisiae*) (CDC45L), mRNA [NM_003504] | | | | | | | | | | |
| BUB1B | *Homo sapiens* budding uninhibited by benzimidazoles 1 homolog beta (yeast) (BUB1B), mRNA [NM_001211] | A_23_P163481 | NM_001211 | NP_001202 | x | | | | | | |
| CDKN3 | *Homo sapiens* cyclin-dependent kinase inhibitor 3 (CDKN3), transcript variant 1, mRNA [NM_005192] | A_33_P3307903; A_23_P48669 | NM_005192 | NP_005183 | | | | | x | | |
| CCNB2 | *Homo sapiens* cyclin B2 (CCNB2), mRNA [NM_004701] | A_23_P65757 | NM_004701 | NP_004692 | x | | | | | x | |
| RAD54L | *Homo sapiens* RAD54-like (*S. cerevisiae*) (RAD54L), transcript variant 1, mRNA [NM_003579] | A_23_P74115 | NM_003579 | NP_003570 | | | | | | | |
| OIP5 | *Homo sapiens* Opa interacting protein 5 (OIP5), mRNA [NM_007280] | A_23_P379614 | NM_007280 | NP_009211 | x | | | | | | |
| SGOL1 | *Homo sapiens* shugoshin-like 1 (*S. pombe*) (SGOL1), transcript variant A1, mRNA [NM_001012409] | A_24_P225970 | NM_001012409 | NP_001012409 | x | | | | | | |
| MND1 | *Homo sapiens* meiotic nuclear divisions 1 homolog (*S. cerevisiae*) (MND1), mRNA [NM_032117] | A_23_P133123 | NM_032117 | NP_115493 | | | | | | | |
| RRM2 | *Homo sapiens* ribonucleotide reductase M2 (RRM2), transcript variant 2, mRNA [NM_001034] | A_24_P225616 | NM_001034 | NP_001025 | | | | | x | | |
| UBE2C | *Homo sapiens* ubiquitin-conjugating enzyme E2C (UBE2C), | A_24_P297539 | NM_181803 | NP_861519 | x | | | | | | |

| HUGO Gene Symbol (1) | Description (2) | ProbeName (3) | RefSeq Nucleic Accession (4) | RefSeq Protein Accession (5) | GO "M phase of mitotic cell cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| KIF11 | *Homo sapiens* kinesin family member 11 (KIF11), mRNA [NM_004523] transcript variant 6, mRNA [NM_181803] | A_24_P227091 | NM_004523 | NP_004514 | x | | | | | | |
| CASC5 | *Homo sapiens* cancer susceptibility candidate 5 (CASC5), transcript variant 1, mRNA [NM_170589] | A_23_P100127; A_33_P3213342 | NM_170589 | NP_733468 | x | | | | | | |
| SPC24 | *Homo sapiens* SPC24, NDC80 kinetochore complex component, homolog (*S. cerevisiae*) (SPC24), mRNA [NM_182513] | A_33_P3376116 | NM_182513 | NP_872319 | x | | | | | | |
| CDCA2 | *Homo sapiens* cell division cycle associated 2 (CDCA2), mRNA [NM_152562] | A_23_P385861 | NM_152562 | NP_689775 | x | | | | | | |
| CDC20 | *Homo sapiens* cell division cycle 20 homolog (*S. cerevisiae*) (CDC20), mRNA [NM_001255] | A_23_P149200 | NM_001255 | NP_001246 | x | | | | | | |
| CCNA2 | *Homo sapiens* cyclin A2 (CCNA2), mRNA [NM_001237] | A_23_P8321 | NM_001237 | NP_001228 | x | | | | | x | |
| MLF1IP | *Homo sapiens* MLF1 interacting protein (MLF1IP), mRNA [NM_024629] | A_23_P254733 | NM_024629 | NP_078905 | x | | | | | | |
| BIRC5 | *Homo sapiens* baculoviral IAP repeat-containing 5 (BIRC5), transcript variant 3, mRNA [NM_001012271] | A_23_P118815 | NM_001012271 | NP_001012271 | x | | | | | x | |
| TACC3 | *Homo sapiens* transforming, acidic coiled-coil containing protein 3 (TACC3), mRNA [NM_006342] | A_23_P212844 | NM_006342 | NP_006333 | | | | | | | |
| CENPE | *Homo sapiens* centromere protein E, 312kDa | A_23_P253524 | NM_001813 | NP_001804 | x | | | | | | |

-continued

| HUGO Gene Symbol (1) | Description (2) | ProbeName (3) | RefSeq Nucleic Accession (4) | RefSeq Protein Accession (5) | GO "M phase of mitotic cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| | (CENPE), mRNA [NM_001813] | | | | | | | | | | |
| KIF15 | Homo sapiens kinesin family member 15 (KIF15), mRNA [NM_020242] | A_23_P80902 | NM_020242 | NP_064627 | x | | | | | | |
| CDCA5 | Homo sapiens cell division cycle associated 5 (CDCA5), mRNA [NM_080668] | A_23_P104651 | NM_080668 | NP_542399 | x | | | | x | | |
| SPAG5 | Homo sapiens sperm associated antigen 5 (SPAG5), mRNA [NM_006461] | A_23_P89509 | NM_006461 | NP_006452 | x | | | | | | |
| CCNB1 | Homo sapiens cyclin B1 (CCNB1), mRNA [NM_031966] | A_23_P122197; A_33_P3401621 | NM_031966 | NP_114172 | x | | | | x | x | |
| BLM | Homo sapiens Bloom syndrome, RecQ helicase-like (BLM), mRNA [NM_000057] | A_23_P88630 | NM_000057 | NP_000048 | | | x | | | | |
| CENPM | Homo sapiens centromere protein M (CENPM), transcript variant 1, mRNA [NM_024053] | A_33_P3387831 | NM_024053 | NP_076958 | x | | | | | | |
| CLSPN | Homo sapiens claspin homolog (Xenopus laevis) (CLSPN), mRNA [NM_022111] | A_23_P126212 | NM_022111 | NP_071394 | | | | | | | |
| TPX2 | Homo sapiens TPX2, microtubule-associated, homolog (Xenopus laevis) (TPX2), mRNA [NM_012112] | A_23_P68610 | NM_012112 | NP_036244 | x | | | | | | |
| GINS2 | Homo sapiens GINS complex subunit 2 (Psf2 homolog) (GINS2), mRNA [NM_016095] | A_23_P118246 | NM_016095 | NP_057179 | | | | x | | | |
| MAD2L1 | Homo sapiens MAD2 mitotic arrest deficient-like 1 (yeast) (MAD2L1), mRNA [NM_002358] | A_23_P92441 | NM_002358 | NP_002349 | x | | | | | | |
| RACGAP1 | Homo sapiens Rac GTPase activating protein 1 (RACGAP1), | A_32_P186474 | NM_013277 | NP_037409 | | | | | | | |

-continued

| HUGO Gene Symbol (1) | Description (2) | ProbeName (3) | RefSeq Nucleic Accession (4) | RefSeq Protein Accession (5) | GO "M phase of mitotic cell cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| ERCC6L | transcript variant 1, mRNA [NM_013277] Homo sapiens excision repair cross-complementing rodent repair deficiency, complementation group 6-like (ERCC6L), mRNA [NM_017669] | A_23_P96325 | NM_017669 | NP_060139 | x | | | | | | |
| FANCD2 | Homo sapiens Fanconi anemia, complementation group D2 (FANCD2), transcript variant 2, mRNA [NM_001018115] | A_33_P3257808; A_23_P143994 | NM_001018115 | NP_001018125 | | | | | | | |
| PKMYT1 | Homo sapiens protein kinase, membrane associated tyrosine/threonine 1 (PKMYT1), transcript variant 2, mRNA [NM_182687] | A_33_P3397443 | NM_182687 | NP_872629 | x | | | | x | x | |
| CENPM | Homo sapiens centromere protein M (CENPM), transcript variant 2, mRNA [NM_001002876] | A_24_P399888 | NM_001002876 | NP_001002876 | x | | | | | | |
| CENPH | Homo sapiens centromere protein H (CENPH), mRNA [NM_022909] | A_23_P110802 | NM_022909 | NP_075060 | x | | | | | | |
| ORC1L | Homo sapiens origin recognition complex, subunit 1-like (yeast) (ORC1L), mRNA [NM_004153] | A_23_P45799 | NM_004153 | NP_004144 | | | | x | x | | x |
| CCNE2 | Homo sapiens cyclin E2 (CCNE2), mRNA [NM_057749] | A_33_P3247022; A_33_P3217819 | NM_057749 | NP_477097 | | | | | x | | |
| TRIP13 | Homo sapiens thyroid hormone receptor interactor 13(TRIP13), transcript variant 1, mRNA [NM_004237] | A_33_P3339212 | NM_004237 | NP_004228 | | | | | | | |
| NCAPG2 | Homo sapiens non-SMC condensin II complex, | A_33_P3659876 | NM_017760 | NP_060230 | x | | | | | | |

-continued

| HUGO Gene Symbol (1) | Description (2) | ProbeName (3) | RefSeq Nucleic Acession (4) | RefSeq Protein Accession (5) | GO "M phase of mitotic cell cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| | subunit G2 (NCAPG2), mRNA [NM_017760] | | | | | | | | | | |
| C11orf82 | Homo sapiens chromosome 11 open reading frame 82 (C11orf82), mRNA [NM_145018] | A_23_P429491 | NM_145018 | NP_659455 | | | | | | | |
| CENPK | Homo sapiens centromere protein K (CENPK), mRNA [NM_022145] | A_23_P155989 | NM_022145 | NP_071428 | x | | | | | | |
| RAD51 | Homo sapiens RAD51 homolog (RecA homolog, E. coli) (S. cerevisiae) (RAD51), transcript variant 1, mRNA [NM_002875] | A_23_P8731 | NM_002875 | NP_002866 | | | | | | | |
| CDT1 | Homo sapiens chromatin licensing and DNA replication factor 1 (CDT1), mRNA [NM_030928] | A_33_P3386262 | NM_030928 | NP_112190 | | | | x | x | | |
| E2F1 | Homo sapiens E2F transcription factor 1 (E2F1), mRNA [NM_005225] | A_23_P80032 | NM_005225 | NP_005216 | | x | x | | x | | |
| GAS2L3 | Homo sapiens growth arrest-specific 2 like 3 (GAS2L3), mRNA [NM_174942] | A_32_P189204 | NM_174942 | NP_777602 | | | | | | | |
| SGOL2 | Homo sapiens shugoshin-like 2 (S. pombe) (SGOL2), transcript variant 1, mRNA [NM_152524] | A_23_P411335 | NM_152524 | NP_689737 | x | | | | | | x |
| BRCA1 | Homo sapiens breast cancer 1, early onset (BRCA1), transcript variant 2, mRNA [NM_007300] | A_23_P207400 | NM_007300 | NP_009231 | | | | | | | |
| BRCA2 | Homo sapiens breast cancer 2, early onset (BRCA2), mRNA [NM_000059] | A_23_P99452 | NM_000059 | NP_000050 | | | | | | | |
| FANCI | Homo sapiens Fanconi anemia, complementation group I (FANCI), | A_32_P95729 | NM_018193 | NP_060663 | | | | | | | |

-continued

| HUGO Gene Symbol (1) | Description (2) | ProbeName (3) | RefSeq Nucleic Acid Accession (4) | RefSeq Protein Accession (5) | GO "M phase of mitotic cell cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| POLE2 | transcript variant 2, mRNA [NM_018193] Homo sapiens polymerase (DNA directed), epsilon 2 (p59 subunit) (POLE2), mRNA [NM_002692] | A_23_P163099 | NM_002692 | NP_002683 | | | | x | | | x |
| PTTG1 | Homo sapiens pituitary tumor-transforming 1 (PTTG1), mRNA [NM_004219] | A_23_P7636 | NM_004219 | NP_004210 | x | | | | | | |
| KIF23 | Homo sapiens kinesin family member 23 (KIF23), transcript variant 1, mRNA[NM_138555] | A_33_P3311755; A_23_P48835 | NM_138555 | NP_612565 | | | | | | | |
| TRIP13 | Homo sapiens thyroid hormone receptor interactor 13(TRIP13), transcript variant 2, mRNA [NM_001166260] | A_33_P3407256 | NM_001166260 | NP_001159732 | | | | | | | |
| EXO1 | Homo sapiens exonuclease 1 (EXO1), transcript variant 3, mRNA [NM_003686] | A_23_P23303 | NM_003686 | NP_003677 | | | | | | | |
| ZWINT | Homo sapiens ZW10 interactor (ZWINT), transcript variant 2, mRNA [NM_032997] | A_33_P3212994; A_23_P63789 | NM_032997 | NP_127490 | | | | | | | |
| KIF22 | Homo sapiens kinesin family member 22 (KIF22), mRNA [NM_007317] | A_23_P54622; A_33_P3350634 | NM_007317 | NP_015556 | x | | | | | | |
| PRIM1 | Homo sapiens primase, DNA, polypeptide 1 (49kDa) (PRIM1), mRNA [NM_000946] | A_23_P25019 | NM_000946 | NP_000937 | | | | x | x | | |
| FANCA | Homo sapiens Fanconi anemia, complementation group A (FANCA), transcript variant 1, mRNA [NM_000135] | A_23_P206441 | NM_000135 | NP_000126 | | | | | | | |
| GINS4 | Homo sapiens GINS complex subunit 4 (Sld5 homolog) (GINS4), mRNA [NM_032336] | A_33_P3340040 | NM_032336 | NP_115712 | | | | x | | | |

-continued

| HUGO Gene Symbol (1) | Description (2) | ProbeName (3) | RefSeq Nucleic Accession (4) | RefSeq Protein Accession (5) | GO "M phase of mitotic cell cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| CKS1B | *Homo sapiens* CDC28 protein kinase regulatory subunit 1B (CKS1B), transcript variant 1, mRNA [NM_001826] | A_32_P06698; A_23_P45917 | NM_001826 | NP_001817 | | | | x | x | | |
| CENPI | *Homo sapiens* centromere protein I (CENPI), mRNA [NM_006733] | A_24_P419132; A_33_P3221313 | NM_006733 | NP_006724 | | | | | | | |
| MCM5 | *Homo sapiens* minichromosome maintenance complex component 5 (MCM5), mRNA [NM_006739] | A_33_P3284951; A_23_P132277 | NM_006739 | NP_006730 | | | | x | x | | x |
| FOXM1 | *Homo sapiens* forkhead box M1 (FOXM1), transcript variant 1, mRNA [NM_202002] | A_23_P151150 | NM_202002 | NP_973731 | | | | | x | | |
| FBXO5 | *Homo sapiens* F-box protein 5 (FBXO5), transcript variant 2, mRNA [NM_001142522] | A_33_P3384871 | NM_001142522 | NP_001135994 | x | | | | | | |
| MCM7 | *Homo sapiens* minichromosome maintenance complex component 7 (MCM7), transcript variant 2, mRNA [NM_182776] | A_23_P93690 | NM_182776 | NP_877577 | | | | x | x | | x |
| ORC6L | *Homo sapiens* origin recognition complex, subunit 6 like (yeast) (ORC6L), mRNA [NM_014321] | A_23_P100344 | NM_014321 | NP_055136 | | | | x | x | | |
| STMN1 | *Homo sapiens* stathmin 1 (STMN1), transcript variant 1, mRNA [NM_203401] | A_33_P3317523 | NM_203401 | NP_981946 | | | | | | | x |
| AURKA | *Homo sapiens* aurora kinase A (AURKA), transcript variant 1, mRNA [NM_198433] | A_23_P131866 | NM_198433 | NP_940835 | x | | | | | | |
| KIF20B | *Homo sapiens* kinesin family member 20B (KIF20B), mRNA [NM_016195] | A_23_P75071; A_33_P3215239 | NM_016195 | NP_057279 | x | | | | | | |

-continued

| HUGO Gene Symbol (1) | Description (2) | ProbeName (3) | RefSeq Nucleic Accession (4) | RefSeq Protein Accession (5) | GO "M phase of mitotic cell cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| CKS2 | Homo sapiens CDC28 protein kinase regulatory subunit 2 (CKS2), mRNA [NM_001827] | A_23_P71727 | NM_001827 | NP_001818 |  |  |  |  |  |  |  |
| CIT | Homo sapiens citron (rho-interacting, serine/threonine kinase 21) (CIT), mRNA [NM_007174] | A_33_P3312301; A_23_P420551 | NM_007174 | NP_009105 | x |  |  |  |  |  |  |
| GINS1 | Homo sapiens GINS complex subunit 1 (Psf1 homolog) (GINS1), mRNA [NM_021067] | A_33_P3340025 | NM_021067 | NP_066545 |  |  |  | x |  |  |  |
| PSRC1 | Homo sapiens proline/serine-rich coiled-coil 1 (PSRC1), transcript variant 1, mRNA [NM_032636] | A_23_P46539 | NM_032636 | NP_116025 | x |  |  |  |  |  |  |
| FEN1 | Homo sapiens flap structure-specific endonuclease 1 (FEN1), mRNA [NM_004111] | A_24_P84898 | NM_004111 | NP_004102 |  |  |  | x |  |  |  |
| CHTF18 | Homo sapiens CTF18, chromosome transmission fidelity factor 18 homolog (S. cerevisiae) (CHTF18), mRNA [NM_022092] | A_23_P354297 | NM_022092 | NP_071375 |  |  |  |  |  |  |  |
| HAUS8 | Homo sapiens HAUS augmin-like complex, subunit 8 (HAUS8), transcript variant 1, mRNA [NM_033417] | A_23_P141965; A_33_P3242124 | NM_033417 | NP_219485 | x |  |  |  |  |  |  |
| SMC4 | Homo sapiens structural maintenance of chromosomes 4 (SMC4), transcript variant 1, mRNA [NM_005496] | A_33_P3716128; A_33_P3248519 | NM_005496 | NP_005487 | x |  |  |  |  |  |  |
| MCM7 | Homo sapiens minichromosome maintenance complex component 7 (MCM7), transcript variant 1, mRNA [NM_005916] | A_33_P3258223 | NM_005916 | NP_005907 |  |  |  | x | x |  | x |

-continued

| HUGO Gene Symbol (1) | Description (2) | ProbeName (3) | RefSeq Nucleic Accession (4) | RefSeq Protein Accession (5) | GO "M phase of mitotic cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| MCM2 | Homo sapiens minichromosome maintenance complex component 2 (MCM2), mRNA [NM_004526] | A_32_P103633 | NM_004526 | NP_004517 | | | | x | x | | x |
| UHRF1 | Homo sapiens ubiquitin-like with PHD and ring finger domains 1 (UHRF1), transcript variant 2, mRNA [NM_013282] | A_23_P208880; A_33_P3379454 | NM_013282 | NP_037414 | | | | | | | |
| H2AFX | Homo sapiens H2A histone family, member X (H2AFX), mRNA [NM_002105] | A_24_P38895 | NM_002105 | NP_002096 | | | | | | | |
| TIMELESS | Homo sapiens timeless homolog (Drosophila) (TIMELESS), mRNA [NM_003920] | A_23_P53276 | NM_003920 | NP_003911 | x | | | | | | |
| DBF4 | Homo sapiens DBF4 homolog (S. cerevisiae) (DBF4), mRNA [NM_006716] | A_33_P3413523 | NM_006716 | NP_006707 | | | | | x | | x |
| CENPN | Homo sapiens centromere protein N (CENPN), transcript variant 3, mRNA [NM_018455] | A_23_P88740 | NM_018455 | NP_060925 | x | | | | | | |
| FANCA | Homo sapiens Fanconi anemia, complementation group A (FANCA), transcript variant 2, mRNA [NM_001018112] | A_33_P3286422; A_33_P3386344 | NM_001018112 | NP_001018122 | | | | | | | |
| LIN9 | Homo sapiens lin-9 homolog (C. elegans) (LIN9), mRNA [NM_173083] | A_32_P233304 | NM_173083 | NP_775106 | | | | | | | |
| HELLS | Homo sapiens helicase, lymphoid-specific (HELLS), mRNA [NM_018063] | A_23_P12816; A_33_P3258117 | NM_018063 | NP_060533 | x | | | | | | |
| CKAP2 | Homo sapiens cytoskeleton associated protein 2 (CKAP2), | A_23_P151405; A_24_P99090 | NM_018204 | NP_060674 | | | | | | | |

| HUGO Gene Symbol (1) | Description (2) | ProbeName (3) | RefSeq Nucleic Accession (4) | RefSeq Protein Accession (5) | GO "M phase of mitotic cell cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| NCAPD2 | Homo sapiens non-SMC condensin I complex, subunit D2 (NCAPD2), transcript variant 1, mRNA [NM_018204] | A_33_P3303385; A_23_P25293 | NM_014865 | NP_055680 | x | | | | | | |
| RFC3 | Homo sapiens replication factor C (activator 1) 3, 38kDa (RFC3), transcript variant 1, mRNA [NM_002915] | A_23_P14193 | NM_002915 | NP_002906 | | | | x | | | |
| TYMS | Homo sapiens thymidylate synthetase (TYMS), mRNA [NM_001071] | A_23_P50096 | NM_001071 | NP_001062 | | | | | x | | |
| HIST1H3F | Homo sapiens histone cluster 1, H3f (HIST1H3F), mRNA [NM_021018] | A_23_P30799 | NM_021018 | NP_066298 | | | | x | | | |
| KIF18A | Homo sapiens kinesin family member 18A (KIF18A), mRNA [NM_031217] | A_33_P3242649 | NM_031217 | NP_112494 | x | | | | | | |
| BARD1 | Homo sapiens BRCA1 associated RING domain 1 (BARD1), mRNA [NM_000465] | A_23_P67771 | NM_000465 | NP_000456 | | | | | | | |
| SYCE2 | Homo sapiens synaptonemal complex central element protein 2 (SYCE2), mRNA [NM_001105578] | A_32_P203528 | NM_001105578 | NP_001099048 | | | | | | | |
| CDKN2C | Homo sapiens cyclin-dependent kinase inhibitor 2C (p18, inhibits CDK4) (CDKN2C), transcript variant 2, mRNA [NM_078626] | A_33_P3292540 | NM_078626 | NP_523240 | | x | | | x | | |
| CENPP | Homo sapiens centromere protein P (CENPP), mRNA [NM_001012267] | A_33_P3245321 | NM_001012267 | NP_001012267 | x | | | | | | |

| HUGO Gene Symbol (1) | Description (2) | ProbeName (3) | RefSeq Nucleic Accession (4) | RefSeq Protein Accession (5) | GO "M phase of mitotic cell cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| KNTC1 | *Homo sapiens* kinetochore associated 1 (KNTC1), mRNA [NM_014708] | A_23_P136817 | NM_014708 | NP_055523 | x | | | | | | |
| ESPL1 | *Homo sapiens* extra spindle pole bodies homolog 1 (*S. cerevisiae*) (ESPL1), mRNA [NM_012291] | A_23_P32707 | NM_012291 | NP_036423 | x | | | | | | |
| C13orf34 | *Homo sapiens* chromosome 13 open reading frame 34 (C13orf34), mRNA [NM_024808] | A_23_P25626 | NM_024808 | NP_079084 | | | | | | | |
| MCM3 | *Homo sapiens* minichromosome maintenance complex component 3 (MCM3), mRNA [NM_002388] | A_23_P7873 | NM_002388 | NP_002379 | | | | x | x | | x |
| GMNN | *Homo sapiens* geminin, DNA replication inhibitor (GMNN), mRNA [NM_015895] | A_23_P19712 | NM_015895 | NP_056979 | | | | | | | |
| SMC2 | *Homo sapiens* structural maintenance of chromosomes 2 (SMC2), transcript variant 1, mRNA [NM_001042550] | A_33_P3357322; A_33_P3378334 | NM_001042550 | NP_001036015 | x | | | | | | |
| CHAF1B | *Homo sapiens* chromatin assembly factor 1, subunit B (p60)(CHAF1B), mRNA [NM_005441] | A_23_P57306 | NM_005441 | NP_005432 | | | | | | | |
| POLA1 | *Homo sapiens* polymerase (DNA directed), alpha 1, catalytic subunit (POLA1), mRNA [NM_016937] | A_32_P1701 | NM_016937 | NP_058633 | | | | x | x | | x |
| INCENP | *Homo sapiens* inner centromere protein antigens 135/155kDa (INCENP), transcript variant 1, mRNA [NM_001040694] | A_23_P116387 | NM_001040694 | NP_001035784 | x | | | | | | |

| HUGO Gene Symbol (1) | Description (2) | ProbeName (3) | RefSeq Nucleic Accession (4) | RefSeq Protein Accession (5) | GO "M phase of mitotic cell cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| CENPO | *Homo sapiens* centromere protein O (CENPO), mRNA [NM_024322] | A_23_P50990; A_24_P276888 | NM_024322 | NP_077298 | x | | | | | | |
| MCM4 | *Homo sapiens* minichromosome maintenance complex component 4 (MCM4), transcript variant 1, mRNA [NM_005914] | A_23_P370989 | NM_005914 | NP_005905 | | | | x | x | | x |
| CENPN | *Homo sapiens* centromere protein N (CENPN), transcript variant 2, mRNA [NM_001100624] | A_33_P3387861 | NM_001100624 | NP_001094094 | x | | | | | | |
| KPNA2 | *Homo sapiens* karyopherin alpha 2 (RAG cohort 1, importin alpha 1) (KPNA2), mRNA [NM_002266] | A_23_P125265 | NM_002266 | NP_002257 | | | x | | | | |
| | Centromere protein I (CENP-I) (Interphase centromere complex protein 19) (Follicle-stimulating hormone primary response protein) (FSH primary response protein 1) (Leucine-rich primary response protein 1) [Source: UniProtKB/Swiss-Prot; Acc: Q92674] | A_33_P3340468 | | #N/A | x | | | | | | |
| MCM8 | *Homo sapiens* minichromosome maintenance complex component 8 (MCM8), transcript variant 2, mRNA [NM_182802] | A_23_P68547 | NM_182802 | NP_877954 | | | | x | x | | x |
| PSMC3IP | *Homo sapiens* PSMC3 interacting protein (PSMC3IP), transcript variant 1, mRNA [NM_013290] | A_24_P287941 | NM_013290 | NP_037422 | | | | | | | |

-continued

| HUGO Gene Symbol (1) | Description (2) | ProbeName (3) | RefSeq Nucleic Acid Accession (4) | RefSeq Protein Accession (5) | GO "M phase of mitotic cell cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| CEP110 | Homo sapiens centrosomal protein 110kDa (CEP110), mRNA [NM_007018] | A_24_P109554 | NM_007018 | NP_008949 | | | | | | x | |
| E2F7 | Homo sapiens E2F transcription factor 7 (E2F7), mRNA [NM_203394] | A_32_P210202 | NM_203394 | NP_976328 | | | | | | | |
| DTYMK | Homo sapiens deoxythymidylate kinase (thymidylate kinase) (DTYMK), mRNA [NM_012145] | A_23_P123974 | NM_012145 | NP_036277 | | | | | | | |
| CDC25A | Homo sapiens cell division cycle 25 homolog A (S. pombe) (CDC25A), transcript variant 1, mRNA [NM_001789] | A_24_P397107 | NM_001789 | NP_001780 | x | | | x | x | x | |
| CDC7 | Homo sapiens cell division cycle 7 homolog (S. cerevisiae) (CDC7), transcript variant 1, mRNA [NM_003503] | A_23_P148807 | NM_003503 | NP_003494 | | | | | x | | x |
| DNA2 | Homo sapiens DNA replication helicase 2 homolog (yeast) (DNA2), mRNA [NM_001080449] | A_33_P3833211 | NM_001080449 | NP_001073918 | | | | x | | | |
| MCM6 | Homo sapiens minichromosome maintenance complex component 6 (MCM6), mRNA [NM_005915] | A_23_P90612 | NM_005915 | NP_005906 | | | | x | x | | x |
| CHAF1A | Homo sapiens chromatin assembly factor 1, subunit A (p150) (CHAF1A), mRNA [NM_005483] | A_24_P53519; A_33_P3416366 | NM_005483 | NP_005474 | | | | | | | |
| RFC2 | Homo sapiens replication factor C (activator 1) 2, 40kDa (RFC2), transcript variant 1, mRNA [NM_181471] | A_23_P93823 | NM_181471 | NP_852136 | | | | x | | | |

-continued

| HUGO Gene Symbol (1) | Description (2) | ProbeName (3) | RefSeq Nucleic Accession (4) | RefSeq Protein Accession (5) | GO "M phase of mitotic cell cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| RPA3 | Homo sapiens replication protein A3, 14kDa (RPA3), mRNA [NM_002947] | A_23_P256455 | NM_002947 | NP_002938 | | | | x | x | | x |
| STAG3 | Homo sapiens stromal antigen 3 (STAG3), mRNA[NM_012447] | A_23_P145657 | NM_012447 | NP_036579 | | | | | | | |
| CDC25B | Homo sapiens cell division cycle 25 homolog B (S. pombe) (CDC25B), transcript variant 1, mRNA [NM_021873] | A_23_P210726 | NM_021873 | NP_068659 | x | | | | | x | |
| SUV39H1 | Homo sapiens suppressor of variegation 3-9 homolog 1 (Drosophila) (SUV39H1), mRNA [NM_003173] | A_33_P3407524; A_23_P422193 | NM_003173 | NP_003164 | | | | | | | |
| RAD54B | Homo sapiens RAD54 homolog B (S. cerevisiae) (RAD54B), mRNA [NM_012415] | A_23_P82738 | NM_012415 | NP_036547 | | | | | | | |
| POLA2 | Homo sapiens polymerase (DNA directed), alpha 2 (70kD subunit) (POLA2), mRNA [NM_002689] | A_23_P161615 | NM_002689 | NP_002680 | | | | x | x | | x |
| CEP152 | Homo sapiens centrosomal protein 152kDa (CEP152), mRNA [NM_014985] | A_24_P652700 | NM_014985 | NP_055800 | | | | | | x | |
| NCAPD3 | Homo sapiens non-SMC condensin II complex, subunit D3 (NCAPD3), mRNA [NM_015261] | A_32_P71447 | NM_015261 | NP_056076 | x | | | | | | |
| POLD1 | Homo sapiens polymerase (DNA directed), delta 1, catalytic subunit 125kDa (POLD1), mRNA [NM_002691] | A_23_P50455 | NM_002691 | NP_002682 | | | | x | | | |
| RFC5 | Homo sapiens replication factor C (activator 1) 5, | A_23_P95302 | NM_181578 | NP_853556 | | | | x | | | |

| HUGO Gene Symbol (1) | Description (2) | ProbeName (3) | RefSeq Nucleic Accession (4) | RefSeq Protein Accession (5) | GO "M phase of mitotic cell cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| RFC4 | 36.5kDa (RFC5), transcript variant 2, mRNA [NM_181578] Homo sapiens replication factor C (activator 1) 4, 37kDa (RFC4), transcript variant 1, mRNA [NM_002916] | A_23_P18196 | NM_002916 | NP_002907 | | | | x | | | |
| MASTL | Homo sapiens microtubule associated serine/threonine kinase-like (MASTL), mRNA [NM_032844] | A_24_P258051 | NM_032844 | NP_116233 | x | | | | | x | |
| CENPN | Homo sapiens centromere protein N (CENPN), transcript variant 1, mRNA [NM_001100625] | A_33_P3387856 | NM_001100625 | NP_001094095 | x | | | | | | |
| CDKN2D | Homo sapiens cyclin-dependent kinase inhibitor 2D (p19, inhibits CDK4) (CDKN2D), transcript variant 1, mRNA [NM_001800] | A_23_P89941 | NM_001800 | NP_001791 | | x | | | x | | |
| ZWILCH | Homo sapiens Zwilch, kinetochore associated, homolog (Drosophila) (ZWILCH), transcript variant 1, mRNA [NM_017975] | A_33_P3443873 | NM_017975 | NP_060445 | x | | | | | | |
| DSN1 | Homo sapiens DSN1, MIND kinetochore complex component, homolog (S. cerevisiae) (DSN1), transcript variant 3, mRNA [NM_024918] | A_23_P165937 | NM_024918 | NP_079194 | x | | | | | | |
| LIG1 | Homo sapiens ligase 1, DNA, ATP-dependent (LIG1), mRNA [NM_000234] | A_23_P39116 | NM_000234 | NP_000225 | | | | x | | | |
| C21orf45 | Homo sapiens chromosome 21 open reading frame | A_23_P252335 | NM_018944 | NP_061817 | x | | | | | | |

-continued

| HUGO Gene Symbol (1) | Description (2) | ProbeName (3) | RefSeq Nucleic Acession (4) | RefSeq Protein Accession (5) | GO "M phase of mitotic cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| DSCC1 | 45 (C21orf45), mRNA [NM_018944] *Homo sapiens* defective in sister chromatid cohesion 1 homolog (*S. cerevisiae*) (DSCC1), mRNA [NM_024094] | A_23_P252740 | NM_024094 | NP_076999 | x | | | | | | |
| UBE2S | *Homo sapiens* ubiquitin-conjugating enzyme E2S (UBE2S), mRNA [NM_014501] | A_32_P171328 | NM_014501 | NP_055316 | x | | | | | | |
| CENPQ | *Homo sapiens* centromere protein Q (CENPQ), mRNA [NM_018132] | A_23_P70328 | NM_018132 | NP_060602 | x | | | | | | |
| G0S2 | *Homo sapiens* G0/G1 switch 2 (G0S2), mRNA [NM_015714] | A_23_P74609 | NM_015714 | NP_056529 | | | | | | | |
| LRRCC1 | *Homo sapiens* leucine rich repeat and coiled-coil domain containing 1 (LRRCC1), transcript variant 1, mRNA [NM_033402] | A_23_P157527 | NM_033402 | NP_208325 | x | | | | | | |
| CDK2 | *Homo sapiens* cyclin-dependent kinase 2 (CDK2), transcript variant 1, mRNA [NM_001798] | A_23_P98898 | NM_001798 | NP_001789 | x | x | x | x | x | x | x |
| | *Homo sapiens* cDNA FLJ53559 complete cds. [AK296555 coding for BAG59178] | A_33_P3407636 | | #N/A | | | | | | x | |
| CENPJ | *Homo sapiens* centromere protein J (CENPJ), mRNA [NM_018451] | A_32_P219116 | NM_018451 | NP_060921 | | | | | | x | |
| DDX11 | *Homo sapiens* DEAD/H (Asp-Glu-Ala-Asp/His) box polypeptide 11 (CHL1-like helicase homolog, *S. cerevisiae*) | A_23_P203949; A_23_P203947 | NM_030653 | NP_085911 | x | | | x | | x | |

-continued

| HUGO Gene Symbol (1) | Description (2) | ProbeName (3) | RefSeq Nucleic Accession (4) | RefSeq Protein Accession (5) | GO "M phase of mitotic cell cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| | (DDX11), transcript variant 1, mRNA (NM_030653] | | | | | | | | | | |
| SUV39H2 | Homo sapiens suppressor of variegation 3-9 homolog 2 (Drosophila) (SUV39H2), mRNA [NM_024670] | A_23_P202392 | NM_024670 | NP_078946 | | | | | | | |
| CEP72 | Homo sapiens centrosomal protein 72kDa (CEP72), mRNA [NM_018140] | A_23_P302654 | NM_018140 | NP_060610 | | | | | | x | |
| CEP110 | Homo sapiens centrosomal protein 110kDa (CEP110), mRNA [NM_007018] | A_33_P3257554 | NM_007018 | NP_008949 | | | | | | x | |
| SMC1A | Homo sapiens structural maintenance of chromosomes 1A (SMC1A), mRNA [NM_006306] | A_24_P942604 | NM_006306 | NP_006297 | x | | | | | | |
| PFTK2 | Homo sapiens PFTAIRE protein kinase 2 (PFTK2), mRNA [NM_139158] | A_23_P154050 | NM_139158 | NP_631897 | | | | | | | |
| MSH2 | Homo sapiens mutS homolog 2, colon cancer, nonpolyposis type 1 (E. coli) (MSH2), mRNA [NM_000251] | A_23_P102471; A_33_P3287502 | NM_000251 | NP_000242 | | | | | | | |
| PHGDH | Homo sapiens phosphoglycerate dehydrogenase (PHGDH), mRNA [NM_006623] | A_23_P85783 | NM_006623 | NP_006614 | | | | | | | |
| RCC1 | Homo sapiens regulator of chromosome condensation 1 (RCC1), transcript variant 1, mRNA [NM_001048194] | A_23_P46309 | NM_001048194 | NP_001041659 | | | | | x | | |
| HAUS5 | Homo sapiens HAUS augmin-like complex, | A_33_P3269338 | NM_015302 | NP_056117 | x | | | | | | |

-continued

| HUGO Gene Symbol (1) | Description (2) | ProbeName (3) | RefSeq Nucleic Accession (4) | RefSeq Protein Accession (5) | GO "M phase of mitotic cell cycle" (6) | GO "G1 phase" (7) | GO "G2 phase" (8) | GO "S phase" (9) | GO "G1/S transition of mitotic cell cycle" (10) | GO "G2/M transition of mitotic cell cycle" (11) | GO "M/G1 transition of mitotic cell cycle" (12) |
|---|---|---|---|---|---|---|---|---|---|---|---|
| | subunit 5 (HAUS5), mRNA [NM_015302] | | | | | | | | | | |
| CP110 | Homo sapiens CP110 protein (CP110), mRNA [NM_014711] | A_24_P373286 | NM_014711 | NP_055526 | | | | | | x | |
| HAUS1 | Homo sapiens HAUS augmin-like complex, subunit 1 (HAUS1), transcript variant 1, mRNA [NM_138443] | A_23_P413796 | NM_138443 | NP_612452 | x | | | | | | |
| CEP78 | Homo sapiens centrosomal protein 78kDa (CEP78), transcript variant 1, mRNA [NM_001098802] | A_33_P3219641 | NM_001098802 | NP_001092272 | | | | | | x | |
| CHEK1 | Homo sapiens CHK1 checkpoint homolog (S. pombe) (CHEK1), transcript variant 2, mRNA [NM_001114121] | A_33_P3349536 | NM_001114121 | NP_001107593 | | | | | | x | |
| YEATS4 | Homo sapiens YEATS domain containing 4 (YEATS4), mRNA [NM_006530] | A_23_P87591 | NM_006530 | NP_006521 | x | | | | | | |
| TUBGCP3 | Homo sapiens tubulin, gamma complex associated protein 3 (TUBGCP3), mRNA [NM_006322] | A_23_P76705 | NM_006322 | NP_006313 | | | | | | x | |
| BUB3 | Homo sapiens budding uninhibited by benzimidazoles 3 homolog (yeast) (BUB3), transcript variant 2, mRNA [NM_001007793] | A_23_P46924 | NM_001007793 | NP_001007794 | x | | | | | | |

Table 3.

Unregulated cell cycle genes sorted by decreasing Fold Change. Genes annotated in the "cell cycle" Gene Ontology category and which are upregulated in cells transduced with rLV-EF1 batch B and batch C at MOI150 compared to non-transduced cells. (1) HUGO gene symbol (2) Gene description from NCBI (3) Agilent Probe Identifier, (4) Nucleic sequence Accession Number from the NCBI database RefSeq RNA, (5) Proteic sequence Accession Number from the NCBI database RefSeq Protein. Genes are sorted by decreasing values of Fold Change.

Table 4.

18 cell cycle genes still downregulated with FC<−1.5 only with batch B at MOI 40. Genes annotated in the "cell cycle" Gene Ontology category, which are downregulated in cells transduced with rLV-EF1 batch B at MOI 40 and 150 and which are downregulated in cells transduced with rLV-EF1 batch C compared to non-transduced cells at MOI150 but not at MOI 40. (1) HUGO gene symbol (2) Gene description from NCBI (3) Agilent Probe Identifier, (4) Nucleic sequence Accession Number from the NCBI database RefSeq RNA, (5) Proteic sequence Accession Number from the NCBI database RefSeq Protein.

| GeneSymbol (1) | Description (2) | ProbeName (3) | RefSeq Nucleic Accession (4) | RefSeq Protein Accession (5) |
|---|---|---|---|---|
| CDKN1A | *Homo sapiens* cyclin-dependent kinase inhibitor 1A (p21, Cip1) (CDKN1A), transcript variant 2, mRNA [NM_078467] | A_24_P89457 | NM_078467 | NP_510867 |
| MDM2 | *Homo sapiens* Mdm2 p53 binding protein homolog (mouse) (MDM2), transcript variant MDM2, mRNA [NM_002392] | A_23_P502750 | NM_002392 | NP_002383 |
| TP53INP1 | *Homo sapiens* tumor protein p53 inducible nuclear protein 1 (TP53INP1), transcript variant 1, mRNA [NM_033285] | A_23_P168882 | NM_033285 | NP_150601 |
| TGFB2 | *Homo sapiens* transforming growth factor, beta 2 (TGFB2), transcript variant 2, mRNA [NM_003238] | A_24_P402438 | NM_003238 | NP_003229 |
| CDH13 | *Homo sapiens* cadherin 13, H-cadherin (heart) (CDH13), mRNA [NM_001257] | A_32_P85999 | NM_001257 | NP_001248 |
| RASSF2 | *Homo sapiens* Ras association (RalGDS/AF-6) domain family member 2 (RASSF2), transcript variant 1, mRNA [NM_014737] | A_23_P166087 | NM_014737 | NP_055552 |

| GeneSymbol (1) | Description (2) | ProbeName (3) | RefSeq Nucleic Accession (4) | RefSeq Protein Accession (5) |
|---|---|---|---|---|
| ASPM | *Homo sapiens* asp (abnormal spindle) homolog, microcephaly associated (Drosophila) (ASPM), mRNA [NM_018136] | A_33_P3288159 | NM_018136 | NP_060606 |
| AURKB | *Homo sapiens* aurora kinase B (AURKB), mRNA [NM_004217] | A_23_P130182 | NM_004217 | NP_004208 |
| CENPA | *Homo sapiens* centromere protein A (CENPA), transcript variant 1, mRNA [NM_001809] | A_24_P413884 | NM_001809 | NP_001800 |
| CENPF | *Homo sapiens* centromere protein F, 350/400 ka (mitosin) (CENPF), mRNA [NM_016343] | A_23_P401; A_24_P96780 | NM_016343 | NP_057427 |
| CKS1B | *Homo sapiens* CDC28 protein kinase regulatory subunit 1B (CKS1B), transcript variant 1, mRNA [NM_001826] | A_32_P206698 | NM_001826 | NP_001817 |
| E2F8 | *Homo sapiens* E2F transcription factor 8 (E2F8), mRNA [NM_024680] | A_23_P35871 | NM_024680 | NP_078956 |
| ERCC6L | *Homo sapiens* excision repair cross-complementing rodent repair deficiency, complementation group 6-like (ERCC6L), mRNA [NM_017669] | A_23_P96325 | NM_017669 | NP_060139 |
| FAM83D | *Homo sapiens* family with sequence similarity 83, member D (FAM83D), mRNA [NM_030919] | A_23_P323751 | NM_030919 | NP_112181 |
| KIFC1 | *Homo sapiens* kinesin family member C1 (KIFC1), mRNA [NM_002263] | A_23_P133956 | NM_002263 | NP_002254 |
| NEK2 | *Homo sapiens* NIMA (never in mitosis gene a)-related kinase 2 (NEK2), mRNA [NM_002497] | A_24_P319613 | NM_002497 | NP_002488 |
| NUSAP1 | *Homo sapiens* nucleolar and spindle associated protein 1 (NUSAP1), transcript variant 1, mRNA [NM_016359] | A_33_P3350488 | NM_016359 | NP_057443 |
| OIP5 | *Homo sapiens* Opa interacting protein 5 (OIP5), mRNA [NM_007280] | A_23_P379614 | NM_007280 | NP_009211 |

| GeneSymbol (1) | Description (2) | ProbeName (3) | RefSeq Nucleic Accession (4) | RefSeq Protein Accession (5) |
|---|---|---|---|---|
| PRC1 | *Homo sapiens* protein regulator of cytokinesis 1 (PRC1), transcript variant 1, mRNA [NM_003981] | A_23_P206059 | NM_003981 | NP_003972 |
| RRM2 | *Homo sapiens* ribonucleotide reductase M2 (RRM2), transcript variant 2, mRNA [NM_001034] | A_24_P225616 | NM_001034 | NP_001025 |
| SGOL1 | *Homo sapiens* shugoshin-like 1 (*S. pombe*) (SGOL1), transcript variant A2, mRNA [NM_001012410] | A_23_P29723 | NM_001012410 | NP_001012410 |
| SPC25 | *Homo sapiens* SPC25, NDC80 kinetochore complex component, homolog (*S. cerevisiae*) (SPC25), mRNA [NM_020675] | A_23_P51085 | NM_020675 | NP_065726 |
| TOP2A | *Homo sapiens* topoisomerase (DNA) II alpha 170kDa (TOP2A), mRNA [NM_001067] | A_23_P118834 | NM_001067 | NP_001058 |
| TTK | *Homo sapiens* TTK protein kinase (TTK), transcript variant 1, mRNA [NM_003318] | A_23_P259586 | NM_003318 | NP_003309 |

Table 5.

List of genes considered by the inventor as related to cellular senescence. List of genes related to cellular senescence, either being part of the "Senescence and autophagy" pathway referenced as WP615 in the publically accessible Wikipathway database or as extracted from the literature as being characteristic as the Senescence-Associated Secretory Phenotype (SASP). (1) HUGO gene symbol (2) Gene part of the SASP (3) Gene included into the "Senescence and autophagy" Wikipathway (4) Gene extracted as related to the SASP from Coppé et al., 2010 (5) Gene extracted as associated to the SASP from Young et al., 2009. [If we are merely citing to Wikipathway as the source of our current list of used genes that's okay—our genes are listed in the table. We just can't rely on Wikipathway for future searching. Whatever you cite to in the specification has to be permanent as of the filing date]

| HUGO gene symbol (1) | SASP (2) | "Senescence and Autophagy" Wikipathway (3) | Coppé et al, 2010 (4) | Young et al, 2009 (5) |
|---|---|---|---|---|
| AKT1S1 | | x | | |
| AMBRA1 | | x | | |
| ANG | x | | x | |
| AREG | x | | x | |
| ATG10 | | x | | |
| ATG16L1 | | x | | |
| ATG3 | | x | | |
| ATG5 | | x | | |
| ATG7 | | x | | |
| BCL2 | | x | | |
| BECN1 | | x | | |
| BMI1 | | x | | |
| BMP2 | | x | | |
| BRAF | | x | | |
| CCL1 | x | | x | |
| CCL3 | x | x | | |
| CCL8 | x | | x | |
| CCL11 | x | | x | |
| CCL13 | x | | x | |
| CCL20 | x | | x | |
| CCL25 | x | | x | |
| CCL26 | x | | x | |
| CCL16 | x | | x | |
| CD44 | | x | | |
| CDC25B | | x | | |
| CDKN1A | | x | | |
| CDKN1B | | x | | |
| CDKN2A | | x | | |
| CEBPB | x | x | | |
| COL10A1 | x | x | | |
| COL1A1 | x | x | | |
| CREG1 | | x | | |
| CSF2 | x | | x | |
| CSF3 | x | | x | |
| CTSB | x | | x | |
| CXCL1 | x | x | | |
| CXCL11 | x | | x | |
| CXCL12 | x | | x | |
| CXCL13 | x | | x | |
| CXCL14 | | x | | |
| CXCL2 | x | | x | |
| CXCL5 | x | | x | |
| CXCR2 | x | | | x |
| E2F1 | | x | | |
| EGF | x | | x | |
| EGFR | x | | x | |
| EREG | x | | x | |
| FAS | x | | x | |
| FGF2 | x | | x | |
| FGF7 | x | | x | |
| FKBP8 | | x | | |
| FN1 | x | | x | |
| GABARAP | | x | | |
| GABARAPL1 | | x | | |
| GABARAPL2 | | x | | |
| GSK3B | | x | | |
| GSN | | x | | |
| HGF | x | | x | |
| HMGA1 | | x | | |
| HRAS | | x | | |
| ICAM1 | x | | x | |
| ICAM3 | x | | x | |
| IFI16 | | x | | |
| IFNB1 | | x | | |
| IFNG | x | | x | |
| IGF1 | | x | | |
| IGF1R | | x | | |
| IGFBP2 | x | | x | |
| IGFBP3 | x | | x | |
| IGFBP4 | x | | x | |
| IGFBP5 | | x | | |
| IGFBP6 | x | | x | |
| IGFBP7 | x | x | | |
| IL1A | x | | x | |
| IL1B | x | | x | |
| IL13 | x | | | x |
| IL15 | x | | | x |
| IL24 | x | | | |
| IL3 | x | | | |

| HUGO gene symbol (1) | SASP (2) | "Senescence and Autophagy" Wikipathway (3) | Coppé et al, 2010 (4) | Young et al, 2009 (5) |
|---|---|---|---|---|
| IL6 | x | x | | |
| IL6R | | x | | |
| IL6ST | x | x | | |
| IL7 | | | x | |
| IL8 | x | x | | |
| ING1 | | x | | |
| ING2 | | x | | |
| INHBA | | x | | |
| INS | | x | | |
| IRF1 | | x | | |
| IRF5 | | x | | |
| IRF7 | | x | | |
| JUN | | x | | |
| KIAA0652 | | x | | |
| KITLG | x | | x | |
| LAMP1 | | x | | |
| LAMP2 | | x | | |
| MAP1LC3A | | x | | |
| MAP1LC3B | | x | | |
| MAP1LC3C | | x | | |
| MAP2K1 | | x | | |
| MAP2K3 | | x | | |
| MAPK1 | | x | | |
| MAPK14 | | x | | |
| MDM2 | | x | | |
| MLL | | x | | |
| MIF | x | | x | |
| MLST8 | | x | | |
| MMP10 | x | | x | |
| MMP12 | x | | x | |
| MMP13 | x | | x | |
| MMP14 | x | x | | |
| MMP1 | x | | x | |
| MMP3 | x | | x | |
| MTOR | | x | | |
| NGF | x | | x | |
| NRG1 | x | | x | |
| PIGF | x | | x | |
| PIK3C3 | | x | | |
| PLA2R1 | x | | | x |
| PLA2G2A | x | | | x |
| PLAT | x | x | | |
| PLAU | x | | x | |
| PLAUR | x | | x | |
| PTEN | | x | | |
| RAF1 | | x | | |
| RB1 | | x | | |
| RB1CC1 | | x | | |
| RNASEL | | x | | |
| RSL1D1 | | x | | |
| SERPINB2 | x | x | | |
| SERPINE1 | x | x | | |
| SH3GLB1 | | x | | |
| SLC39A1 | | x | | |
| SLC39A2 | | x | | |
| SLC39A3 | | x | | |
| SLC39A4 | | x | | |
| SPARC | | x | | |
| SQSTM1 | | x | | |
| SRC | | x | | |
| TIMP1 | x | x | | x |
| TIMP2 | x | x | | x |
| TGFB1 | | x | | |
| THBS1 | | x | | |
| TNFSF15 | | x | | |
| TNFRSF11B | x | | x | |
| TNFRSF10C | x | | x | |
| TNFRSF1B | x | | x | |
| TNFRSF1A | x | | x | |
| TP53 | | x | | |
| ULK1 | | x | | |
| UVRAG | | x | | |
| VEGF | x | | x | |
| VTN | | x | | |

Table 6.

16 senescence genes differentially expressed in cells transduced with batch B obtained with serum (B-S) at MOI 150 vs non-transduced cells. Cellular senescence-associated genes (either being part of the human "senescence and autophagy pathway >> referenced WP615 in the publically accessible Wikipathway database or part of the list of SASP genes extracted from the literature (Table 5)) which are differentially expressed genes in cells transduced with rLV-EF1 batch B-S at MOI 150 compared to non-transduced cells, which are not differential in cells transduced with rLV-EF1 batch B and batch C transduced cells at MOI 150 compared to non-transduced cells. By "not differential", is meant that the FC absolute value is <1.3. (1) HUGO gene symbol (2) Gene description from NCBI (3) Agilent Probe Identifier, (4) Nucleic sequence Accession Number from the NCBI database RefSeq RNA, (5) Proteic sequence Accession Number from the NCBI database RefSeq Protein.

| HUGO Gene Symbol (1) | Description (2) | ProbeName (3) | RefSeq Nucleic Accession (4) | RefSeq Protein Accession (5) |
|---|---|---|---|---|
| COL1A1 | Homo sapiens collagen, type I, alpha 1 (COL1A1), mRNA [NM_000088] | A_33_P3304668 | NM_000088 | NP_000079 |
| CXCL1 | Homo sapiens chemokine (C-X-C motif) ligand 1 (melanoma growth stimulating activity, alpha) (CXCL1), mRNA [NM_001511] | A_23_P7144; A_33_P3330264 | NM_001511 | NP_001502 |
| CXCL2 | Homo sapiens chemokine (C-X-C motif) ligand 2 (CXCL2), mRNA [NM_002089] | A_24_P257416; A_23_P315364 | NM_002089 | NP_002080 |
| GABARAPL1 | Homo sapiens GABA(A) receptor-associated protein like 1 (GABARAPL1), mRNA [NM_031412] | A_24_P4816; A_33_P3812669 | NM_031412 | NP_113600 |
| IGF1 | Homo sapiens insulin-like growth factor 1 (somatomedin C) (IGF1), transcript variant 4, mRNA [NM_000618] | A_23_P13907 | NM_000618 | NP_000609 |
| PLAU | Homo sapiens plasminogen activator, urokinase (PLAU), transcript variant 1, mRNA [NM_002658] | A_23_P24104; A_33_P3306146 | NM_002658 | NP_002649 |

| HUGO Gene Symbol (1) | Description (2) | ProbeName (3) | RefSeq Nucleic Accession (4) | RefSeq Protein Accession (5) |
|---|---|---|---|---|
| AREG | Homo sapiens amphiregulin (AREG), mRNA [NM_001657] | A_23_P259071 | NM_001657 | NP_0001648 |
| BMP2 | Homo sapiens bone morphogenetic protein 2 (BMP2), mRNA [NM_001200] | A_33_P3237150 | NM_001200 | NP_001191 |
| EREG | Homo sapiens epiregulin (EREG), mRNA [NM_001432] | A_23_P41344 | NM_001432 | NP_0001423 |
| HMGA1 | Homo sapiens high mobility group AT-hook 1 (HMGA1), transcript variant 3, mRNA [NM_145901] | A_23_P42331 | NM_145901 | NP_665908 |
| ICAM1 | Homo sapiens intercellular adhesion molecule 1 (ICAM1), mRNA [NM_000201] | A_23_P153320 | NM_000201 | NP_000192 |
| MMP1 | Homo sapiens matrix metallopeptidase 1 (interstitial collagenase) (MMP1), transcript variant 1, mRNA [NM_002421] | A_23_P1691 | NM_002421 | NP_002412 |
| MMP14 | Homo sapiens matrix metallopeptidase 14 (membrane-inserted) (MMP14), mRNA [NM_004995] | A_24_P82106 | NM_004995 | NP_004986 |
| NRG1 | Homo sapiens neuregulin 1 (NRG1), transcript variant HRG-gamma, mRNA [NM_004495] | A_33_P3284345 | NM_004495 | NP_004486 |
| PLAT | Homo sapiens plasminogen activator, tissue (PLAT), transcript variant 1, mRNA [NM_000930] | A_23_P82868 | NM_000930 | NP_000921 |
| PLAUR | Homo sapiens plasminogen activator, urokinase receptor (PLAUR), transcript variant 3, mRNA [NM_001005377] | A_23_P16469 | NM_001005377 | NP_001005377 |

Table 7.

Ten cellular senescence-associated biomarkers. These genes were selected from Table 6 as being differentially expressed in cells transduced with rLV-EF1 batch B-S at MOI 40 compared to non-transduced cells and not differential in rLV-EF1 batch B or C transduced cells at MOI 40. By "not differential", is meant that the FC absolute value is <1.3. (1) HUGO gene symbol (2) Gene description from NCBI (3) Agilent Probe Identifier, (4) Nucleic sequence Accession Number from the NCBI database RefSeq RNA, (5) Proteic sequence Accession Number from the NCBI database RefSeq Protein. (6) to (11) fold change values in each transduced condition compared to the non-transduced control condition. ND: not statistically differential. FC B-S vs NT MOI 150: Fold Change obtained between cells transduced with batch B-S at MOI 150 versus non-transduced cells. FC B vs NT MOI 150: Fold Change obtained between cells transduced with batch B at MOI 150 versus non-transduced cells. FC C vs NT MOI 150: Fold Change obtained between cells transduced with batch C at MOI 150 versus non-transduced cells. FC B vs NT MOI 40: Fold Change obtained between cells transduced with batch B at MOI 40 versus non-transduced cells. FC C vs NT MOI 40: Fold Change obtained between cells transduced with batch C at MOI 40 versus non-transduced cells. FC B-S vs NT MOI 40: Fold Change obtained between cells transduced with batch B-S at MOI 40 versus non-transduced cells.

| HUGO Gene Symbol (1) | Description (2) | ProbeName (3) | RefSeq Nucleic Accession (4) | RefSeq Protein Accession (5) | FC B-S vs NT MOI 150 (6) | FC B vs NT MOI 150 (7) | FC C vs NT MOI 150 (8) | FC B vs NT MOI 40 (9) | FC C vs NT MOI 40 (10) | FC B-S vs NT MOI 40 (11) |
|---|---|---|---|---|---|---|---|---|---|---|
| GABARAPL1 | Homo sapiens GABA(A) receptor-associated protein like 1 (GABARAPL1), mRNA [NM_031412] | A_24_P4816; A_33_P3812669 | NM_031412 | NP_113600 | −2.0 | #N/A | 1.4 | #N/A | #N/A | −1.5 |
| IGF1 | Homo sapiens insulin-like growth factor 1 (somatomedin C) (IGF1), transcript variant 4, mRNA [NM_000618] | A_23_P13907 | NM_000618 | NP_000609 | −2.8 | #N/A | 1.5 | #N/A | 1.3 | −2.3 |

-continued

| HUGO Gene Symbol (1) | Description (2) | ProbeName (3) | RefSeq Nucleic Accession (4) | RefSeq Protein Accession (5) | FC B-S vs NT MOI 150 (6) | FC B vs NT MOI 150 (7) | FC C vs NT MOI 150 (8) | FC B vs NT MOI 40 (9) | FC C vs NT MOI 40 (10) | FC B-S vs NT MOI 40 (11) |
|---|---|---|---|---|---|---|---|---|---|---|
| PLAU | *Homo sapiens* plasminogen activator, urokinase (PLAU), transcript variant 1, mRNA [NM_002658] | A_23_P24104; A_33_P3306146 | NM_002658 | NP_002649 | 3.3 | −1.4 | #N/A | #N/A | #N/A | 2.2 |
| BMP2 | *Homo sapiens* bone morphogenetic protein 2 (BMP2), mRNA [NM_001200] | A_33_P3237150 | NM_001200 | NP_001191 | 2.0 | #N/A | 1.2 | #N/A | #N/A | 2.3 |
| EREG | *Homo sapiens* epiregulin (EREG), mRNA [NM_001432] | A_23_P41344 | NM_001432 | NP_001423 | 2.5 | #N/A | #N/A | #N/A | #N/A | 2.0 |
| MMP1 | *Homo sapiens* matrix metallopeptidase 1 (interstitial collagenase) (MMP1), transcript variant 1, mRNA [NM_002421] | A_23_P1691 | NM_002421 | NP_002412 | 3.1 | #N/A | #N/A | #N/A | #N/A | 2.8 |
| MMP14 | *Homo sapiens* matrix metallopeptidase 14 (membrane-inserted) (MMP14), mRNA [NM_004995] | A_24_P82106 | NM_004995 | NP_004986 | 1.8 | #N/A | #N/A | #N/A | #N/A | 1.6 |
| NRG1 | *Homo sapiens* neuregulin 1 (NRG1), transcript variant HRG-gamma, mRNA [NM_004495] | A_33_P3284345 | NM_004495 | NP_004486 | 1.6 | #N/A | #N/A | #N/A | #N/A | 2.2 |
| PLAT | *Homo sapiens* plasminogen activator, tissue (PLAT), transcript variant 1, mRNA [NM_000930] | A_23_P82868 | NM_000930 | NP_000921 | 3.1 | #N/A | #N/A | #N/A | #N/A | 1.6 |
| PLAUR | *Homo sapiens* plasminogen activator, urokinase receptor (PLAUR), transcript variant 3, mRNA [NM_001005377] | A_23_P16469 | NM_001005377 | NP_001005377 | 1.7 | #N/A | #N/A | #N/A | #N/A | 1.9 |

Table 8.

Genes not impacted in cells transduced with batch C, compared to cells transduced with other batches. Selection of genes not impacted with a high-quality vector. (1) HUGO gene symbol (2) Gene description from NCBI (3) Agilent Probe Identifier, (4) Nucleic sequence Accession Number from the NCBI database RefSeq RNA, (5) Proteic sequence Accession Number from the NCBI database RefSeq Protein. (6) to (11) fold change values in each transduced condition compared to the non-transduced control condition. ND means not statistically differential. FC B-S vs NT MOI 150: Fold Change obtained between cells transduced with batch B-S at MOI 150 versus non-transduced cells. FC B vs NT MOI 150: Fold Change obtained between cells transduced with batch B at MOI 150 versus non-transduced cells. FC C vs NT MOI 150: Fold Change obtained between cells transduced with batch C at MOI 150 versus non-transduced cells. FC B vs NT MOI 40: Fold Change obtained between cells transduced with batch B at MOI 40 versus non-transduced cells. FC C vs NT MOI 40: Fold Change obtained between cells transduced with batch C at MOI 40 versus non-transduced cells. FC B-S vs NT MOI 40: Fold Change obtained between cells transduced with batch B-S at MOI 40 versus non-transduced cells.

| HUGO Gene Symbol (1) | Description (2) | Probe Name (3) | RefSeq Nucleic Accession (4) | RefSeq Protein Accession (5) | FC B vs NT MOI 150 (6) | FC C vs NT MOI 150 (7) | FC B-S vs NT MOI 150 (8) | FC B vs NT MOI 40 (9) | FC C vs NT MOI 40 (10) | FC B-S vs/NT MOI 40 (11) |
|---|---|---|---|---|---|---|---|---|---|---|
| CXCL2 | Homo sapiens chemokine (C-X-C motif) ligand 2 (CXCL2), mRNA [NM_002089] | A_24_P257416 | NM_002089 | NP_002080 | −2.04 | ND | 4.17 | −1.53 | ND | ND |
| FOXQ1 | Homo sapiens forkhead box Q1 (FOXQ1), mRNA [NM_033260] | A_32_P164246 | NM_033260 | NP_150285 | −1.82 | ND | 2.35 | −1.27 | ND | 1.36 |
| MAP3K8 | Mitogen-activated protein kinase kinase kinase 8 (EC 2, 7, 11, 25) (COT proto-oncogene serine/threonine-protein kinase) (Cancer Osaka thyroid oncogene) (C-COT) (Tumor progression locus 2) (TPL-2) [Source: UniProtKB/Swiss-Prot; Acc: P41279] [ENST00000375322] | A_33_P3246505 | * | ** | −2.08 | ND | −2.20 | ND (FC −1.23) | ND | −2.28 |

*The A_33_P3246505 probe sequence does not match to any RefSeq RNA accession number. It matches with Genbank accession number AY309013.
**AY309013 nucleic sequence corresponds to Genbank proteic accession number AAP45053.

Table 9.
Validation of cell cycle genes of table 4 as biomarkers with rLV-EF1-GFP MOI40.

| Gene Symbol | FC (BS vs. NT) | FC (B vs. NT) | FC (C vs. NT) |
|---|---|---|---|
| ASPM | −2.3 | −2.6 | −1.9 |
| ASPM | −2.1 | −2.5 | −2.0 |
| AURKB | −2.0 | −2.7 | −1.8 |
| CENPA | −2.1 | −2.8 | −1.9 |
| CENPF | −1.9 | −2.4 | −2.0 |
| CKS1B | −1.8 | −2.8 | −2.0 |
| CKS1B | −1.7 | −2.4 | −1.9 |
| E2F8 | −1.9 | −2.9 | −2.0 |
| ERCC6L | −1.7 | −2.5 | −1.8 |
| FAM83D | −1.9 | −2.9 | −2.1 |
| KIFC1 | −1.9 | −3.4 | −2.3 |
| MKI67 | −2.0 | −2.8 | −2.4 |
| MKI67 | −1.9 | −2.8 | −2.3 |
| MKI67 | −2.1 | −2.8 | −1.9 |
| NEK2 | −2.1 | −3.1 | −2.2 |
| NUSAP1 | −1.9 | −2.7 | −1.9 |
| OIP5 | −2.0 | −2.7 | −2.0 |
| PRC1 | −1.8 | −2.8 | −2.0 |
| RRM2 | −1.8 | −2.1 | −1.3 |
| SGOL1 | −2.4 | −3.0 | −2.1 |
| SPC25 | −1.8 | −2.8 | −1.8 |
| TOP2A | −2.0 | −2.4 | −1.6 |
| TTK | −1.9 | −2.6 | −1.7 |

Table 10. Sequence of primers used in the validation experiment.

| Gene symbol | Forward primer sequence (5' -> 3') | SEQ ID NO | Reverse primer sequence (5' -> 3') | SEQ ID NO |
|---|---|---|---|---|
| EREG | AGGAGGATGGAGATGCTCTGTG | 34 | ACTGCCTGTAGAAGATGGAAACCC | 35 |
| CXCL2 | CCCAAACCGAAGTCATAGCCACAC | 36 | GCCACCAATAAGCTTCCTCCTTCC | 37 |

Examples

The examples below are provided to help better understand the invention although the invention is not to be limited to these examples.

Material and Methods

Plasmid Construction.

Three plasmids were used to produce a recombinant virion or recombinant retrovirus. A first plasmid provides a nucleic acid encoding a viral gag and pol gene (FIG. 2A). These sequences encode a group specific antigen and reverse transcriptase, (and integrase and protease-enzymes necessary for maturation and reverse transcription), respectively, as discussed above. A second plasmid provides a nucleic acid encoding a viral envelope (env) (FIG. 2B), such as VSV-G (Vesicular Stomatitis Virus G). A third plasmid provides the cis-acting viral sequences necessary for the viral life cycle (FIG. 2C). This third plasmid also contains a cloning site for a heterologous nucleic acid sequence to be transferred to a target cell. A schematic illustration of a suitable vector is shown in FIG. 2C with the GFP as a transgene but which can be replaced by any gene or sequence of interest such as cDNA, shRNA or miRNA.

Viral Vectors Manufacturing Processes. Cell Lines and Culture Conditions.

Viral vectors were produced using a Human Embryonic Kidney (HEK293T) cell line. A Human colon carcinoma (HCT116; ATCC N° CCL-247) adherent cell line is used for quantification of infectious particles. All cells were provided by the American Type Culture Collection (ATCC) and cultured in Dulbecco's Modified Eagle's Medium (DMEM, Gibco, Paisley, UK) supplemented with 10% FCS; 1% penicillin/streptomycin and 1% ultraglutamine (PAA) at 37° C. in a humidified atmosphere of 5% $CO_2$ in air. For the production of viral vector supernatants, DMEM was only supplemented with 1% penicillin/streptomycin and 1% ultraglutamine (PAA).

Viral Vectors Production.

Viral vector production was performed in a 10-layer CellSTACK (6320 cm$^2$, Corning). HEK293T cells were seeded at 9.5×10$^3$ viable cells/cm$^2$ in DMEM supplemented with 10% FCS; 1% penicillin/streptomycin and 1% ultraglutamine (PAA) and placed at 37° C. in a humidified atmosphere of 5% CO$_2$ in air. Four days after seeding, the supernatant was discarded and replaced by fresh DMEM without FCS supplemented with 1% penicillin/streptomycin and 1% ultraglutamine (PAA) before transfecting the cells.

The tri-transfection mix was composed by the following three plasmids: pENV, pGagPol (viral DNA construct contained in the bacterial host deposited at CNCM Collection respectively under the accession number CNCM I-4487 and CNCM I-4488), and pLV-EF1 (viral DNA construct derived from that contained in the bacterial host deposited at CNCM Collection under the accession number CNCM I-4489). The final concentration was adjusted to 40 mg/ml-1 using sterile water. CaCl$_2$ (2.5M) was then dripped to the plasmid-water mixture under soft checking to reach a final concentration of 500 mM. The obtained mixture was then dripped to an equivalent volume of Hepes Buffered Saline (HBS 2×) and incubated at room temperature for 20 minutes. After incubation, the transfection mixture was added to the cell culture media and incubated for 24 hours at 37° C. in a humidified atmosphere of 5% CO$_2$ in air.

After 24 hours post-transfection, the supernatant was discarded and replaced with fresh non-supplemented DMEM and the cells were incubated at 37° C. in a humidified atmosphere of 5% CO$_2$ in air. After medium exchange, the supernatant was collected several times (32 h, 48 h, 56 h and 72 h post transfection). Some fresh and no supplemented media were added and the cells were incubated prior to further harvests at 37° C. in a humidified atmosphere of 5% CO$_2$.

Each harvest was clarified by centrifugation for 5 min. at 3000 g before being microfiltered through 0.45 μm pore size sterile filter unit (Stericup, Millipore). The whole set of harvest were then pooled to supply the crude harvest to obtain the Batch A (crude viral vectors composition).

Viral Vectors Concentration and Purification.

The viral vector compositions used to identify biomarkers of the present invention are obtained by a standard and commonly used concentration process based on either ultracentrifugation or centrifugation on central units (corresponding to the obtaining of batch B), or by concentration and/or purification processes (C and D) associated with a serum free production process (corresponding to the obtaining of batch A), as described in the PCT application WO 2013/014537 incorporated by reference in its entirety herein. Another batch UC (or UC-S) is produced for validation experiments obtained in presence of serum and concentrated by ultracentrifugation. The different batches correspond to different purification strategies going from no purification to several purification steps based on ultrafiltration and chromatography. The concentration and purification of the crude harvest was first performed by tangential flow ultrafiltration using polysulfone hollow-fiber cartridges. The supernatant was then diafiltered for 20 diavolumes in a continuous mode diafiltration against DMEM or TSSM buffer. Once the diafiltration performed, the retentate was recovered and further concentrated on ultrafiltration disposable units. The hollow fiber filtration (HFF) retentate was then benzonase treated by addition of Benzonase (250 U/μl)) for a final concentration of (72 U/ml), and MgCl$_2$ (1.0 mM) for a final concentration of 1 μM, before being incubating at 37° C. for 20 minutes.

The post HFF material can be further purified by ion exchange chromatography (IEX) on Sartobind Q75 (Sartorius) disposable membrane using an AKTA purifier system (GE Healthcare). The ion exchange membrane would be equilibrated with 5 column volumes of non-supplemented DMEM (or TSSM) at 2 ml/min. The viral supernatant would be then loaded on the membrane at 2 ml/min using a sampling loop. The flow through would be collected. The following step gradient can be applied to the AKTA system: 0M, 0.5M, 1.2M and 2M NaCl. The elution pic (collected with the 1.2 m NaCl step gradient) would be immediately 10× diluted in the following buffer: 20 mMTris+1.0% w/v Sucrose+1.0% w/v Mannitol, pH7.3 and further concentrated on ultrafiltration disposable units.

Viral Vectors Compositions.

Viral vectors compositions are obtained by the method described in the PCT application WO 2013/014537 incorporated by reference in its entirety herein. The resulting compositions are Batch B obtained after centrifugation on central units of batch A;

Batch C obtained after tangential ultrafitration diafiltration of batch A;

Batch C-S obtained after tangential ultrafitration diafiltration of batch A produced in the presence of 10% Fetal Bovine Serum (BIOWEST). This batch is only used for FIG. 13;

Batch B-S obtained in the presence of 10% Fetal Bovine Serum (BIOWEST) by the same process as the batch B without serum;

Batch UC or UC-S obtained in presence of 10% Fetal Bovine Serum (BIOWEST) and concentrated by ultracentrifugation.

The processes used to obtain these batches are described in FIGS. 1A and 1B.

Functional Particle Quantification Using qPCR.

Transduction unit titration assays were performed as follows. HCT116 cells are seeded in 96-wells plate at 12500 cells per well and 250 μL of DMEM supplemented with 10% FCS; 1% penicillin/streptomycin and 1% ultraglutamine (complete medium). 24 h later, five serial dilutions are performed with complete medium for each vector sample and for a known a rLV-EF1-GFP as an internal standard (viral DNA construct contained in the bacterial host deposited at CNCM Collection under the accession number CNCM 1-4489). The cells are transduced by these serial dilutions in the presence of 8 μg/mL Polybrene® (Sigma). For each sample series, one well of non-transduced cells is added for control. Three days post-transduction, cells are trypsinized and each cell pellet is taken up with 250 μL of PBS, genomic DNA are extracted and submitted to qPCR. Results are normalized with the known rLV-EF1-GFP internal standard that was previously titrated by FACS, using 100 μL of the cell suspension. The titre is expressed by transducing units/ml (TU/mL) using the internal standard whose titre was previously determined by FACS (Canto II) using standard conditions by considering the percentage of positive cells.

Physical Particle Quantitation by P24 ELISA Assays.

The p24 core antigen is detected directly on the viral supernatant with a HIV-1 p24 ELISA kit provided by Perkin Elmer. The kit is used as specified by the supplier. The captured antigen is complexed with biotinylated polyclonal antibody to HIV-1 p24, followed by a streptavidin-HRP (horseradish peroxidase) conjugate. The resulting complex is detected by incubation with ortho-phenylenediamine-HCl (OPD) which produces a yellow color that is directly proportional to the amount of p24 captured. The absorbance of each microplate well is determined using microplate reader and calibrated against absorbance of an HIV-1 p24 antigen standard curve. The viral titer expressed in physical particles per ml is calculated from the amount of p24 knowing that 1 pg of p24 corresponds to $10^4$ physical particles.

Empty Cassette Vector Production for Microarray Analyses.

Lentiviral vector without cDNA (rLV-EF1) was produced at different purities for microarray studies. Batches B and C of rLV-EF1 vectors were purified from the same crude harvest. An additional production was achieved in the presence of 10% Fetal Bovine Serum (BIOWEST) in order to generate a B batch containing serum, hereinafter mentioned as B-S batch.

GFP Expressing Lentiviral Vector Production.

Independent batches B, C, B-S of GFP expressing lentiviral vectors were produced.

In order to provide another type of low quality concentrated vector, ultracentrifugation method was used to concentrate vectors produced in the presence of 10% serum (Batch UC or UC-S).

Culture of Foreskin Cells.

Human foreskin fibroblast cells were obtained from the American Type Culture Collection (N° CRL-2097) and cultured in EMEM (Earl's Minimum Essential Medium, GIBCO) supplemented with 10% Fetal Bovine Serum (BIOWEST), 1% penicillin/streptomycin (PAA) and 2 mM glutamine (PAA). Cells were maintained at 37° C. in the presence of 5% $CO_2$ and passaged twice a week at 5 000 cells/cm$^2$.

Transduction of Foreskin Cells for Transcriptomics Analysis.

Human foreskin fibroblasts were seeded at 5000 cells/cm$^2$ in T25-flasks 24 hours before transduction. Cells were transduced in quadruplicate at MOI 40 and 150 using the batches B, C and B-S of rLV-EF1 vector in a final volume of 5 mL and in the presence of 4 µg/mL of Polybrene® (Sigma). A non-transduced control only received 4 µg/mL of Polybrene®. The transduction supernatant is removed after approximately 16 h. Cells were trypsinized 54 hours post-transduction, washed with 1×PBS, centrifuged and the pellets were kept at −80° C. Pictures were taken 48 hours post-transduction.

Human foreskin fibroblasts were seeded at 5000 cells/cm$^2$ in 6 well-multiplate 24 hours before transduction. Cells were transduced in quadruplicate at MOI 40 and 150 using the batches B, C, B-S and UC (or UC-S) of rLV-EF1-GFP vector in a final volume of 5 mL and in the presence of 4 µg/mL of Polybrene® (Sigma). A non-transduced control only received 4 µg/mL of Polybrene®. The transduction supernatant is removed after approximately 16 h. Cells were trypsinized 54 hours post-transduction, washed with 1×PBS, centrifuged and the pellets were kept at −80° C. Pictures were taken 48 hours post-transduction.

RNA Extractions.

Total RNA samples were extracted from cell pellets using the TRIZol® Plus RNA Purification System (Life Technologies) according to manufacturer's instructions. Total RNA concentration and purity were determined using a Nanodrop 1000 spectrophotometer (Nanodrop Technologies). RNA quality and integrity were checked with the Agilent 2100 Bioanalyzer (Agilent Technologies, USA) and were conform to Agilent microarrays' requirements.

DNA Microarray Experiments.

Microarray experiments were performed at the Biochips Platform of Genopole, University of Toulouse, INSA, UPS, INP, CNRS & INRA (Toulouse, France) according to manufacturer protocols. Briefly, after addition of a dilution of exogenous RNA from the one color RNA Spike-In Kit (Agilent Technologies) for quality control check, 100 ng of total RNA were converted to cRNA, amplified and cyanine 3-labeled using the Agilent Low Input Quick Amp kit. 1650 ng of cyanine 3-labeled cRNA were hybridized at 65° C. for 17 hours at 10 rpm to Agilent Whole Human Genome Oligo Microarrays 4×44K version 2, containing 44 000 probes (consisting of 60-mer length oligonucleotides) targeting 27 958 genes. Hybridized arrays were washed and scanned on the Agilent high-resolution scanner G2505C and the images were analyzed using Feature Extraction 10.10 (Agilent Technologies). After quality control based on Feature Extraction QC reports, 3 or 4 replicates were retained per condition. Concerning the validation experiment with rLV-EF1-GFP, the Feature Extraction 11.5 version was used.

Microarray Data Statistical Analyses.

Raw datasets from Feature Extraction were imported into GeneSpring® GX 12 Software (Agilent Technologies) and normalized using the 75th percentile methods. Probes were then filtered by flag values attributed by GeneSpring® when importing Feature Extraction data (for each probe, one of the following flag is affected: "detected", "not detected" or "compromised", using GeneSpring® default parameters). Probes detected and not compromised in more than 60% of replicates in at least one condition were retained (eliminating undetected or compromised spots). Baseline transformation of intensity values to median of all samples was applied for profile plot representations. It means that, for each probe, the median of the log summarized values from all the samples is calculated and subtracted from each of the samples. In order to identify differentially expressed probes between each condition and the control condition, independent t-tests were performed with Benjamini-Hochberg multiple test correction and a corrected p-value<0.05. Probes with absolute value of fold changes (FC)≥1.5 were retained as differentially expressed for both up and down-regulated probes.

Microarray Data Functional Analyses.

Annotations provided by Agilent and included in GeneSpring® are based on a dataset called 'technology' in GeneSpring® and named 26652 version 2012.1.10. For each probe, different type of annotations are provided including Gene symbol, Description, Gene Ontology terms, RefSeq RNA accession number among other data. It should be noted that only one RefSeq transcript is associated with each probe, although a probe can target several alternative transcripts of the same gene. The gene ontology (GO) option on GeneSpring® GX 12 was used to determine the most significant biological processes (corrected p-value<0.1) represented in differentially expressed probe lists, compared with the human whole genome. Pathway analysis was used to find direct relationships between entities of interest. This was performed in GeneSpring® with the "Single Experiment Analysis" algorithm. The selected human pathway sources were curated pathways referenced in WikiPathways included by default in GeneSpring® GX 12. Pathways with a p-value<0.05 and a minimal number of 5 genes were retained.

Relative Quantitative RT-PCR (RT-qPCR).

A total of 1 µg of total RNA from each sample was reverse transcribed using the Superscript III RT cDNA synthesis kit (Life Technologies) and oligo(dT)$_{12-18}$ according to manufacturer's instructions. cDNA products were then mixed with SYBR® GreenER™ qPCR SuperMixes for ABI PRISM (Life Technologies) and specific primers synthesized by Eurogentec (Belgium). GAPDH was used as an internal control to normalize transcript levels. All primers were designed using Primer 3 software version V.0.4.0 and their characteristics are summarized in table 1. Real time PCR was performed in duplicate, from at least two independent samples, using a StepOne instrument (Applied Biosystems) and relative quantification was calculated by the 2-ΔΔCT method (Livak et al. 2001). For the validation experiment, additional primers listed in table 10 were used and RT-qPCR was performed in duplicate from three independent samples. To assess significance of gene differential expressions, unpaired Student t-tests were performed to compare ΔΔCt values between conditions, with a p-value cut-off of 0.05.

Results

Candidate Biomarkers Identification

Impact on Proliferation of Cultured Cells Transduced with a Highly Purified Viral Vector Composition Versus an Ordinary Concentrated Viral Vector Composition.

In order to evaluate viral vector transduction effects according to the purity level and independently from any transgene, foreskin fibroblast cells were transduced at MOI 40 and 150 with two rLV-EF1 (without cDNA) compositions, batch B and batch C (described above) derived from the same crude harvest (batch A) and whose characteristics are summarized in FIG. 1A. Cells were observed 48 hours after transduction as presented in FIG. 2B.

A slight growth retardation was visible at MOI 40 with batch B transduced cells compared to non-transduced cells, although no growth difference was noticeable after batch C transduction at the same MOI.

Thus, at usual MOI (MOI 40 is commonly used for foreskin transduction), highly purified viral vector composition (batch C) does not induce a visible effect on transduced cells growth, whereas ordinary concentrated viral vector composition (batch B) seems to give a negative impact on transduced cells growth.

At MOI 150, a strong proliferation arrest could be seen with batch B transduced cells compared to non-transduced cells, whereas we only observed a moderate growth retardation with batch C.

Impact on Cell the Transcriptome of Cells Transduced with a Highly Purified Viral Vector Composition Versus an Ordinary Concentrated Viral Vector Composition.

As an example, the ordinary concentrated viral vector composition means the batch B obtained with serum (B-S). To explore underlying changes at the transcriptional level, these cells were collected 54 hours post-transduction. This post-transduction delay of 54 hours was determined as appropriate from a preliminary study as it was between the time when a growth delay appeared in transduced cells versus non-transduced cells, and the time when non-transduced cells reached confluence (data not shown). RNA were extracted and used to perform Agilent whole human genome microarrays allowing the quantification of nearly all human transcripts.

Transcriptional Changes Observed at MOI 150.

First, RNA levels from cells transduced with rLV-EF1 batch B and rLV-EF1 batch C at MOI 150 were compared to RNA from non-transduced cells. After statistical analyses, probes upregulated or downregulated 1.5-fold or more were retained for each comparison.

As shown in FIGS. 3A and 3B, a number of 1027 probes were differentially expressed in transduced cells after batch B transduction and a number of 906 probes were differentially expressed in transduced cells after batch C transduction, compared to non-transduced cells. Downregulated probes were almost twice as numerous as upregulated probes (703 and 650 downregulated probes, respectively for transduced cells with batch B and batch C).

Comparison of the downregulated genes at MOI 150 shows that the majority of downregulated genes were common to the analysis of the transcriptome of cells transduced with batch B versus the transcriptome of non-transduced cells transcriptome and analysis of the transcriptome of cell transduced with batch C versus the transcriptome of non-transduced cells tr, except for a set of batch-specific genes which are specifically impacted in the transcriptome of cells transduced with batch B or the transcriptome of cells transduced with batch C. As shown on the Venn diagram in FIG. 4, 560 downregulated probes represent the intersection of the two lists of downregulated probes. Thus, there is a pool of 560 probes commonly impacted in transcriptome of cells transduced with batch B or C versus non-transduced cells transcriptome.

A Gene Ontology (GO) analysis with GeneSpring® on these 560 probes revealed that cell cycle genes were significantly overrepresented with 239 probes (representing 204 distinct genes among the 1004 human genes comprised in the "cell cycle" GO category). These genes are presented in Table 2, sorted by increasing FC values. Numerous other GO terms were significantly overrepresented, the majority being linked to cell cycle. In particular, all GO categories corresponding to each cell cycle phases and transitions were significantly impacted.

In order to go further with the analysis of the 560 common downregulated probes, a pathway analysis was performed on this list using GeneSpring®. The first resulting human pathway was the human "Cell cycle" pathway referenced WP179 in the publically accessible Wikipathway database on July 2012 with 37 genes whose expression level is impacted-. "G1 to S cell cycle control" (WP45 reference in the publically accessible Wikipathway database on July 2012 database), "Mitotic G2-G2/M phases" (WP1859 reference in the publically accessible Wikipathway database on July 2012) and "Mitotic M-M/G1 phases" (WP1860 reference in the publically accessible Wikipathway database on July 2012) human pathways were also significantly impacted. Hence, all cell cycle phases seem to be impacted with major downregulations. Cell cycle arrest at the G2-M checkpoint was confirmed by downregulation of CDC25C, Cyclin B1 and CDC2 (HUGO gene nomenclature) associated with an upregulation of p21 (Chiu et al 2011). Other blockages need to be confirmed.

Among genes annotated in the GO category "cell cycle", the proliferation marker MKI67 was highly downregulated, with an average FC value of −8.6 and −5.6 (average FC value obtained with the values of the 3 probes representing this gene) on transcriptome of cells transduced respectively with batch B and batch C, versus non-transduced cells transcriptome. These values correlate with the observed proliferation retardation which was more pronounced after batch B transduction compared to batch C transduction.

A similar FC difference was almost systematically observed between the two conditions (i.e batch B and batch C), with an average 30% lower FC for these genes on transcription level in cells transduced with batch B versus transcription level in non-transduced cells compared to transcription level in cells transduced with batch C versus transcription level in non-transduced cells, as illustrated in FIG. 5. This observation is based on selection of probes impacted in cells transduced with batch B at MOI 150, having FC values≤−3. The FC difference was at least of 10%, except for 5 genes of this selection Downregulations of cell cycle genes are more pronounced in cells transduced with batch B versus non-transduced cells compared to cells transduced with batch C versus non-transduced cells.

Remarkably, 6 genes annotated in GO as "cell cycle" were upregulated with the two batches (i.e batch B and batch C) compared to non-transduced cells: CDKN1A, MDM2, TP53INP1, TGFB2, CDH13, RASSF2 according to HUGO gene nomenclature (as presented in Table 3). It could be noted that CDKN1A, encoding p21protein, corresponds to a cell cycle inhibitor, and that its overexpression is stronger in cells transduced with batch B versus non-transduced cells than cells transduced with batch C versus non-transduced cells.

Transcriptional changes observed at MOI 40.

Then, RNA levels from cells transduced with rLV-EF1 batch B and C at MOI 40 were compared to RNA of non-transduced cells. After statistical analyses, probes upregulated or downregulated 1.5-fold or more were retained for each comparison.

Among the 239 cell cycle downregulated probes at MOI 150 with rLV-EF1 batch B or C versus non-transduced cells, only 31 probes (representing 28 genes) were also underexpressed at MOI 40 with batch B versus non-transduced cells, and among them, 10 probes were downregulated with batch C versus non-transduced cells at the same MOI. FC were comprised between −1.5 and −2 at MOI 40, although they were comprised between −1.5 and −19 at MOI 150, showing that the impact on cell cycle was deeply stronger at MOI 150 compared to MOI 40.

Finally, there were 18 cell cycle genes impacted with FC values≤−1.5 only with batch B, FC being above the −1.5 cut-off for batch C at MOI 40. These genes are: ASPM, AURKB, CENPA, CENPF, CKS1B, E2F8, ERCC6L, FAM83D, KIFC1, NEK2, NUSAP1, OIP5, PRC1, RRM2, SGOL1, SPC25, TOP2A, TTK according to HUGO gene nomenclature (Table 4), correspond to the first cell cycle genes impacted in response to cell contact with a viral vector, and their deregulation happens earlier with a low quality vector batch compared to a highly purified vector batch. Thus, such genes could be used as early markers of an impact of a viral vector composition on the cell cycle of target cells.

Quantitative PCR Validations.

This Example describes subsequent technical validation of cell cycle genes underexpression by RT-qPCR. In order to confirm differential expression values obtained from microarrays experiments, a set of 5 cell cycle genes (E2F8, MKI67, NEK2, AURKB, CENPA according to HUGO gene nomenclature) was chosen among the 10 more under-expressed probes in cells transduced with batch B compared to non-transduced cells at MOI 150, RT-qPCR was performed on RNA from batch B and batch C transduced cells at MOI 150 versus non-transduced cells. The results, presented in FIGS. 6A and 6B, confirm the under-expression of these genes, and the stronger downregulation resulting from batch B transduction compared to batch C transduction.

Impact of a Viral Vector Batch Produced with Serum on Cell Transcriptome.

In order to assess the effects of vector medium composition after production of the viral vector composition with serum, rLV-EF1 vector (without cDNA) was produced in the presence of 10% serum and concentrated using process B, giving a batch B-S, whose characteristics are summarized in FIG. 7B. This batch was used to transduce foreskin cells at MOI 40 and MOI 150.

Cells were observed 48 hours after transduction, as shown in FIG. 7A. A growth arrest of cells transduced with batch B-S compared to non-transduced cells. This growth arrest is stronger at higher MOI (MOI 150) compared to MOI 40. Remarkably, Aggregates could be observed in cells transduced with batch B-S, and their volume increases with MOI. These cells were collected 54 hours after transduction for RNA extractions and microarray hybridizations. Surprisingly, during trypsinization, the cells transduced with batch B-S were more difficult to detach than cells transduced with batch B or C or non-transduced cells. RNA levels of cells transduced with batch B-S at moderate or higher MOI were compared to RNA of non-transduced cells using Agilent whole human genome microarrays. After statistical analyses, probes upregulated or downregulated 1.5-fold or more were retained for each comparison.

Transcriptional Changes Observed in Cells Transduced with Batch B-S at MOI 150 Versus Non-Transduced Cells.

1019 probes were significantly differential in cells transduced with batch B-S at MOI 150 compared to non-transduced cells as shown in FIG. 8. GeneSpring® Pathway analysis on this list revealed that the human "senescence and autophagy" Wikipathway (WP1267 reference in the Wikipathway database was significantly impacted with 10 differential genes: BMP2, COL1A1, CXCL1, GABARAPL1, HMGA1, IGF1, IL1B, MMP14, PLAT, SERPINB2 according to HUGO gene nomenclature (other impacted pathways: cell cycle, MAP kinase, focal adhesion . . . ).

A number of supplementary genes associated with the Senescence-Associated Secretory Phenotype (SASP) but not included in the senescence and autophagy pathway of Wikipathway were selected for testing. The list was extracted from the data of the literature (Coppé et al. 2010 and Young et al. 2009). A defined relevant list of cellular senescence associated genes from "senescence and autophagy" pathway and literature, is represented in Table 5.

Finally, 20 genes belonging to the pathway "senescence and autophagy" or associated with the SASP (AREG, BMP2, COL1A1, CXCL1, CXCL2, EREG, GABARAPL1, HMGA1, ICAM1, IGF1, IL1B, MMP1, MMP14, MMP3, NRG1, PLAT, PLAU, PLAUR, SERPINB2 and TNFRSF10C according to HUGO gene nomenclature, not represented in Tables) were selected because they appeared to be differentially expressed in cells transduced with batch B-S compared to non-transduced cells. Moreover, several collagen genes were downregulated, and PTGS2 gene was upregulated: these genes also participate into the senescence biological process (Coppé et al. 2010).

Among the 20 genes belonging to the pathway "senescence and autophagy" or associated with the SASP identified above, 10 genes are not impacted in cells transduced with batch B or C versus non-transduced cells, at MOI 150 (AREG, BMP2, EREG, HMGA1, ICAM1, MMP1, MMP14, NRG1, PLAT and PLAUR according to HUGO gene nomenclature). By "not impacted", it is meant that the FC absolute value is <1.3.

6 other genes were also impacted in cells transduced with batch B or C versus non-transduced cells but in an opposite way as the change happening during cellular senescence (COL1A1, CXCL1, CXCL2, GABARAPL1, IGF1 and PLAU according to HUGO gene nomenclature). Finally, 16 genes present an expression profile characteristic of the apparition of cellular senescence only in response to batch B-S, compared to other batches at MOI 150. These 16 genes are presented in table 5.

Transcriptional Changes Observed in Cells Transduced with Batch B-S at MOI 40 Versus Non-Transduced Cells.

Differentially expressed probes with the B-S batch at MOI 40 were examined. 2841 probes were significantly differentially expressed compared to the non-transduced control as shown in FIG. 9. As shown in FIG. 10, 631 probes were still differential among the 1019 differential probes at higher MOI.

In order to identify probes associated with vectors produced with serum, probes were selected that were differentially expressed in cells transduced with batch B-S (at both MOD versus the non-transduced condition, and that were not differential in cells transduced with batches B and C (at both MOI). The corresponding set of 235 genes is represented in the profile plot shown in FIG. 11. By "not differential", it is meant that the FC absolute value is <1.3.

Within this list of 235 genes, cellular senescence-associated genes were selected in order to identify early biomarkers of the apparition of a senescent phenotype in cells in contact with a viral vector. A list of 10 cellular senescence-associated genes was obtained, which could be candidate biomarkers revealing a negative impact of a viral vector composition on cells to be transduced. These genes are GABARAPL1, IGF1, PLAU, BMP2, EREG, MMP1, MMP14, NRG1, PLAT and PLAUR according to HUGO gene nomenclature (more details in table 7).

Selection of Restricted List of Genes not Impacted with a High-Quality Vector.

This example discloses a selection of genes not impacted by batch C (both MOD and impacted with other batches. Whereas most of differentially expressed genes are commonly expressed in cells transduced with batch B versus non-transduced cells and cells transduced with batch C versus non-transduced cells at MOI 150, a few genes show different expression patterns.

In order to select genes specifically impacted in cells in contact with a low quality vector composition, probes that were not differentially expressed with batch C (FC chosen between −1.2 and 1.2) and differentially expressed in cells transduced with batch B versus non-transduced cells at MOI 40 and 150 were selected. The corresponding selection results in one gene: CXCL2. Two other genes share the same profile, except for reduced FC values for B versus NT at MOI 40 (absolute values comprised between 1.3 and 1.5): FOXQ1 and ZNF547 (Agilent Probe ID: A_33_P3352822, RefSeq mRNA accession number: NM_173631, RefSeq protein accession number: NP_775902).

Interestingly, CXCL2 and FOXQ1 are also differential when comparing cells transduced with batch B-S versus non-transduced cells at MOI 150 but with an opposite evolution, as they are over-expressed cells transduced with batch B-S versus non-transduced cells, although they are under-expressed in cells transduced with batch B versus non-transduced cells.

Another gene presents an interesting expression profile: MAP3K8. The corresponding probe was not initially selected as it is not statistically significantly differential at MOI 40 when comparing cells transduced with batch B versus non-transduced cells, but a slight difference could be seen when examining intensity values, corresponding to a FC value of −1.2, thus confirming the downregulation tendency observed at higher MOI. This gene is downregulated in cells transduced with batches B and B-S versus non-transduced cells and not differential in cells transduced with batch C at both MOI.

These three genes (CXCL2, FOXQ1 and MAP3K8 according to HUGO gene nomenclature), shown in Table 8, are hence biomarkers for use in the practice of the invention as their expression is specifically impacted when transducing cells with a low quality vector batch, and not affected by high quality vector transduction.

Candidate Biomarkers Validation.

In order to validate candidate biomarkers response depending on lentiviral vector batch quality, an independent experiment was performed. Foreskin fibroblast cells were transduced at MOI 40 and 150 with five rLV-EF1-GFP compositions: batch B, batch C, batch C-S, batch B-S and batch UC (or UC-S) (described above) and whose characteristics are summarized in FIG. 12. These batches were deeply characterized in order to ensure the most precise comparisons between conditions. Cells were observed 48 hours after transduction as presented in FIG. 13. At MOI 40, a growth retardation with batch B transduced cells compared to non-transduced cells was confirmed, as well as the absence of visible retardation with batch C. All the other batches produced with serum, induced cell proliferation delays, similarly to batch B. Thus, the proliferation rate with batch B is better than with batch B-S, and the one with batch C is better than with batch C-S. At MOI 150, the only one batch which does not impact the cell proliferation is batch C. A strong proliferation arrest is seen with batch B transduced cells compared to non-transduced cells, confirming previous results. Batches B-S and UC also induced strong growth retardations. The impact on cell growth observed with batch C-S was lower than with batches B, B-S and UC, being just slightly more intense than with batch C.

Impact on the Transcriptome of Transduced Cells.

To explore underlying changes at the transcriptional level, these cells were collected 54 hours post-transduction. RNA were extracted and used for subsequent validation experiments.

Transcriptional Changes Observed at MOI 40.

RNA from MOI 40 transduced cells with batch B, C and B-S vectors and from NT cells were used to perform Agilent whole human genome microarrays. RNA levels from cells transduced with rLV-EF1-GFP batch B, C and B-S at MOI 40 were compared to RNA from non-transduced cells. After statistical analyses, probes upregulated or downregulated 1.5-fold or more were retained for each comparison.

Cell Cycle Genes Category.

Within downregulated probes for B vs NT and C vs NT, cell cycle probes are still predominant, with 209 probes on 496 downregulated probes for C vs NT, and 236 on 591 downregulated probes for B vs NT.

Probes corresponding to cell cycle genes previously selected on FIG. 5 as being downregulated with FC<=−3 with rLV-EF1 batch B at MOI150 vs NT, were still downregulated with rLV-EF1-GFP batch B and batch C at MOI40 (FIG. 14 and table 9). Except for 4 probes, the downregulation was stronger with batch B than with batch C, confirming the stronger impact on cell cycle with a non-highly purified vector batch.

Similarly, cell cycle upregulated genes corresponding to table 3 were still upregulated with the rLV-EF1-GFP vector batch B or batch C, as shown on FIG. 15 and table 9. This upregulation is stronger with batch B than batch C compared to NT, except for CDKN1A which exhibit a 1.6-fold upregulation with the 2 batches.

The 18 cell cycle genes selected in table 4 as candidate biomarkers exhibit a downregulation after transduction with rLV-EF1-GFP batch B as well as batch C vectors at MOI 40 compared to NT (NB: RRM2 is only downregulated with a −1.3 FC with batch C vs NT). The profile plot presented in FIG. 16 confirms a stronger downregulation of these genes with batch B compared to batch C. The proliferation marker MK167 is also represented in FIG. 16 and exhibit a more pronounced downregulation with batch B than with batch C compared to NT, confirming previous results.

Cell Cycle Genes Behavior with B-S Batch.

As shown on the profile plot presented in FIG. 17, downregulation of the 18 cell cycle genes from table 4 and MKI67 are similar with batch B-S compared to batch C (except for one gene: RRM2, which is downregulated in the same proportion with batches B and B-S, and nearly not impacted with batch C).

We can hypothesize that this last observation is linked to the presence of growth factors from the serum, which could be concentrated conjointly with the vector, and thwart the cell cycle genes downregulation, even if the cells are not growing as well as batch C transduced cells.

RT-qPCR Validations

RT-qPCR were performed on MKI67 and E2F8 cell cycle genes with three objectives:

1/validation of differential gene expressions obtained at MOI 40 for batches B, C and B-S on microarrays with an independent mRNA quantification technique, 2/validation of the specific behavior of these genes after transduction with another low quality batch: the UC batch, 3/confirmation of the downregulation of these 2 genes at MOI 150.

As presented in FIG. 18, for these 2 genes at MOI 40, a stronger downregulation with batch B compared to batch C was confirmed with respective FC compared to NT of −4.6 and −2.4 for MKI67, and −3.1 and −1.7 for E2F8. In agreement with microarrays' results, the downregulation was not higher with batch B-S than with batch C (FC −2.9 and −1.7 for MKI67 and E2F8 respectively). The UC batch produces the same downregulation level as B batch at this MOI (FC −4.7 for MKI67 and −3.0 for E2F8).

At MOI 150, downregulation for these 2 genes are stronger in each condition, but the ratio between batch B and batch C downregulations remains the same (approximately 2 fold). B-S batch generates an equivalent or lower downregulation than batch C, which is in agreement with FC obtained with microarrays. With UC batch, the downregulation reaches an intermediate level between those of batches B and C.

To conclude, we identified and validated a set of cell cycle genes that are early response genes in response to transduction and whose downregulation is stronger at the same MOI with a low quality vector produced without serum than with a highly purified vector. However, these genes cannot be used as unique quality biomarkers as they behave similarly with low quality batches produced with serum than with highly purified batches, certainly due to compensation mechanisms, through cell cycle genes activation by serum growth factors.

Genes Presenting a Batch Specific Behaviour

Among the 16 genes from table 6, only 2 were validated in this independent experiment as presenting a different behavior according to batch quality: CXCL2 and EREG.

Sequences of the primers used in the RT-qPCR validation are given in Table 10.

CXCL2 was significantly upregulated after transduction with B-S batch at MOI 40 (FC B-S vs NT: 1.9) although it was downregulated with batch C (FC C vs NT: −1.75). RT-qPCR validation experiments on the same samples (FIG. 19) confirm the downregulation with batch C, and show a slight upregulation with B-S compared to NT but it is not statistically significant. However, the UC batch exhibits a 1.6-fold upregulation compared to NT.

At MOI 150, RT-qPCR results shown in FIG. 19B, confirm a specific behavior of this gene depending on vector batch quality. Indeed, only low quality batches induce an upregulation of CXCL2, although the highly purified batch C provokes a slight downregulation of this gene (FC vs NT: 1.4). Noticeably, the B batch which induces no differential expression at MOI 40 (with even a slight downregulation), generates a strong upregulation at MOI 150. This could explain the different results observed with rLV-EF1 batch B which induced CXCL2 downregulation at MOI 40 and 150, maybe due to lower MOI, compared to rLV-EF1-GFP vector. Finally, at high MOI, CXCL2 upregulation appears to be specific of a low quality vector batch.

EREG exhibits a slight upregulation on microarrays with batches B (FC vs NT: 1.5) and B-S (FC vs NT: 1.4), and is not impacted with batch C. RT-qPCR validations were performed with RNA obtained from MOI 150 experiment (FIG. 19C). A strong and significant overexpression was confirmed with batches B and B-S (respective FC vs NT: 3.0 and 2.9), while the absence of impact after batch C transduction was confirmed. It can be noticed that UC batch does not induce a significant overexpression.

REFERENCES

Andreadis S T, Roth C M, Le Doux J M, Morgan J R, Yarmush M L. 1999. Large-scale processing of recombinant retroviruses for gene therapy. Biotechnol Prog 15(1): 1-11.

Banito A, Rashid S T, Acosta J C, Li S, Pereira C F, Geti I, Pinho S, Silva J C, Azuara V, Walsh M, Vallier L, Gil J. Senescence impairs successful reprogramming to pluripotent stem cells. Genes Dev. 2009 Sep. 15; 23(18):2134-9.

Baekelandt V, Eggermont K, Michiels M, Nuttin B, Debyser Z. Optimized lentiviral vector production and purification procedure prevents immune response after transduction of mouse brain. Gene Ther. 2003 November; 10(23): 1933-40.

Blagosklonny M V. Cell cycle arrest is not senescence. Aging (Albany N.Y.). 2011; 3(2):94.

Coffin J M, Hughes S H, Varmus H E (eds). Retroviruses. Cold Spring Harbor Laboratory Press, 1997.

Cartier, N., Hacein-Bey-Abina, S., et al., 2009. Hematopoietic Stem Cell Gene Therapy with a Lentiviral Vector in X-Linked Adrenoleukodystrophy. Science, 326(5954), p. 818-823.

Cavazzana-Calvo, Marina et al., 2010. Transfusion independence and HMGA2 activation after gene therapy of human β-thalassaemia. Nature, 467(7313), p. 318-322.

Coffin J M, Hughes S H, Varmus H E (eds). Retroviruses. Cold Spring Harbor Laboratory Press, 1997.

Chiu S C, Wang M J, Yang H H, Chen S P, Huang S Y, Chen Y L, Lin S Z, Ham H J, Pang C Y. Activation of NAG-1 via JNK signaling revealed an isochaihulactone-triggered cell death in human LNCaP prostate cancer cells. BMC Cancer. 2011; 11:146

Coppé J P, Desprez P Y, Krtolica A, Campisi J. The senescence-associated secretory phenotype: the dark side of tumor suppression. Annual Review of Pathological Mechanical Disease. 2010; 5:99-118.

Giri, M. S. et al., 2006. Microarray data on gene modulation by HIV-1 in immune cells: 2000-2006. Journal of Leukocyte Biology, 80(5), p. 1031-1043.

Kosar M, Bartkova J, Hubackova S, et al. Senescence-associated heterochromatin foci are dispensable for cellular senescence, occur in a cell type- and insult-dependent manner and follow expression of p16 ink4a. Cell Cycle. 2011; 10(3):457-468.

Mitchell, R., Chiang, C. Y., et al., 2003. Global analysis of cellular transcription following infection with an HIV-based vector. Molecular Therapy, 8(4), p. 674-687.

Li H, Collado M, Villasante A, Strati K, Ortega S, Cañamero M, Blasco M A, Serrano M. The Ink4/Arf locus is a barrier for iPS cell reprogramming. Nature. 2009 Aug. 27; 460(7259):1136-9. Epub 2009 Aug. 9.

Livak K J, Schmittgen T D. Analysis of relative gene expression data using real-time quantitative PCR and the 2(-Delta Delta C(T)) Method. Methods. 2001; 25(4):402-408.

Rimai L, Salmee I, Hart D, Liebes L, Rich M A, McCormick J J. 1975. Electrophoretic mobilities of RNA tumor viruses. Studies by Doppler-shifted light scattering spectroscopy. Biochemistry 14(21):4621-7.

Salmeen I, Rimai L, Liebes L, Rich M A, McCormick J J. 1975. Hydrodynamic diameters of RNA tumor viruses. Studies by laser beat frequency light scattering spectroscopy of avian myeloblastosis and Rauscher murine leukemia viruses. Biochemistry 14(1):134-41.

Selvaggi T A, Walker R E, Fleisher T A. Development of antibodies to fetal calf serum with arthus-like reactions in human immunodeficiency virus-infected patients given syngeneic lymphocyte infusions. Blood. 1997 Feb. 1; 89(3):776-9.

Sommer, C. A. et al., 2009. Induced Pluripotent Stem Cell Generation Using a Single Lentiviral Stem Cell Cassette. Stem Cells, 27(3), p. 543-549.

Takahashi K and Yamanaka S. Induction of pluripotent stem cells from mouse embryonic and adult fibroblast cultures by defined factors. Cell 126, 663-676, Aug. 25, 2006.

Vallier L, Touboul T, Brown S, Cho C, Bilican B, Alexander M, Cedervall J, Chandran S, Ahrlund-Richter L, Weber A, Pedersen R A. Signaling pathways controlling pluripotency and early cell fate decisions of human induced pluripotent stem cells. Stem cells, 2009, 27 (11): 2655-2666.

Young A R J, Narita M. SASP reflects senescence. EMBO Rep. 2009; 10(3):228-230.

Zhao, Y., Azam, S. & Thorpe, R., 2005. Comparative studies on cellular gene regulation by HIV-1 based vectors: implications for quality control of vector production. Gene therapy, 12(4), p. 311-319.

The invention claimed is:
1. A method for detecting and quantifying the cell response to transduction of a viral vector composition into eukaryotic target cells for further use in transgene transfer, comprising:
(a) hybridizing and/or amplifying a polynucleotide of at least one biomarker selected from the group consisting of CXCL2 (SEQ ID NO:1) and EREG (SEQ ID NO:2) with nucleic acid primers/probes, or binding of an antibody, or antigen binding fragment thereof, specific to the protein encoded by said at least one biomarker to detect and quantify the expression level of said at least one biomarker in target cells having no contact with the viral vector composition;
(b) separately transducing target cells with the viral vector composition and then either (i) hybridizing and/or amplifying a polynucleotide of at least one biomarker selected from the group consisting of CXCL2 (SEQ ID NO:1) and EREG (SEQ ID NO:2) with nucleic acid primers/probes, or (ii) binding of an antibody, or antigen binding fragment thereof to the protein encoded by said at least one biomarker, to detect and quantify the expression level of said at least one biomarker in the transduced target cells; and
(c) comparing the level of expression of said biomarker(s) in (b) to the level of expression of biomarker(s) in (a), wherein a significant upregulation in biomarker expression level in (b) relative to (a) indicates that the quality of the viral vector composition is insufficient transfer for further use in transgene transfer,
wherein the detection and quantification of the biomarker expression level are performed before the target cells reach confluency.

2. The method of claim 1, wherein a significant upregulation at high MOI is a two fold upregulation compared to (a).

3. The method of claim 1, further comprising the steps of:
(d) hybridizing and/or amplifying a polynucleotide of at least one further biomarker selected from the group consisting of ASPM (SEQ ID NO:3), AURKB (SEQ ID NO:4), CENPA (SEQ ID NO:5), CENPF (SEQ ID NO:6), CKS1B (SEQ ID NO:7), E2F8 (SEQ ID NO:8), ERCC6L (SEQ ID NO:9), FAM83D (SEQ ID NO:10), KIFC1 (SEQ ID NO:11), MKI67 SEQ ID NO:12), NEK2 (SEQ ID NO:13), NUSAP1 (SEQ ID NO:14), OIP5 (SEQ ID NO:15), PRC1 (SEQ ID NO:16), RRM2 (SEQ ID NO:17), SGOL1 (SEQ ID NO:18), SPC25 (SEQ ID NO:19), TOP2A (SEQ ID NO:20) and TTK (SEQ ID NO:21) with nucleic acid primers/probes, or binding of an antibody, or antigen binding fragment thereof, specific to the protein encoded by said at least one biomarker to detect and quantify the expression level of said at least one further biomarker in target cells having no contact with the viral vector composition;
(e) separately transducing target cells with the viral vector composition and then either (i) hybridizing and/or amplifying a polynucleotide of said at least one further biomarker of (d) with nucleic acid primers/probes, or (ii) binding of an antibody, or antigen binding fragment thereof to the protein encoded by said at least one further biomarker, to detect and quantify the expression level of said at least one further biomarker in the transduced target cells; and
(f) comparing the level of expression of said further biomarker(s) in (e) to the level of expression of said further biomarker(s) in (d), wherein a significant downregulation in biomarker expression level in (e) relative to (d) indicates that the quality of the viral vector composition is insufficient for further use in transgene transfer.

4. The method of claim 3, wherein a significant downregulation at optimal MOI is a 1.5 fold downregulation compared to (d).

5. The method of claim 1, further comprising of the steps of:
(g) separately transducing target cells with a control viral vector composition and then either (i) hybridizing and/or amplifying a polynucleotide of at least one biomarker selected in the group consisting of CXCL2 (SEQ ID NO:1) and EREG (SEQ ID NO:2) with nucleic acid primers/probes, or (ii) binding of an antibody, or antigen binding fragment thereof to the protein encoded by said at least one biomarker, to detect and quantify the expression level of said at least one biomarker in the target cells transduced with the control viral vector composition; and
(h) comparing the level of expression of said biomarker(s) in (g) to the level of expression of biomarker(s) in (a), wherein no significant differential expression in biomarker(s) in (g) relative to (a) is confirmation that the quality of the viral vector composition is insufficient for further use in transgene transfer.

6. The method of claim 1, further comprising the steps of:
(j) separately transducing target cells with a control viral vector composition and then either (i) hybridizing and/or amplifying a polynucleotide of at least one further biomarker selected in the group consisting of ASPM (SEQ ID NO:3), AURKB (SEQ ID NO:4), CENPA (SEQ ID NO:5), CENPF (SEQ ID NO:6), CKS1B (SEQ ID NO:7), E2F8 (SEQ ID NO:8), ERCC6L (SEQ ID NO:9), FAM83D (SEQ ID NO:10), KIFC1 (SEQ ID NO:11), MKI67 (SEQ ID NO:12), NEK2 (SEQ ID NO:13), NUSAP1 (SEQ ID NO:14), OIP5 (SEQ ID NO:15), PRC1 (SEQ ID NO:16), RRM2 (SEQ ID NO:17), SGOL1 (SEQ ID NO:18), SPC25 (SEQ ID NO:19), TOP2A (SEQ ID N:20) and TTK (SEQ ID N:21) with nucleic acid primers/probes, or (ii) binding of an antibody, or antigen binding fragment thereof to the protein encoded by said at least one further biomarker, to detect and quantify the expression level of said at least one further biomarker in the target cells transduced with the control viral vector composition; and
(k) comparing the level of expression of said further biomarker(s) in (j) to the the level of expression of said further biomarker(s) in (d), wherein a potential downregulation in biomarker expression level in (j) relative to (d) is confirmation that the quality of the viral vector composition is insufficient for further use in transgene transfer.

7. The method of claim 6, wherein the potential downregulation in biomarker expression level in (j) compared to (d) is at least 1.5 times less than the downregulation in biomarker expression level in (e) compared to (d) at high MOI.

8. The method of claim 5, comprising beforehand a step of titration of the viral vector composition and the control viral vector composition.

9. The method of claim 1, wherein target cells are eukaryotic cells and the viral composition for transducing target cells is a lentiviral vector composition.

* * * * *

SEQUENCE LISTING

```
<160> NUMBER OF SEQ ID NOS: 37

<210> SEQ ID NO 1
<211> LENGTH: 1234
<212> TYPE: DNA
<213> ORGANISM: Homo sapiens

<400> SEQUENCE: 1
gagctccggg aatttccctg gcccgggact ccgggctttc cagccccaac catgcataaa    60
aggggttcgc cgttctcgga gagccacaga gcccgggcca caggcagctc cttgccagct   120
ctcctcctcg cacagccgct cgaaccgcct gctgagcccc atggcccgcg ccacgctctc   180
cgccgccccc agcaatcccc ggctcctgcg ggtggcgctg ctgctcctgc tcctggtggc   240
cgccagccgg cgcgcagcag gagcgcccct ggccactgaa ctgcgctgcc agtgcttgca   300
gaccctgcag ggaattcacc tcaagaacat ccaaagtgtg aaggtgaagt cccccggacc   360
ccactgcgcc caaaccgaag tcatagccac actcaagaat gggcagaaag cttgtctcaa   420
ccccgcatcg cccatggtta agaaaatcat cgaaaagatg ctgaaaaatg gcaaatccaa   480
ctgaccagaa ggaaggagga agcttattgg tggctgttcc tgaaggaggc cctgccctta   540
caggaacaga agaggaaaga gagacacagc tgcagaggcc acctggattg cgcctaatgt   600
gtttgagcat cacttaggag aagtcttcta tttatttatt tatttattta tttgtttgtt   660
ttagaagatt ctatgttaat atttatgtg taaaataagg ttatgattga atctacttgc   720
acactctccc attatattta ttgtttattt taggtcaaac ccaagttagt tcaatcctga   780
ttcatattta atttgaagat agaaggtttg cagatattct ctagtcattt gttaatattt   840
cttcgtgatg acatatcaca tgtcagccac tgtgatagag gctgaggaat ccaagaaaat   900
ggccagtgag atcaatgtga cggcagggaa atgtatgtgt gtctattttg taactgtaaa   960
gatgaatgtc agttgttatt tattgaaatg atttcacagt gtgtggtcaa catttctcat  1020
gttgaagctt taagaactaa aatgttctaa atatcccttg gacattttat gtctttcttg  1080
taaggcatac tgccttgttt aatgttaatt atgcagtgtt tccctctgtg ttagagcaga  1140
gaggtttcga tatttattga tgttttcaca aagaacagga aaataaaata tttaaaaata  1200
taaaaaaaaa aaaaaaaaa aaaaaaaaa aaaa                                1234
```

<210> SEQ ID NO 2
<211> LENGTH: 4628
<212> TYPE: DNA
<213> ORGANISM: Homo sapiens

<400> SEQUENCE: 2

```
tcacttgcct gatatttcca gtgtcagagg gacacagcca acgtggggtc ccttctaggc      60
tgacagccgc tctccagcca ctgccgcgag cccgtctgct cccgccctgc ccgtgcactc     120
tccgcagccg ccctccgcca agccccagcg cccgctccca tcgccgatga ccgcggggag     180
gaggatggag atgctctgtg ccggcagggt ccctgcgctg ctgctctgcc tgggtttcca     240
tcttctacag gcagtcctca gtacaactgt gattccatca tgtatcccag gagagtccag     300
tgataactgc acagctttag ttcagacaga agacaatcca cgtgtggctc aagtgtcaat     360
aacaaagtgt agctctgaca tgaatggcta ttgtttgcat ggacagtgca tctatctggt     420
ggacatgagt caaaactact gcaggtgtga agtgggttat actggtgtcc gatgtgaaca     480
cttcttttta accgtccacc aacctttaag caaagaatat gtggctttga ccgtgattct     540
tattattttg tttcttatca cagtcgtcgg ttccacatat tatttctgca gatggtacag     600
aaatcgaaaa agtaaagaac caagaaggaa atatgagaga gttacctcag gggatccaga     660
gttgccgcaa gtctgaatgg cgccatcaaa cttatgggca gggataacag tgtgcctggt     720
taatattaat attcccattt tattaataat atttatgttg ggtcaagtgt taggtcaata     780
acactgtatt ttaatgtact tgaaaaatgt ttttattttt gttttatttt tgacagacta     840
tttgctaatg tataatgtgc agaaaatatt taatatcaaa agaaaattga tatttttata     900
caagtaattt cctgagctaa atgcttcatt gaaagcttca agtttatat gcctggtgca      960
cagtgcttag aagtaagcaa ttcccaggtc atagctcaag aattgttagc aaatgacaga    1020
tttctgtaag cctatatata tagtcaaatc gatttagtaa gtatgttttt tatgttcctc    1080
aaatcagtga taattggttt gactgtacca tggtttgata tgtagttggc accatggtat    1140
catatattaa aacaataatg caattagaat ttgggagaag caaatatagg tcctgtgtta    1200
aacactacac atttgaaaca agctaacct ggggagtcta tggtctcttc actcaggtct    1260
cagctataat tctgttatat gaggggcagt ggacagttcc ctatgccaac tcacgactcc    1320
tacaggtact agtcactcat ctaccagatt ctgcctatgt aaaatgaatt gaaaacaat    1380
tttctgtaat cttttattta agtagtgggc atttcatagc ttcacaatgt tcctttttg    1440
tatattacaa catttatgtg aggtaattat tgctcaacag acaattagaa aaagtccac    1500
acttgaagcc taaatttgtg ctttttaaga atatttttag actatttctt tttatagggg    1560
ctttgctgaa ttctaacatt aaatcacagc ccaaaatttg atggactaat tattatttta    1620
aaatatatga agacaataat tctacatgtt gtcttaagat ggaaatacag ttatttcatc    1680
ttttattcaa ggaagtttta actttaatac agctcagtaa atggcttctt ctagaatgta    1740
aagttatgta tttaaagttg tatcttgaca caggaaatgg gaaaaaactt aaaaattaat    1800
atggtgtatt tttccaaatg aaaaatctca attgaaagct tttaaaatgt agaaacttaa    1860
acacaccttc ctgtggaggc tgagatgaaa actagggctc atttttcctga catttgttta    1920
ttttttggaa gagacaaaga tttcttctgc actctgagcc cataggtctc agagagttaa    1980
taggagtatt tttgggctat tgcataagga gccactgctg ccaccacttt tggatttat     2040
gggaggctcc ttcatcgaat gctaaaacctt tgagtagagt ctccctggat cacataccag    2100
```

```
gtcagggagg atctgttctt cctctacgtt tatcctggca tgtgctaggg taaacgaagg    2160
cataataagc catggctgac ctctggagca ccaggtgcca ggacttgtct ccatgtgtat    2220
ccatgcatta tataccctgg tgcaatcaca cgactgtcat ctaaagtcct ggccctggcc    2280
cttactatta ggaaaataaa cagacaaaaa caagtaaata tatggtca tatacatatt     2340 gtatatatat tcatatacaa acatgtatgt atacatgacc ttaatggatc atagaattgc   2400
agtcatttgg tgctctgcta accatttata taaaacttaa aaacaagaga aagaaaaat    2460 caattagatc taaacagtta tttctgtttc ctatttaata cagctgaagt caaaatatgt   2520
aagaacacat tttaaatact ctacttacag ttggccctct gtggttagtt ccacatctgt   2580
ggattcaacc aaccaaggac ggaaaatgct taaaaataa tacaacaaca acaaaaaata   2640
cattataaca actatttact tttttttttt tcttttttgag atggagtctc gctctgttgc  2700
ccaggttgga gtgcagtggc acgatctcgg ctcactgcaa cctcacctcc cgggttcaag   2760
agatcctcct gcctcagcct cctgagcagc tgggactaca ggcgcatgcc accatgccca   2820
gctaattttt gtattttag tagaggcggg gtttcaccat gttggccagg atggtctcaa    2880
tctcctaacc ttgagatcca ccctccacag cctcccaaac tgctgggatt acaggtgtga   2940
gccaccgcac gtagcattta cattaggtat tacaagtaat gtaaagatga tttaagtata   3000
caggaggatg tgaataggtt atatgcaagc actatgccct tttatataag tgacttgaac   3060
atctgtgccc gattttagta tgtgcagggg ggcgatctgg gaatcagtcc cctgtggata  3120
ccaaggtaca actgtattta ttaacgctta ctagatgtga ggagagtctg aatattttca   3180
gtgatcttgg ctgtttcaaa aaatctatt gacttttcaa taaatcagct gcaatccatt    3240 tatttcatt acaaaagatt tattgtaagc atctcaatct tggtttgtca gtttatctta    3300
agcatgtcaa ttcataaaaa caagtcattt ttgtattttt catctttaag aatgcttaaa   3360
aaagctaatc cctaaaatag ttagatcttt gtaaatgcat attaaataat aaagtatgac   3420
ccacattact ttttatgggt gaaaataaga caaaaataat agttttagtg aggatggtgc   3480
tgagtaaaca taaaaactga tttgctctca gctgatgtgt cctgtacaca gtgggaagat   3540
tttagttcac acttagtcta actcccccat tttacagatt tctcactata tatatttcta   3600
gaaggggcta tgcatattca atgtattgag aaccaaagca accacaaatg cataaatgca   3660
taatttatgg tcttcaacca aggccacata ataacccagt taacttactc tttaaccagg   3720
aatattaagt tctataacta gtactcaagg tttaacctta aaattaagat tccttaacc    3780 ttaaccttaa aattgatatt atattaaaca tacataatac aatgtaactc cactgttctc   3840
ctgaatattt tttgctctaa tctctctgcc gaaagtcaaa gtgatgggag aattggtata   3900
ctggtatgac tacgtcttaa gtcagatttt tatttatgag tctttgagac taaattcaat   3960
caccaccagg tatcaaatca actttatgc agcaaatata tgattctagt gtctgacttt   4020
tgttaaattc agtaatgcag tttttaaaaa cctgtatctg acccactttg taattttgc    4080 tccaatatcc attctgtaga cttttgaaaa aaaagttttt aatttgatgc ccaatatatt   4140
ctgaccgtta aaaaattctt gttcatatgg gagaagggg agtaatgact tgtacaaaca   4200
gtatttctgg tgtatatttt aatgttttta aaaagagtaa tttcatttaa atatctgtta   4260
ttcaaatttg atgatgttaa atgtaatata atgtattttc ttttattttt gcactctgta   4320
attgcacttt ttaagtttga agagccattt tggtaaacgg ttttattaa agatgctatg    4380 gaacataaag ttgtattgca tgcaatttga agtaacttat ttgactatga atgttatcgg   4440
attactgaat tgtatcaatt tgtttgtgtt caatatcagc tttgataatt gtgtacctta   4500
```

```
agatattgaa ggagaaaata gataatttac aagatattat taattttat ttatttttct      4560 tgggaattga aaaaaattga aataaataaa aatgcattga acatcttgca ttcaaaatct      4620
tcactgac                                                              4628

<210> SEQ ID NO 3
<211> LENGTH: 10906
<212> TYPE: DNA
<213> ORGANISM: Homo sapiens

<400> SEQUENCE: 3
attggtggag gcggcaagtt taaacagagt caaaacgcca tacttgtttg gctcctcttt        60
ttaatttgcg agtttattgg gcttgttttc tgttttctag ggagtaggtt agtggaaaag       120
aaaaagggcc gaattcactc ccacgacctc tacagccgcc cctgagggga agcggtcagc       180
gtaagtcccg gatccccgct ccggagccgc ctcgtgggag cggggcaagg agatccagga       240
ggggtctcga atctgccatg gcgaaccggc gagtggggcg aggctgctgg gaagtgagcc       300
cgaccgagcg gaggccgccc gcggggctgc ggggccccgc ggccgaggag gaggcgtctt       360
ccccgccggt cctgtctctc agccacttct gcaggtctcc tttcctttgc ttcggggacg       420
ttctcctggg agcctcacgg acgctgtctc tggccctaga caaccctaac gaggaggtgg       480
cagaagtgaa gatctcccac ttcccggccg cggacctggg cttcagtgtg tcgcagcgct       540
gtttcgtgtt gcagcctaaa gagaaaattg ttatttctgt taactggaca ccactcaaag       600
aaggccgagt aagagagatt atgacatttc ttgtaaatga tgttctgaaa caccaagcta       660
tattactagg aaatgcagaa gagcagaaaa agaaaaagag gagtctttgg gataccatta       720 aaagaagaa aatttcagcc tctacaagtc acaacagaag ggtttcaaat attcagaatg       780
ttaataaaac atttagtgtt tcccaaaaag ttgacagagt taggagccca ctacaagctt       840
gtgaaaactt ggctatgaat gaaggcggtc ccccaacaga aaacaattct ttaatacttg       900
aagaaaataa aatacccata tcacctatta gccctgcttt caatgaatgc catggtgcaa       960
cttgcttgcc actctctgta cgtcgatcta ctacctactc atctcttcat gcatcagaaa      1020
atagggaact attaaatgta cacagtgcca acgtttcaaa agtttcttt aatgagaaag       1080 ctgtaactga aacttccttt aattccgtaa atgttaatgg ccaaagagga gagaatagta      1140
aacttagtct taccccccaac tgttcttcaa cttttgaacat tacacaaagc caaatacatt      1200
ttctaagtcc agattctttt gtaaataata gtcatggagc taataatgaa ctagaattag       1260
taacatgtct ttcatcagat atgtttatga agataattc acagcctgtg catttggaat       1320
caacaattgc acatgaaatt tatcagaaaa ttttaagtcc agattctttc ataaaagata       1380 attatgact aaatcaggat ctagaatcag agtcagttaa tcctatttta tcccctaatc        1440 aattttttaaa agataacatg gcatatatgt gtacatctca gcaaacatgt aaagtaccat      1500
tatcaaatga aaattctcaa gtcccacagt ctcctgaaga ttggagaaaa agtgaagttt      1560
cgccacgtat tcctgaatgt cagggttcaa aatctcccaa agctattttt gaagaactag      1620
tagaaatgaa gtcaaattac tacagtttta taaaacaaaa taatcctaaa ttttctgcag      1680
ttcaggatat ttctagtcat agccacaata aacaacctaa gagacgtcca atactttctg      1740
ccactgttac taaaaggaag gccacctgta ccagagaaaa ccaaactgag attaataaac      1800
caaaagcaaa aagatgtctc aacagtgcag tgggtgaaca tgaaaaagta ataaataatc      1860
aaaaggaaaa agaagatttt cattcttatc ttccaattat agatccaata ttaagtaaat      1920
```

-continued

```
ctaagagtta taaaaacgag gtaacaccct cttcgacaac agcttcagtt gctcggaaaa    1980
gaaagagcga tggaagcatg gaagatgcaa atgtgagagt tgcaattaca gaacatacag    2040
aagtgcgaga aatcaaaaga atccattttt ctccctcaga gcctaaaaca tcagctgtta    2100
agaaaacaaa aaatgtgaca acacccatct caaaacgtat tagcaacaga gagaaattaa    2160
acctgaagaa gaaaactgat ttatcaatat tcagaactcc aatttctaaa acaaacaaaa    2220
ggacaaaacc cattatcgct gtggcacagt ccagtttgac cttcataaaa ccattaaaaa    2280
cagatattcc cagacacccg atgccatttg ctgcaaaaaa catgttttat gatgaacgct    2340
ggaaggaaaa gcaggaacag ggcttcactt ggtggttaaa ttttatatta accccctgatg   2400 acttcactgt aaaaacaaat atttctgaag taaatgctgc tactcttctt ttgggaatag    2460
agaatcaaca taaataagt gttcctagag cacctacaaa agaggaaatg tctctcagag    2520
cttatactgc tcggtgtagg ttaaacagac tacgtcgtgc agcatgccgt ttgtttactt    2580
ctgaaaaaat ggttaaagct attaaaaagc ttgaaattga aattgaagct aggcggttaa    2640
ttgttcgaaa agatagacac ctatggaaag atgtgggaga acgtcagaaa gtcctgaatt    2700
ggctgttgtc ctacaatcct ttgtggcttc gaattggtct agagacaact tatggagaac    2760
tcatatcttt ggaagataac agtgatgtca cagggttggc tatgtttatt ctgaatcgcc    2820
tactttggaa tcctgatata gcagctgagt atagacaccc cactgttcct cacctgtata    2880
gagatggtca tgaagaagct ttgtccaagt ttacattgaa aaagttattg ttgttggtct    2940
gttttcttga ttatgctaaa atttccagac tcattgatca tgatccttgt ctcttctgta    3000
aagatgccga attcaaggct agtaaagaaa tccttttggc tttttcacga gatttcctaa    3060
gtggtgaagg tgacctttcc cgtcacccttg gcttattggg attacctgtt aaccatgttc    3120
agacaccatt tgatgaattt gattttgccg ttacaaatct tgccgtagac ttgcaatgtg    3180
gagtgcgcct tgtgcgaacc atggaacttc tcacacagaa ctgggacctc tcaaagaaac    3240
tcaggattcc ggcaataagt cgtcttcaaa agatgcacaa tgttgacatt gttcttcaag    3300
ttcttaaatc acgaggaatt gaattaagtg atgagcatgg aaatacaatt ctatctaagg    3360
atattgtgga taggcacaga gaaaaaactc tcaggttgct ttggaaaata gcgtttgctt    3420
ttcaggtgga tatttcccctt aacttagatc aattaaagga agaaattgcc tttctaaaac    3480
acacaaagag tataagaaaa acaatatctc tactatcatg ccattctgat gatcttatta    3540
ataagaaaaa aggcaaaagg gatagtggtt cctttgaaca atatagtgaa aacataaagt    3600
tattgatgga tgggtaaat gctgtttgtg ccttctataa taaaaggtg gagaattta    3660 cagtgtcttt ctcagacggc cgtgtgttat gttacctgat ccaccattac catccttgct    3720
atgtgccatt tgacgctata tgtcagcgta ctactcaaac tgtggaatgt acgcaaactg    3780
gttcagtggt attaaattca tcatctgaat ctgatgacag ttctctggat atgtctctta    3840
aagcatttga tcatgaaaat acttcagagc tatacaaaga gctcctagaa aatgaaaaga    3900 aaaatttttca cttggttagg tctgcagtta gagaccttgg tggaatacct gctatgatta    3960
atcattcaga tatgtcaaat acaattccag atgaaaaggt ggttattacc tatttgtcat    4020
ttctttgtgc aaggctttttg gatcttcgta aagaaataag agctgctcga ctcatacaaa    4080
caacatggag aaaatataaa ctaaaaacag atctcaaacg ccatcaggag agagagaaag    4140
ctgcaagaat tattcaattg gctgtaatca attttctagc aaaacaaaga ttgagaaaaa    4200
gagttaatgc agcactcgtc attcagaaat attggcgaag agtcttagca cagagaaaat    4260
tattaatgtt aaaaaaggaa aagctggaaa aagttcaaaa taaagcagca tcacttattc    4320
```

```
agggatattg gagaagatat tccactagac aaagatttct gaaattgaaa tattattcaa    4380
tcatcctgca atctaggata agaatgataa ttgctgttac atcttataaa cgatatcttt    4440
gggctacagt tacaattcag aggcattggc gtgcttattt aagaagaaaa caagatcaac    4500
aaagatatga aatgctaaaa tcatcaactc ttataatcca atctatgttc agaaaatgga    4560
agcaacgtaa aatgcaatca caagtaaaag ctacagtaat attgcaaaga gcttttagag    4620
aatggcattt aagaaaacaa gctaaagaag aaaattctgc tattatcata caatcatggt    4680
atagaatgca taaagaatta cggaaatata tttatattag atcttgtgtt gttatcattc    4740
agaaaagatt tcggtgcttt caagcccaaa agttatataa aagaagaaaa gagtccatac    4800
taaccatcca gaagtactac aaagcatatc tgaaaggaaa gattgagcgc accaactatt    4860
tgcagaaacg agctgcagcc attcaattac aagctgcttt taggagactg aaagctcata    4920
atttatgtag acaaattaga gctgcttgtg ttattcagtc atactggaga atgagacaag    4980
acagagttcg attttaaaac cttaagaaga ctattatcaa atttcaggca catgtaagaa    5040
aacatcaaca acgacagaaa tataagaaga tgaagaaagc agctgttata attcagactc    5100
atttccgagc ttatattttt gccatgaaag ttctagcatc ttaccagaaa acacgctctg    5160
ctgtcattgt gctgcagtct gcatatagag ggatgcaagc caggaaaatg tatattcaca    5220
tcctcacatc tgttataaag attcaatcat attatcgtgc ttatgtttct aaaaaggaat    5280
ttttgagcct aaaaaatgct acaataaaat tgcagtcaac tgttaagatg aaacaaacac    5340
gtaaacaata tttgcattta agagcagctg cactatttat ccagcaatgt taccgttcca    5400
aaaaaatagc tgcacaaaag agagaagagt atatgcagat gcgggaatct tgtatcaaac    5460
tgcaagcatt tgttagagga taccttgtcc gaaagcagat gaggttacaa agaaaagctg    5520
ttatttcact acagtcttat ttcagaatga aaaggctcg gcagtattat ctgaaaatgt    5580
ataaagcaat tattgtcatt cagaattact atcatgcata caaagcacag gtcaatcaga    5640
ggaagaactt cttgcaagtc aaaaaagcag ctacttgctt gcaagcagct tacagaggtt    5700
ataaagtacg ccagctaatc aaacaacaat ctatagctgc tcttaaaatt cagtctgctt    5760
ttagaggcta taataaaagg gtaaaatatc aatctgtgct tcaatctata ataaagattc    5820
agagatggta cagggcgtac aagactcttc atgatacaag aacacatttt ttgaagacaa    5880
aggcagctgt gatttccctc cagtctgctt atcgtggctg gaaggttcgg aaacagatta    5940
gaagggaaca tcaagctgcc ttgaagattc agtctgcttt tagaatggcc aaggcccaga    6000
aacagtttag attgtttaaa acagcagcat tagtcatcca gcaaaatttc agagcatgga    6060
ctgcaggaag gaagcaatgt atggagtata ttgaactccg tcatgcggta ctggtgcttc    6120
aatctatgtg gaagggaaaa acactgagaa gacagcttca aaggcaacat aaatgtgcta    6180
tcatcataca gtcatactat agaatgcatg tgcaacaaaa gaagtggaaa atcatgaaaa    6240
aagctgctct tctgattcaa aagtattata gggcttacag tattggaaga gaacagaatc    6300
atttatattt gaaaacaaaa gcagctgtag taactttaca gtcagcttat cgtggtatga    6360
aagtgagaaa aagaataaag gattgcaaca aagcagcagt cactatacag tctaaataca    6420
gagcttacaa aaccaaaaag aaatatgcaa cctatagagc ttcagctatt ataattcaga    6480
gatggtatcg aggtattaaa attacaaacc atcagcataa ggagtatctt aatttgaaga    6540
agacagcaat taaatccaa tctgttttata gaggttattag agttagaaga catattcaac    6600
acatgcacag ggcagccact tttattaaag ccatgtttaa aatgcatcag tcaagaataa    6660
```

```
gttaccatac aatgagaaaa gcagctattg ttattcaagt aagatgtaga gcatattatc    6720
aaggtaaaat gcagcgtgaa aagtacctga caattttgaa agctgttaaa gtccttcagg    6780
caagttttag aggagtaaga gttagacgga ctcttagaaa gatgcagact gcagcaacac    6840
tcattcagtc aaactacaga agatacagac agcaaacata ctttaataag ttaaagaaaa    6900
taacaaaaac agtacagcaa agatactggg caatgaaaga aagaaacata caatttcaaa    6960
ggtataacaa actgaggcat tctgtaatat acattcaggc tattttagg ggaaagaaag     7020 ctagaagaca tttaaaaatg atgcatatag ccgcaactct cattcagagg agatttagaa    7080
ctctaatgat gagaagaaga ttcctctctc tcaagaaaac tgctattttg attcagagaa    7140
aatatcgggc acatctttgt acaaagcatc acttacagtt ccttcaggta caaaatgcag    7200
ttattaaaat ccagtcatca tacagaagat ggatgataag gaaaaggatg cgagagatgc    7260
acagggctgc tactttcatc cagtctactt tcagaatgca cagattacat atgagatatc    7320
aggctttgaa acaggcctcc gttgtgatcc aacagcaata ccaagcaaat agagctgcaa    7380
aactgcagag gcagcattat ctcagacaaa gacactctgc tgtgatcctt caggctgcat    7440
tcaggggtat gaaaactaga agacatttga agagtatgca ttcctctgca acccttattc    7500
agagtaggtt tagatcatta ctggtgagga gaagattcat ttccctcaaa aaagctacta    7560
tttttgttca gaggaaatat cgagccacca tttgtgccaa acataaattg taccaattct    7620
tgcacttaag aaaggcagcc attacaatac agtcatctta cagaagactg atggtaaaga    7680
agaagttaca agaaatgcaa agggctgcag ttctcattca ggctactttc aggatgtaca    7740
gaacatatat tacatttcag acttggaaac atgcttcaat tctaattcag caacattatc    7800
gaacatatag agctgcaaaa ttacaaagag aaaattatat cagacaatgg cattctgctg    7860
tggttattca ggctgcatat aaaggaatga aagcaagaca acttttaagg gaaaaacaca    7920
aagcttctat cgtaatacaa agcacctaca gaatgtatag gcagtattgt ttctaccaaa    7980
agcttcagtg ggctacaaaa atcatacaag aaaaatatag agcaaataaa agaaacaga     8040 aagtatttca acacaatgaa cttaagaaag agacttgtgt tcaggcaggt tttcaggaca    8100
tgaacataaa aaaacagatt caggaacagc accaggctgc cattattatt cagaagcatt    8160
gtaaagcctt taaataagg aagcattatc tccaccttag agcaacagta gtttctattc      8220
aaagaagata cagaaaacta actgcagtgc gtacccaagc agttatttgt atacagtctt    8280
attacagagg ctttaaagta cgaaaggata ttcaaaatat gcaccgggct gccacactaa    8340
ttcagtcatt ctatcgaatg cacagggcca aagttgatta tgaaacaaag aaaactgcaa    8400
ttgtggttat acagaattat tataggttgt atgttagagt aaaaacagaa agaaaaaact    8460
ttttagcagt tcagaaatct gtacgaacta ttcaggctgc ttttagaggc atgaaagtta    8520
gacaaaaatt gaaaaatgta tcagaggaaa agatggcagc cattgttaac caatctgcac    8580
tctgctgtta cagaagtaaa actcagtatg aagctgttca aagtgaaggt gttatgattc    8640
aagagtggta taagcttct ggccttgctt gttcacagga agcagagtat cattctcaaa      8700
gtagggctgc agtaacaatt caaaaagctt tttgtagaat ggtcacaaga aaactggaaa    8760
cacagaaatg tgctgcccta cggattcagt tcttccttca gatggctgtg tatcggagaa    8820
gatttgttca gcagaaaaga gctgctatca ctttacagca ttattttagg acgtggcaaa    8880
ccagaaaaca gttttactta tatagaaaag cagcagtggt tttacaaaat cactacagag    8940
catttctgtc tgcaaaacat caaagacaag tctatttaca gatcagaagc agtgttatca    9000
ttattcaagc tagaagtaaa ggatttatac agaaacggaa gtttcaggaa attaaaaata    9060
```

```
gcaccataaa aattcaggct atgtggagga gatatagagc caagaaatat ttatgtaaag    9120
tgaaagctgc ctgcaagatt caagcctggt atagatgttg gagagcacac aaagaatatc    9180
tagctatatt aaaagctgtt aaaattattc aaggttgctt ctataccaaa ctagagagaa    9240
cacggttttt gaatgtgaga gcatcagcaa ttatcattca gagaaaatgg agagctatac    9300
ttcctgcaaa gatagctcat gaacacttct taatgataaa aagacatcga gctgcttgtt    9360
tgatccaagc acattataga ggatataaag gaaggcaggt cttttcttcgg cagaaatctg    9420 ctgctttgat catacaaaaa tatatacgag ccagggaggc tggaaagcat gaaaggataa    9480
aatatattga atttaaaaaa tctacagtta tcctacaagc actggtgcgt ggttggctag    9540
tacgaaaaag attttttagaa cagagagcca aaattcgact tcttcacttc actgcagctg    9600
catattatca cctgaatgct gttagaattc aaagagccta taaactttac ctggctgtga    9660
agaatgctaa caagcaggtt aattcagtca tctgtattca gagatggttt cgagcaagat    9720
tacaagaaaa gagatttatt cagaaatatc atagcatcaa aaagattgag catgaaggtc    9780
aagaatgtct gagccagcga aatagggctg catcagtaat acagaaagca gtgcgccatt    9840
ttctcctccg taaaaagcag gaaaaattca ctagtggaat cattaaaatt caggcattat    9900
ggagaggcta ttcttggagg aagaaaaatg attgtacaaa aattaaagct atacgactaa    9960
gtcttcaagt tgttaatagg gagattcgag aagaaaacaa actctacaaa agaactgcac   10020
ttgcacttca ttaccttttg acatataagc acctttctgc cattcttgag gccttaaaac   10080
acctagaggt agttactaga ttgtctccac tttgttgtga aacatggcc cagagtggag    10140 caatttctaa aatatttgtt ttgatccgaa gttgtaatcg cagtattcct tgtatggaag   10200
tcatcagata tgctgtgcaa gtcttgctta atgtatctaa gtatgagaaa actacttcag   10260
cagtttatga tgtagaaaat tgtatagata tactattgga gcttttgcag atataccgag   10320
aaaagcctgg taataaagtt gcagacaaag gcggaagcat ttttacaaaa acttgttgtt   10380
tgttggctat tttactgaag acaacaaata gagcctctga tgtacgaagt aggtccaaag   10440
ttgttgaccg tatttacagt ctctacaaac ttacagctca taaacataaa atgaatactg   10500
aaagaatact ttacaagcaa aagaagaatt cttctataag cattccttt atcccagaaa    10560 cacctgtaag gaccagaata gtttcaagac ttaagccaga ttgggttttg agaagagata   10620
acatggaaga aatcacaaat cccctgcaag ctattcaaat ggtgatggat acgcttggca   10680
ttccttatta gtaaatgtaa acattttcag tatgtatagt gtaaagaaat attaaagcca   10740
atcatgagta cgtaaagtga ttttttgctct ccgtgtacaa cttttaaaat ctgactttgt   10800
tttaaaaaaa cataaactgt tcattacatt cttcattttt atcatttata gttttatgca   10860
tgtaataaac taatatgtca taagatgaaa aaaaaaaaa aaaaaa                    10906
```

<210> SEQ ID NO 4
<211> LENGTH: 1314
<212> TYPE: DNA
<213> ORGANISM: Homo sapiens

<400> SEQUENCE: 4

```
cggggcggga gatttgaaaa gtccttggcc agggcgcggc gtggcagatt cagttgtttg      60
cgggcggccg ggagagtagc agtgccttgg accccagctc tcctccccct ttctctctaa     120
ggatggccca gaaggagaac tcctacccct ggccctacgg ccgacagacg gctccatctg    180
gcctgagcac cctgccccag cgagtcctcc ggaaagagcc tgtcacccca tctgcacttg    240
```

| | |
|---|---|
| tcctcatgag ccgctccaat gtccagccca cagctgcccc tggccagaag gtgatggaga | 300 |
| atagcagtgg gacacccgac atcttaacgc ggcacttcac aattgatgac tttgagattg | 360 |
| ggcgtcctct gggcaaaggc aagtttggaa acgtgtactt ggctcgggag aagaaaagcc | 420 |
| atttcatcgt ggcgctcaag gtcctcttca agtcccagat agagaaggag ggcgtggagc | 480 |
| atcagctgcg cagagagatc gaaatccagg cccacctgca ccatcccaac atcctgcgtc | 540 |
| tctacaacta tttttatgac cggaggagga tctacttgat tctagagtat gcccccgcg | 600 |
| gggagctcta caaggagctg cagaagagct gcacatttga cgagcagcga acagccacga | 660 |
| tcatggagga gttggcagat gctctaatgt actgccatgg gaagaaggtg attcacagag | 720 |
| acataaagcc agaaaatctg ctcttagggc tcaagggaga gctgaagatt gctgacttcg | 780 |
| gctggtctgt gcatgcgccc tccctgagga ggaagacaat gtgtggcacc ctggactacc | 840 |
| tgcccccaga gatgattgag gggcgcatgc acaatgagaa ggtggatctg tggtgcattg | 900 |
| gagtgctttg ctatgagctg ctggtgggga acccaccctt tgagagtgca tcacacaacg | 960 |
| agacctatcg ccgcatcgtc aaggtggacc taaagttccc cgcttccgtg cccatgggag | 1020 |
| cccaggacct catctccaaa ctgctcaggc ataaccctc ggaacggctg cccctggccc | 1080 |
| aggtctcagc ccacccttgg gtccgggcca actctcggag ggtgctgcct ccctctgccc | 1140 |
| ttcaatctgt cgcctgatgg tccctgtcat tcactcgggt gcgtgtgttt gtatgtctgt | 1200 |
| gtatgtatag gggaaagaag ggatccctaa ctgttccctt atctgttttc tacctcctcc | 1260 |
| tttgtttaat aaaggctgaa gcttttgta ctcatgaaaa aaaaaaaaaa aaaa | 1314 |

<210> SEQ ID NO 5
<211> LENGTH: 1431
<212> TYPE: DNA
<213> ORGANISM: Homo sapiens

<400> SEQUENCE: 5

| | |
|---|---|
| ccgtgaagtg ggcggagcga gcgatttgaa cgcgagcggc gcggacttct gccaagcacc | 60 |
| ggctcatgtg aggctcgcgg cacagcgttc tctgggctcc ccagaagcca gcctttcgct | 120 |
| cccggacccg gcagcccgag caggagccgt gggaccgggc gccagcaccc tctgcggcgt | 180 |
| gtcatgggcc cgcgccgccg gagccgaaag cccgaggccc cgaggaggcg cagcccgagc | 240 |
| ccgaccccga cccccggccc ctccggcgg ggccctcct taggcgcttc ctcccatcaa | 300 |
| cacagtcggc ggagacaagg ttggctaaag gagatccgaa agcttcagaa gagcacacac | 360 |
| ctcttgataa ggaagctgcc cttcagccgc ctggcaagag aaatatgtgt taaattcact | 420 |
| cgtggtgtgg acttcaattg gcaagcccag gccctattgg ccctacaaga ggcagcagaa | 480 |
| gcatttctag ttcatctctt tgaggacgcc tatctcctca ccttacatgc aggccgagtt | 540 |
| actctcttcc caaaggatgt gcaactggcc cggaggatcc ggggccttga ggagggactc | 600 |
| ggctgagctc ctgcacccag tgtttctgtc agtctttcct gctcagccag gggggatgat | 660 |
| accgggact ctccagagcc atgactagat ccaatggatt ctgcgatgct gtctggactt | 720 |
| tgctgtctct gaacagtatg tgtgtgttgc tttaaatatt ttcttttttt ttgagaagga | 780 |
| gaagactgca tgactttcct ctgtaacaga ggtaatatat gagacaatca acaccgttcc | 840 |
| aaaggcctga aaataatttt cagataaaga gactccaagg ttgactttag tttgtgagtt | 900 |
| actcatgtga ctatttgagg attttgaaaa catcagattt gctgtggtat gggagaaaag | 960 |
| gctatgtact tattattta gctctttctg taatatttac attttttacc atatgtacat | 1020 |
| ttgtactttt attttacaca taagggaaaa aataagacca ctttgagcag ttgcctggaa | 1080 |

-continued

| | |
|---|---|
| ggctgggcat tccatcata tagacctctg cccttcagag tagcctcacc attagtggca | 1140 |
| gcatcatgta actgagtgga ctgtgcttgt caacggatgt gtagcttttc agaaacttaa | 1200 |
| ttggggatga atagaaaacc tgtaagcttt gatgttctgg ttacttctag taaattcctg | 1260 |
| tcaaaatcaa ttcagaaatt ctaacttgga gaatttaaca ttttactctt gtaaatcata | 1320 |
| gaagatgtat cataacagtt cagaatttta aagtacattt tcgatgcttt tatgggtatt | 1380 |
| tttgtagttt ctttgtagag agataataaa aatcaaaata tttaatgaaa a | 1431 |

<210> SEQ ID NO 6
<211> LENGTH: 10316
<212> TYPE: DNA
<213> ORGANISM: Homo sapiens

<400> SEQUENCE: 6

| | |
|---|---|
| gagaccagaa gcgggcgaat tgggcaccgg tggcggctgc gggcagtttg aattagactc | 60 |
| tgggctccag cccgccgaag ccgcgccaga actgtactct ccgagaggtc gttttcccgt | 120 |
| ccccgagagc aagtttattt acaaatgttg gagtaataaa gaaggcagaa caaaatgagc | 180 |
| tgggctttgg aagaatggaa agaagggctg cctacaagag ctcttcagaa aattcaagag | 240 |
| cttgaaggac agcttgacaa actgaagaag gaaaagcagc aaaggcagtt tcagcttgac | 300 |
| agtctcgagg ctgcgctgca gaagcaaaaa cagaaggttg aaaatgaaaa aaccgagggt | 360 |
| acaaacctga aagggagaa tcaaagattg atggaaatat gtgaaagtct ggagaaaact | 420 |
| aagcagaaga tttctcatga acttcaagtc aaggagtcac aagtgaattt ccaggaagga | 480 |
| caactgaatt caggcaaaaa acaaatagaa aaactggaac aggaacttaa aaggtgtaaa | 540 |
| tctgagcttg aaagaagcca acaagctgcg cagtctgcag atgtctctct gaatccatgc | 600 |
| aatacaccac aaaaaatttt tacaactcca ctaacaccaa gtcaatatta tagtggttcc | 660 |
| aagtatgaag atctaaaaga aaatataat aagaggttg aagaacgaaa aagattagag | 720 |
| gcagaggtta aagccttgca ggctaaaaaa gcaagccaga ctcttccaca agccaccatg | 780 |
| aatcaccgcg acattgcccg gcatcaggct tcatcatctg tgttctcatg gcagcaagag | 840 |
| aagaccccaa gtcatctttc atctaattct caaagaactc caattaggag agatttctct | 900 |
| gcatcttact tttctgggga caagaggtg actccaagtc gatcaacttt gcaaataggg | 960 |
| aaaagagatg ctaatagcag tttctttgac aattctagca gtcctcatct tttggatcaa | 1020 |
| ttaaaagcgc agaatcaaga gctaagaaac aagattaatg agttggaact acgcctgcaa | 1080 |
| ggacatgaaa agaaatgaa aggccaagtg aataagtttc aagaactcca actccaactg | 1140 |
| gagaaagcaa agtggaatt aattgaaaaa gagaagtttt tgaacaaatg tagggatgaa | 1200 |
| ctagtgagaa caacagcaca atacgaccag gcgtcaacca gtatactgc attggaacaa | 1260 |
| aaactgaaaa aattgacgga agatttgagt tgtcagcgac aaaatgcaga aagtgccaga | 1320 |
| tgttctctgg aacagaaaat taggaaaaa gaaaaggagt tcaagagga gctctcccgt | 1380 |
| caacagcgtt ctttccaaac actggaccag gagtgcatcc agatgaaggc cagactcacc | 1440 |
| caggagttac agcaagccaa gaatatgcac aacgtcctgc aggctgaact ggataaactc | 1500 |
| acatcagtaa agcaacagct agaaaacaat ttggaagagt ttaagcaaaa gttgtgcaga | 1560 |
| gctgaacagg cgttccaggc gagtcagatc aaggagaatg agctgaggag aagcatggag | 1620 |
| gaaatgaaga ggaaaacaa cctccttaag agtcactctg agcaaaaggc cagagaagtc | 1680 |
| tgccacctgg aggcagaact caagaacatc aaacagtgtt taaatcagag ccagaatttt | 1740 |

```
gcagaagaaa tgaaagcgaa gaatacctct caggaaacca tgttaagaga tcttcaagaa    1800
aaaataaatc agcaagaaaa ctccttgact ttagaaaaac tgaagcttgc tgtggctgat    1860
ctggaaaagc agcgagattg ttctcaagac cttttgaaga aaagagaaca tcacattgaa    1920
caacttaatg ataagttaag caagacagag aaagagtcca aagccttgct gagtgcttta    1980
gagttaaaaa agaaagaata tgaagaattg aaagaagaga aaactctgtt ttcttgttgg    2040
aaaagtgaaa acgaaaaact tttaactcag atggaatcag aaaaggaaaa cttgcagagt    2100
aaaattaatc acttggaaac ttgtctgaag acacagcaaa taaaaagtca tgaatacaac    2160
gagagagtaa gaacgctgga gatggacaga gaaaacctaa gtgtcgagat cagaaacctt    2220
cacaacgtgt tagacagtaa gtcagtggag gtagagaccc agaaactagc ttatatggag    2280
ctacagcaga aagctgagtt ctcagatcag aaacatcaga aggaaataga aaatatgtgt    2340
ttgaagactt ctcagcttac tgggcaagtt gaagatctag aacacaagct tcagttactg    2400
tcaaatgaaa aatgacaca agaccggtgt taccaagact tgcatgccga atatgagagc    2460
ctcagggatc tgctaaaatc caaagatgct tctctggtga caaatgaaga tcatcagaga    2520
agtcttttgg cttttgatca gcagcctgcc atgcatcatt cctttgcaaa tataattgga    2580
gaacaaggaa gcatgccttc agagaggagt gaatgtcgtt tagaagcaga ccaaagtccg    2640
aaaaattctg ccatcctaca aaatagagtt gattcacttg aattttcatt agagtctcaa    2700
aaacagatga actcagacct gcaaaagcag tgtgaagagt tggtgcaaat caaggagaa    2760 atagaagaaa atctcatgaa agcagaacag atgcatcaaa gttttgtggc tgaaacaagt    2820
cagcgcatta gtaagttaca ggaagacact tctgctcacc agaatgttgt tgctgaaacc    2880
ttaagtgccc ttgagaacaa ggaaaaagag ctgcaacttt taaatgataa ggtagaaact    2940
gagcaggcag agattcaaga attaaaaaag agcaaccatc tacttgaaga ctctctaaag    3000
gagctacaac ttttatccga aaccctaagc ttggagaaga agaaatgag ttccatcatt    3060 tctctaaata aagggaaat tgaagagctg acccaagaga atgggactct taaggaaatt    3120
aatgcatcct taaatcaaga gaagatgaac ttaatccaga aagtgagag ttttgcaaac    3180 tatatagatg aaagggagaa aagcatttca gagttatctg atcagtacaa gcaagaaaaa    3240
cttattttac tacaaagatg tgaagaaacc ggaaatgcat atgaggatct tagtcaaaaa    3300
tacaaagcag cacaggaaaa gaattctaaa ttagaatgct tgctaaatga atgcactagt    3360
ctttgtgaaa ataggaaaaa tgagttggaa cagctaaagg aagcatttgc aaaggaacac    3420
caagaattct taacaaaatt agcatttgct gaagaaagaa atcagaatct gatgctagag    3480
ttggagacag tgcagcaagc tctgagatct gagatgacag ataaccaaaa caattctaag    3540
agcgaggctg gtggtttaaa gcaagaaatc atgactttaa aggaagaaca aaacaaaatg    3600
caaaaggaag ttaatgactt attacaagag aatgaacagc tgatgaaggt aatgaagact    3660
aaacatgaat gtcaaaatct agaatcagaa ccaattagga actctgtgaa agaaagagag    3720
agtgagagaa atcaatgtaa ttttaaacct cagatggatc ttgaagttaa agaaatttct    3780
ctagatagtt ataatgcgca gttggtgcaa ttagaagcta tgctaagaaa taaggaatta    3840
aaacttcagg aaagtgagaa ggagaaggag tgcctgcagc atgaattaca gacaattaga    3900
ggagatcttg aaaccagcaa tttgcaagac atgcagtcac aagaaattag tggccttaaa    3960
gactgtgaaa tagatgcgga agaaaagtat atttcagggc ctcatgagtt gtcaacaagt    4020
caaaacgaca atgcacacct tcagtgctct ctgcaaacaa caatgaacaa gctgaatgag    4080
ctagagaaaa tatgtgaaat actgcaggct gaaaagtatg aactcgtaac tgagctgaat    4140
```

```
gattcaaggt cagaatgtat cacagcaact aggaaaatgg cagaagaggt agggaaacta    4200
ctaaatgaag ttaaaatatt aaatgatgac agtggtcttc tccatggtga gttagtggaa    4260
gacataccag gaggtgaatt tggtgaacaa ccaaatgaac agcaccctgt gtctttggct    4320
ccattggacg agagtaattc ctacgagcac ttgacattgt cagacaaaga agttcaaatg    4380
cactttgccg aattgcaaga gaaattctta tctttacaaa gtgaacacaa aattttacat    4440
gatcagcact gtcagatgag ctctaaaatg tcagagctgc agacctatgt tgactcatta    4500
aaggccgaaa atttggtctt gtcaacgaat ctgagaaact tcaaggtga cttggtgaag     4560 gagatgcagc tgggcttgga ggaggggctc gttccatccc tgtcatcctc ttgtgtgcct    4620
gacagctcta gtcttagcag tttgggagac tcctcctttt acagagctct tttagaacag    4680
acaggagata tgtctctttt gagtaattta aaggggctg tttcagcaaa ccagtgcagt      4740
gtagatgaag tattttgcag cagtctgcag gaggagaatc tgaccaggaa agaaacccct    4800
tcggccccag cgaagggtgt tgaagagctt gagtccctct gtgaggtgta ccggcagtcc    4860
ctcgagaagc tagaagagaa aatggaaagt caagggatta tgaaaaataa ggaaattcaa    4920
gagctcgagc agttattaag ttctgaaagg caagagcttg actgccttag gaagcagtat    4980
ttgtcagaaa atgaacagtg gcaacagaag ctgacaagcg tgactctgga gatggagtcc    5040
aagttggcgg cagaaaagaa acagacggaa caactgtcac ttgagctgga agtagcacga    5100
ctccagctac aaggtctgga cttaagttct cggtctttgc ttggcatcga cacagaagat    5160
gctattcaag gccgaaatga gagctgtgac atatcaaaag aacatacttc agaaactaca    5220
gaaagaacac caaagcatga tgttcatcag atttgtgata agatgctca gcaggacctc     5280 aatctagaca ttgagaaaat aactgagact ggtgcagtga acccacagg agagtgctct     5340 ggggaacagt ccccagatac caattatgag cctccagggg aagataaaac ccagggctct    5400
tcagaatgca tttctgaatt gtcattttct ggtcctaatg ctttggtacc tatggatttc    5460
ctggggaatc aggaagatat ccataatctt caactgcggg taaaagagac atcaaatgag    5520
aatttgagat tacttcatgt gatagaggac cgtgacagaa aagttgaaag tttgctaaat    5580
gaaatgaaag aattagactc aaaactccat ttacaggagg tacaactaat gaccaaaatt    5640
gaagcatgca tagaattgga aaaaatagtt ggggaactta agaaagaaaa ctcagattta    5700
agtgaaaaat tggaatattt ttcttgtgat caccaggagt tactccagag agtagaaact    5760
tctgaaggcc tcaattctga tttagaaatg catgcagata atcatcacg tgaagatatt      5820 ggagataatg tggccaaggt gaatgacagc tggaaggaga gatttcttga tgtggaaaat    5880
gagctgagta ggatcagatc ggagaaagct agcattgagc atgaagccct ctacctggag    5940
gctgacttag aggtagttca aacagagaag ctatgtttag aaaagacaa tgaaaataag      6000 cagaaggtta ttgtctgcct tgaagaagaa ctctcagtgg tcacaagtga gagaaaccag    6060
cttcgtggag aattagatac tatgtcaaaa aaaaccacgg cactggatca gttgtctgaa    6120
aaaatgaagg agaaaacaca agagcttgag tctcatcaaa gtgagtgtct ccattgcatt    6180
caggtggcag aggcagaggt gaaggaaaag acggaactcc ttcagacttt gtcctctgat    6240
gtgagtgagc tgttaaaaga caaaactcat ctccaggaaa agctgcagag tttggaaaag    6300
gactcacagg cactgtcttt gacaaaatgt gagctggaaa accaaattgc acaactgaat    6360
aaagagaaag aattgcttgt caaggaatct gaaagcctgc aggccagact gagtgaatca    6420
gattatgaaa agctgaatgt ctccaaggcc ttggaggccg cactggtgga gaaaggtgag    6480
```

-continued

```
ttcgcattga ggctgagctc aacacaggag gaagtgcatc agctgagaag aggcatcgag    6540
aaactgagag ttcgcattga ggccgatgaa aagaagcagc tgcacatcgc agagaaactg    6600
aaagaacgcg agcgggagaa tgattcactt aaggataaag ttgagaacct tgaaagggaa    6660
ttgcagatgt cagaagaaaa ccaggagcta gtgattcttg atgccgagaa ttccaaagca    6720
gaagtagaga ctctaaaaac acaaatagaa gagatggcca gaagcctgaa agttttgaa     6780 ttagaccttg tcacgttaag gtctgaaaaa gaaaatctga caaacaaat acaagaaaaa     6840 caaggtcagt tgtcagaact agacaagtta ctctcttcat ttaaaagtct gttagaagaa    6900
aaggagcaag cagagataca gatcaaagaa gaatctaaaa ctgcagtgga gatgcttcag    6960
aatcagttaa aggagctaaa tgaggcagta gcagccttgt gtggtgacca agaaattatg    7020
aaggccacag aacagagtct agacccacca atagaggaag agcatcagct gagaaatagc    7080
attgaaaagc tgagagcccg cctagaagct gatgaaaaga agcagctctg tgtcttacaa    7140
caactgaagg aaagtgagca tcatgcagat ttacttaagg gtagagtgga gaaccttgaa    7200
agagagctag atatagccag gacaaaccaa gagcatgcag ctcttgaggc agagaattcc    7260
aaaggagagg tagagaccct aaaagcaaaa atagaaggga tgacccaaag tctgagaggt    7320
ctggaattag atgttgttac tataaggtca gaaaaagaaa atctgacaaa tgaattacaa    7380
aaagagcaag agcgaatatc tgaattagaa ataataaatt catcatttga aaatattttg    7440
caagaaaaag agcaagagaa agtacagatg aaagaaaaat caagcactgc catggagatg    7500
cttcaaacac aattaaaaga gctcaatgag agagtggcag ccctgcataa tgaccaagaa    7560
gcctgtaagg ccaaagagca gaatcttagt agtcaagtag agtgtcttga acttgagaag    7620
gctcagttgc tacaaggcct tgatgaggcc aaaaataatt atattgtttt gcaatcttca    7680
gtgaatggcc tcattcaaga agtagaagat ggcaagcaga aactggagaa gaaggatgaa    7740
gaaatcagta gactgaaaaa tcaaattcaa gaccaagagc agcttgtctc taaactgtcc    7800
caggtggaag gagagcacca actttggaag gagcaaaact tagaactgag aaatctgaca    7860
gtggaattgg agcagaagat ccaagtgcta caatccaaaa atgcctcttt gcaggacaca    7920
ttagaagtgc tgcagagttc ttacaagaat ctagagaatg agcttgaatt gacaaaaatg    7980
gacaaaatgt cctttgttga aaaagtaaac aaaatgactg caaaggaaac tgagctgcag    8040
agggaaatgc atgagatggc acagaaaaca gcagagctgc aagaagaact cagtggagag    8100
aaaaataggc tagctggaga gttgcagtta ctgttggaag aaataaagag cagcaaagat    8160
caattgaagg agctcacact agaaaatagt gaattgaaga gagcctaga ttgcatgcac     8220 aaagaccagg tggaaaagga agggaaagtg agagaggaaa tagctgaata tcagctacgg    8280
cttcatgaag ctgaaaagaa acaccaggct ttgcttttgg acacaaacaa acagtatgaa    8340
gtagaaatcc agacataccg agagaaattg acttctaaag aagaatgtct cagttcacag    8400
aagctggaga tagacctttt aaagtctagt aagaagagc tcaataattc attgaaagct     8460
actactcaga ttttggaaga attgaagaaa accaagatgg acaatctaaa atatgtaaat    8520
cagttgaaga aggaaaatga acgtgcccag gggaaaatga agttgttgat caaatcctgt    8580
aaacagctgg aagaggaaaa ggagatactg cagaaagaac tctctcaact tcaagctgca    8640
caggagaagc agaaaacagg tactgttatg gataccaagg tcgatgaatt aacaactgag    8700
atcaaagaac tgaaagaaac tcttgaagaa aaaccaagg aggcagatga atacttggat      8760
aagtactgtt ccttgcttat aagccatgaa aagttagaga aagctaaaga gatgttagag    8820
acacaagtgg cccatctgtg ttcacagcaa tctaaacaag attcccgagg gtctcctttg    8880
```

```
ctaggtccag ttgttccagg accatctcca atcccttctg ttactgaaaa gaggttatca   8940
tctggccaaa ataaagcttc aggcaagagg caaagatcca gtggaatatg ggagaatggt   9000
agaggaccaa cacctgctac cccagagagc ttttctaaaa aaagcaagaa agcagtcatg   9060
agtggtattc accctgcaga agacacggaa ggtactgagt tgagccaga gggacttcca    9120 gaagttgtaa agaaagggtt tgctgacatc ccgacaggaa agactagccc atatatcctg   9180
cgaagaacaa ccatggcaac tcggaccagc ccccgcctgg ctgcacagaa gttagcgcta   9240
tccccactga gtctcggcaa agaaaatctt gcagagtcct ccaaaccaac agctggtggc   9300
agcagatcac aaaaggtcaa agttgctcag cggagcccag tagattcagg caccatcctc   9360
cgagaaccca ccacgaaatc cgtcccagtc aataatcttc ctgagagaag tccgactgac   9420
agccccagag agggcctgag ggtcaagcga ggccgacttg tccccagccc caaagctgga   9480
ctggagtcca acggcagtga gaactgtaag gtccagtgaa ggcactttgt gtgtcagtac   9540
ccctgggagg tgccagtcat tgaatagata aggctgtgcc tacaggactt ctctttagtc   9600
agggcatgct ttattagtga ggagaaaaca attccttaga agtcttaaat atattgtact   9660
ctttagatct cccatgtgta ggtattgaaa aagtttggaa gcactgatca cctgttagca   9720 tgccattcc tctactgcaa tgtaaatagt ataaagctat gtatataaag cttttttggta   9780 atatgttaca attaaaatga caagcactat atcacaatct ctgtttgtat gtgggtttta   9840
cactaaaaaa atgcaaaaca catttttattc ttctaattaa cagctcctag gaaaatgtag   9900
acttttgctt tatgatattc tatctgtagt atgaggcatg gaatagtttt gtatcgggaa   9960
tttctcagag ctgagtaaaa tgaaggaaaa gcatgttatg tgtttttaag gaaaatgtgc  10020
acacatatac atgtaggagt gtttatcttt ctcttacaat ctgttttaga catctttgct  10080
tatgaaacct gtacatatgt gtgtgtgggt atgtgtttat ttccagtgag ggctgcaggc  10140
ttcctagagg tgtgctatac catgcgtctg tcgttgtgct ttttttctgtt tttagaccaa  10200 tttttttacag ttcttttggta agcattgtcg tatctggtga tggattaaca tatagccttt  10260
gttttctaat aaaatagtcg ccttcgtttt ctgtaaaaaa aaaaaaaaaa aaaaaa      10316
```

<210> SEQ ID NO 7
<211> LENGTH: 834
<212> TYPE: DNA
<213> ORGANISM: Homo sapiens

<400> SEQUENCE: 7

```
ggcggcgtgt tgaaagcga ggccaaagtg ggtgggagcg cgtgctgttg ggagttgctt     60
ggaggttggc ggcgcgggc tgaaggctag caaaccgagc gatcatgtcg cacaaacaaa    120
tttactattc ggacaaatac gacgacgagg agtttgagta tcgacatgtc atgctgccca    180
aggacatagc caagctggtc cctaaaaccc atctgatgtc tgaatctgaa tggaggaatc    240
ttggcgttca gcagagtcag ggatgggtcc attatatgat ccatgaacca gaacctcaca    300
tcttgctgtt ccggcgccca ctacccaaga aaccaaagaa atgaagctgg caagctactt    360
ttcagcctca agctttacac agctgtcctt acttcctaac atctttctga taacattatt    420
atgttgcctt cttgtttctc actttgatat ttaaagatg ttcaatacac tgtttgaatg     480
tgctggtaac tgctttgctt cttgagtaga gccaccacca ccatagccca gccagatgag    540
tgctctgtgg acccacagcc taagctgagt gtgaccccag aagccacgat gtgctctgta    600
tccagaacac acttggcaga tggaggaagc atctgagttt gagaccatgg ctgttacagg    660
```

```
gatcatgtaa acttgctgtt tttgttttt cctgccgggt gttgtatgtg tggtgacttg      720
cggatttatg tttcagtgta ctggaaactt tccattttat tcaagaaatc tgttcatgtt      780
aaaagccttg attaaagagg aagtttttat aatctaaaaa aaaaaaaaaa aaaa            834

<210> SEQ ID NO 8
<211> LENGTH: 3736
<212> TYPE: DNA
<213> ORGANISM: Homo sapiens

<400> SEQUENCE: 8
agttggggga agtgcactga gcgagtggcg gccgggggac agtacctgct tgccttattg       60
ggcaaataca gccttccaag gtggagtcta acgccgtggt gtgaactggc cacccgaaca      120
gggagtaaat agtgctttgt atctttaagg aagccctttt ttaaatttaa aaaaaaagtc      180
ttaattataa gactctttaa atgcccaact gcatacttgg agctttggga ctgaatttgg      240
aactttcctg tcaagcgacc tcccacgact ttactgctga gcctgtgcac gtgtgtgtaa      300
ggggagaaat ccaggcatct agatgcagac ttgtacccag ttacttgggg tcgcgtgcgc      360
tcagctggga cctgggctcg tgcgcttagt ccggagccct gatctgcgaa caggatatta      420
aaacttttag tacaattgat tggactactt gaaccatcgg gatttgggga ggaactccag      480 attttttcatt tttaaactct aaatgtatga ggaatttaca gaatggagaa cgaaaaggaa      540
aatctctttt gtgagccaca taaaggggga ctaatgaaaa cacctctgaa gaatccacc       600 acagcaaata tcgtgttggc agagatccag cctgactttg gccctttaac cacacctacc      660
aagcccaagg aaggctctca gggagagccg tggacaccga cagccaacct gaaaatgctc      720
atcagtgctg tgagccctga gatccgcaac agagatcaga aaggggttt gtttgacaac       780 agaagtggat tacctgaggc caaagactgt atacacgaac acttatctgg agatgaattt      840
gagaaatccc aaccaagtcg aaaagagaaa agtttaggat tattgtgtca taagttctta      900
gcacgatatc ctaattatcc caaccctgct gtgaataatg acatctgcct tgacgaagtg      960
gcagaggaac ttaatgttga acgtcgacgc atttacgata tcgtgaacgt cctagagagt     1020
ttacatatgg tgagccgcct cgccaaaaac aggtacactt ggcacgggcg acacaatctc     1080
aacaaaaccc ttggcacctt gaagagcatc ggggaggaga ataagtacgc cgagcagatt     1140
atgatgatca aaagaaaga atatgagcaa gagtttgact ttattaagag ttacagtata     1200
gaggatcata tcatcaaatc aaacactggc ccaaatggac acccagacat gtgttttgtg     1260
gaactccctg gagtggaatt tcgggcagct tctgtaaaca gccgcaaaga caagtctta      1320 agggtaatga gccagaaatt tgtgatgctg tttttggtgt caacgcctca gatagtaagc     1380
ctagaagttg ctgccaagat tttaattggg gaggaccatg tggaagattt ggataaaagc     1440
aagtttaaaa caaaaattag gaggttgtat gatatagcta atgttctgag tagcctggat     1500
cttatcaaga aagttcatgt tacagaggaa agaggccgaa aaccagcttt caaatggacc     1560
ggcccagaaa tcagtccaaa taccagtggc tccagcccag tcattcattt tactccctct     1620
gatttggagg tgagacggtc ttcaaaagag aactgtgcca aaaacctctt ttccacacgt     1680
gggaaaccaa actttactcg acacccatct cttatcaaat tggtaaagag tatagaaagt     1740
gatcggagaa agataaattc tgcgcccagt agccctatca agaccaacaa agctgagagt     1800
tctcagaatt ctgcacccct tcccaagtaaa atggctcagc tcgcagctat ttgtaaaatg     1860
cagttagaag agcaatcaag tgaatccaga cagaaagtga agtacagct ggcaagatct     1920 ggaccctgca aaccagtagc ccctctggac cccccagtga atgctgagat ggagctgaca     1980
```

```
gcaccgtccc tcatccagcc cctgggaatg gttccctga tccccagccc cttgtcatca    2040
gcagtgcccc tgatcctacc tcaggcccct tcaggcccat cctatgccat ctacctgcag    2100
cccactcaag cccaccaaag tgtgacgcca ccccaaggcc tgagcccaac ggtgtgcacc    2160
acccactctt ctaaagctac tggctcaaaa gactccacag atgccaccac tgagaaggca    2220
gccaatgata cctcaaaggc cagtgcctct accaggcctg gaagcttgct gccagcacca    2280
gagaggcaag gggcaaagag ccgaaccagg agccagctg gagaaagagg ctcaaagagg    2340
gcaagcatgc tcgaggacag tggttccaaa agaaattta agaggacct aaaaggactt     2400 gaaaatgtct ccgcaacctt gttcccatca ggatacctaa tccctctcac gcagtgctca    2460
tccctggggg cagagtccat tttgtctggt aaagaaaact caagtgctct tcccccaaac    2520
cacaggattt acagctcccc aattgcaggt gttattccag tgacatcatc tgaactcact    2580
gctgttaatt ttccctcttt tcatgtaaca ccgttgaagc taatggtctc accaacttcc    2640
gtggcagccg tacctgtcgg aacagcccg gctctcgctt caagccaccc tgttcccatc     2700
cagaacccaa gctcagccat tgtaaacttc accctgcagc acctgggact catctcaccc    2760
aatgtgcagt tgtctgccag ccctgggtct ggaatcgttc ctgtgtctcc aagaatagag    2820
tctgttaatg tcgcaccaga aaatgcaggc actcagcaag aagggccac caactatgac     2880 tcaccagtcc caggccagag ccagccaaat ggacaatcag ttgctgtgac agggcacaa    2940 cagcctgttc ctgtgacacc caaagggtca caattagtgg ccgaaagttt cttccgtacc    3000
ccaggtggac ccaccaagcc aaccagctca tcctgcatgg attttgaggg tgctaataaa    3060
acctccttag gaactctctt tgtcccacag cgaaaactgg aagtctcaac agaggatgtc    3120
cattaatcaa cagatgttgg cttagtttaa ttttctaaag agttgtttaa tagagaaaat    3180
gtacacagac tgatttggag aacacattct ctgaaaatac tgtaaatacg ttggggattt    3240
gttcaatgtg aaatcagata gttgttttca tacatatata tatatacaca cacacacaca    3300
cacacacaca cacatatatt tgtataaagc taagtttagc tttcaatcct acaaaataaa    3360
agtaaaatgt tgaactctaa gatatattaa cttctagggg gaaaaatcca ttattttagc    3420
tatgcctata ctattatgca aagtaactgt attaaagttt acttccctct aagcaaatat    3480
gcttgacatg cctaacacag cattccctta acattttgc acaaagaaaa tgctgtgtga    3540
tgtataatgt tgtatttta aatagggta tagctatatt ttttgtaatt tctttaatct     3600
gttgttgcag tgtatctttt tgtaaagttt gcaacaatcc tcaatcaagt ctatggaaaa    3660
attatttata aaatgtattt ttaatcataa gttgttcaaa ttaaaacttt tctaaaatat    3720
aaaaaaaaaa aaaaaa                                                    3736
```

<210> SEQ ID NO 9
<211> LENGTH: 4224
<212> TYPE: DNA
<213> ORGANISM: Homo sapiens

<400> SEQUENCE: 9

```
gcgaaattca agctccaaac tctaagctcc aagctccaag ctccaagctc caagctccaa     60
actcccgccg gggtaactgg aacccaatcc gagggtcatg gaggcatccc gaaggtttcc    120
ggaagccgag gccttgagcc cagagcaggc tgctcattac ctaagatatg tgaaagaggc    180
caaagaagca actaagaatg gagacctgga agaagcattt aaacttttca atttggcaaa    240
ggacattttt cccaatgaaa aagtgctgag cagaatccaa aaaatacagg aagccttgga    300
```

```
ggagttggca gaacagggag atgatgaatt tacagatgtg tgcaactctg gcttgctact    360
ttatcgagaa ctgcacaacc aactctttga gcaccagaag gaaggcatag cttttcctcta  420
tagcctgtat agggatggaa gaaaaggtgg tatattggct gatgatatgg gattagggaa   480
gactgttcaa atcattgctt tcctttccgg tatgtttgat gcatcacttg tgaatcatgt   540
gctgctgatc atgccaacca atcttattaa cacatgggta aaagaattca tcaagtggac   600
tccaggaatg agagtcaaaa cctttcatgg tcctagcaag gatgaacgga ccagaaacct   660
caatcggatt cagcaaagga atggtgttat tatcactaca taccaaatgt taatcaataa   720
ctggcagcaa cttttcaagct ttaggggcca agagtttgtg tgggactatg tcatcctcga  780
tgaagcacat aaaataaaaa cctcatctac taagtcagca atatgtgctc gtgctattcc   840
tgcaagtaat cgcctcctcc tcacaggaac cccaatccag ataatttac aagaactatg    900
gtccctattt gattttgctt gtcaagggtc cctgctggga acattaaaaa cttttaagat   960
ggagtatgaa atcctatta ctagagcaag agagaaggat gctacccag gagaaaaagc    1020
cttgggattt aaaatatctg aaaacttaat ggcaatcata aaaccctatt ttctcaggag   1080
gactaaagaa gacgtacaga agaaaaagtc aagcaaccca gaggccagac ttaatgaaaa   1140
gaatccagat gttgatgcca tttgtgaaat gccttccctt tccaggaaaa atgatttaat   1200
tatttggata cgacttgtgc ctttacaaga agaaatatac aggaaatttg tgtctttaga   1260
tcatatcaag gagttgctaa tggagacgcg ctcacctttg gctgagctag gtgtcttaaa   1320
gaagctgtgt gatcatccta ggctgctgtc tgcacgggct tgttgtttgc taaatcttgg   1380
gacattctct gctcaagatg gaaatgaggg ggaagattcc ccagatgtgg accatattga   1440
tcaagtaact gatgacacat tgatggaaga atctggaaaa atgatattcc taatggacct   1500
acttaagagg ctgcgagatg agggacatca aactctggtg ttttctcaat cgaggcaaat   1560
tctaaacatc attgaacgcc tcttaaagaa taggcacttt aagacattgc gaatcgatgg   1620
gacagttact catcttttgg aacgagaaaa aagaattaac ttattccagc aaaataaaga   1680
ttactctgtt tttctgctta ccactcaagt aggtggtgtc ggtttaacat taactgcagc   1740
aactagagtg tcatttttg accctagctg gaatcctgca actgatgctc aagctgtgga   1800
tagagtttac cgaattggac aaaaagagaa tgttgtggtt tataggctaa tcacttgtgg   1860
gactgtagag gaaaaaatat acagaagaca ggttttcaag gactcattaa taagacaaac   1920
tactggtgaa aaaaagaacc cttttccgata ttttagtaaa caagaattaa gagagctctt   1980
tacaatcgag gatcttcaga actctgtaac ccagctgcag cttcagtctt tgcatgctgc   2040
tcagaggaaa tctgatataa aactagatga acatattgcc tacctgcagt ctttggggat   2100
agctggaatc tcagaccatg atttgatgta cacatgtgat ctgtctgtta agaagagct   2160
tgatgtggta gaagaatctc actatattca acaagggtt cagaaagctc aattcctcgt   2220
tgaattcgag tctcaaaata agagttcct gatggaacaa caagaactag aaatgaggg   2280
ggcctggcta agagaacctg tatttccttc ttcaacaaag aagaaatgcc ctaaattgaa   2340
taaaccacag cctcagcctt cacctcttct aagtactcat catactcagg aagaagatat   2400
cagttccaaa atggcaagtg tagtcattga tgatctgccc aaagagggtg agaaacaaga   2460
tctctccagt ataaaggtga atgttaccac cttgcaagat ggtaaaggta caggtagtgc   2520
tgactctata gctactttac caaggggtt tggaagtgta gaagaacttt gtactaactc   2580
ttcattggga atggaaaaaa gctttgcaac taaaaatgaa gctgtacaaa aagagacatt   2640
acaagagggg cctaagcaag aggcactgca agaggatcct ctggaaagtt taattatgt    2700
```

-continued

```
acttagcaaa tcaaccaaag ctgatattgg gccaaattta gatcaactaa aggatgatga    2760
gattttacgt cattgcaatc cttggcccat tatttccata acaaatgaaa gtcaaaatgc    2820
agaatcaaat gtatccatta ttgaaatagc tgatgacctt tcagcatccc atagtgcact    2880
gcaggatgct caagcaagtg aggccaagtt ggaagaggaa ccttcagcat cttcaccaca    2940
gtatgcatgt gatttcaatc ttttcttgga agactcagca gacaacagac aaaattttc    3000
cagtcagtct ttagagcatg ttgagaaaga aaatagcttg tgtggctctg cacctaattc    3060
cagagcaggg tttgtgcata gcaaaacatg tctcagttgg gagttttctg agaaagacga    3120
tgaaccagaa gaagtagtag ttaaagcaaa aatcagaagt aaagctagaa ggattgtttc    3180
agatggcgaa gatgaagatg attcttttaa agatacctca agcataaatc cattcaacac    3240
atctctcttt caattctcat ctgtgaaaca atttgatgct tcaactccca aaaatgacat    3300
cagtccacca ggaaggttct tttcatctca atacccagt agtgtaaata agtctatgaa    3360
ctctagaaga tctctggctt ctaggaggtc tcttattaat atggttttag accacgtgga    3420
ggacatggag gaaagacttg acgacagcag tgaagcaaag ggtcctgaag attatccaga    3480
agaaggggtg gaggaaagca gtggcgaagc ctccaagtat acagaagagg atccttccgg    3540
agaaacactg tcttcagaaa acaagtccag ctggttaatg acgtctaagc ctagtgctct    3600
agctcaagag acctctcttg gtgcccctga gcctttgtct ggtgaacagt tggttggttc    3660
tccccaggat aaggcggcag aggctacaaa tgactatgag actcttgtaa agcgtggaaa    3720
agaactaaaa gagtgtggaa aaatccagga ggccctaaac tgcttagtta aagcgcttga    3780
cataaaagt gcagatcctg aagttatgct cttgacttta agtttgtata agcaacttaa    3840
taacaattga gaatgtaacc tgtttattgt attttaaagt gaaactgaat atgagggaat    3900
ttttgttccc ataattggat tctttgggaa catgaagcat tcaggcttaa ggcaagaaag    3960
atctcaaaaa gcaacttctg ccctgcaacg ccccccactc catagtctgg tattctgagc    4020
actagcttaa tatttcttca cttgaatatt cttatatttt aggcatattc tataaattta    4080
actgtgttgt ttcttggaaa gttttgtaaa attattctgg tcattcttaa ttttactctg    4140
aaagtgatca tctttgtata taacagttca gataagaaaa ttaaagttac ttttctcaag    4200
tgttttcaaa aaaaaaaaaa aaaa                                           4224
```

<210> SEQ ID NO 10
<211> LENGTH: 2445
<212> TYPE: DNA
<213> ORGANISM: Homo sapiens

<400> SEQUENCE: 10

```
aaagcagcca atgggagagc cgaggcgggg aggtgcggcc aatggcgcgg gcctgtttga     60
ttcaaaggtt gcctataaag cgggactgca cgccggtttt tgtccgaggg ctgtcgagtc    120
cgagcgccgc catggctctg ctgtccgagg gcctggacga ggtgcccgcc gcctgcctgt    180
cgccgtgcgg gccgcccaac ccgaccgagc tgttcagcga gtcacggcgc ctggctctgg    240
aggagctggt ggcgggcggc cccgaagcct tcgcggcctt cctgcgacgc gagcgcctgg    300
ctcgtttcct gaaccccgat gaggtgcacg ccattctgcg cgcggcggag aggccgggag    360
aggagggcgc ggcggcggcg gcggcggccg aggactcgtt cggctcctcg cacgactgct    420
cttcgggcac ctactccccc gagcagtcgg acctggagcc accgctgttg gagcttggct    480
ggcccgcctt ctaccagggc gcctaccgcg gcgccacgcg tgtcgagacg cacttccagc    540
```

```
cccgcggcgc tggcgaaggt ggcccctacg gctgcaagga cgctctgcgc cagcagctcc    600
gctcggcgcg agaggtgatt gcagtggtca tggacgtgtt cacagacatc gacatcttca    660
gagacctgca agaaatatgc aggaaacagg gagttgctgt gtatatcctt ctggaccagg    720
ctctcctctc tcaatttctg gatatgtgca tggatctgaa agttcatcct gaacaggaaa    780
agttaatgac agttcggact atcacaggaa atatctacta tgcaaggtca ggaactaaga    840
ttattgggaa ggttcacgaa aagttcacgt tgattgatgg catccgcgtg gcaacaggct    900
cctacagttt tacatggacg gatggcaaat taaacagcag taacttggta attctgtctg    960
gccaagtggt tgaacacttt gatctggagt tccgaatcct gtatgcccag tccaagccca   1020
tcagccccaa actcctgtct cacttccaga gcagcaacaa gtttgatcac ctcaccaacc   1080
gaaaaccaca gtccaaggag ctcaccctgg gcaacctgct gcggatgcgg ctggctaggc   1140
tgtcaagtac tcccaggaag gcggacctgg acccagagat gcccgcagag ggcaaggcag   1200
agcgcaagcc ccatgactgt gagtcctcta ctgttagtga ggaagactac ttcagcagcc   1260
acagggacga gctccagagc agaaaggcca ttgacgctgc cactcaaaca gagccaggag   1320
aggagatgcc agggctgagt gtgagtgagg tgggaacaca aaccagcatc accacagcat   1380
gtgctggtac ccagactgca gtcatcacca ggatagcaag ctctcaaacc acgatttggt   1440
ccagatcgac cactactcag actgacatgg atgagaacat tctctttcct cgaggaactc   1500
aatctacaga agggtcacca gtctcaaaaa tgtctgtatc gagatcttcc agtttgaagt   1560
cttcctcctc tgtgtcttcc caaggctctg tggcaagctc cactggttct cccgcttcca   1620
tcagaaccac tgacttccac aatcctggct atcccaagta cctgggcacc cccacctgg    1680 aactgtactt gagtgactca cttagaaact tgaacaaaga gcggcaattc cacttcgctg   1740
gtatcaggtc ccggctcaac cacatgctgg ctatgctgtc aaggagaaca ctctttactg   1800
aaaaccacct tggccttcat tctggcaatt tcagcagagt taatttgctt gctgttagag   1860
atgtagcact ttatccttcc tatcagtaac tgctccgtgt tcagactcct ggtttcttcc   1920
aggcttacag tggacatcat cagcttcctg ctttaaaaaa tatcttatgt ccctaattgc   1980
ctttctttta cctgactttg tcacctttgt tgtctttgaa ttcttaggc tgcatattat    2040 tttacatgct ttgttttgtc atgtatatac caggtattgg ttttatggtt taaacactat   2100
ggatacaggg gtttgttttg cacaatttta atagtcatgc actacataat gatgttttgg   2160
tcaatgacag accacgtata tgttggcagt ctcataagat tataatactg tattttttact  2220 ataccttttc tgtgtttaga tacaaatacc attatgttac agttgcctac agtattcagt   2280
gcagtaacat gatgtacagg tttgtagcct gttttgcatt tttcttaggt tgtatgctct   2340
tctgttttaa aggtttgaat caccagcatt tttgtgatca aaatcctatt tagaaaaaat   2400
aaaactactt tctgtttatc tctttagaaa aaaaaaaaa aaaaa                    2445

<210> SEQ ID NO 11
<211> LENGTH: 2721
<212> TYPE: DNA
<213> ORGANISM: Homo sapiens

<400> SEQUENCE: 11
gcggcgacgt ccacgcattt tctgacgtag cgagcgacgg cggggagccg agcggaagtc     60
cagcactatt gccgctagag gagggagggg gtgagaagca taagtggcac cggaagtgga   120
attaatccgc ctacctctcc tgcgcctgcg aaacagaaaa gacaaggcgc ctgtcgggcg   180
gggtgtggct tcgggtggcg gagaacgctg cgattggccc tcggctgtgg cgacagcgac   240
```

```
gattggtccc tgcgtgcaga gcgcggtgag agtgggtggt ggccgttgga attcaaaagt    300
ggcgggtgtg gcgcggggct ggtagcggcc ggagccgtgc gagttctcta ccctgcttcg    360
cgagcgggcg agagaacgcg agtcccagga tccccggcac ccagttctct tccactgcat    420
tcccccggcg cgtgtgggac cgaggtggac atggatccgc agaggtcccc cctattggaa    480
gtaaagggga acatagaact gaagagacct ctgattaagg ccccttccca gctgcctctc    540
tcaggaagca gactcaagag gaggcctgac cagatgaag atgggcctgga gcctgagaag    600 aaacggacaa gaggcctggg tgcaacgacc aaaattacca catcccaccc aagagttcca    660
tccctcacta cagtgccaca gacacaaggc cagaccacga ctcaaaaagt tccaagaag    720 acaggacccc ggtgttccac agctattgcc acagggttga agaaccagaa gccagttcct    780
gctgttcctg tccagaagtc tggcacatca ggtgttcctc ccatggcagg agggaagaaa    840
cccagcaaac gtccagcctg ggacttaaag ggtcagttat gtgacctaaa tgcagaacta    900
aaacggtgcc gtgagaggac tcaaacgttg gaccaagaga accagcagct tcaggaccag    960
ctcagagatg cccagcagca ggtcaaggcc ctggggacag agcgcacaac actggagggg   1020
catttagcca aggtacaggc ccaggctgag cagggccaac aggagctgaa gaacttgcgt   1080
gcttgtgtcc tggagctgga agagcggctg agcacgcagg agggcttggt gcaagagctt   1140
cagaaaaaac aggtggaatt gcaggaagaa cggaggggac tgatgtccca actagaggag   1200
aaggagagga ggctgcagac atcagaagca gccctgtcaa gcagccaagc agaggtggca   1260
tctctgcggc aggagactgt ggcccaggca gccttactga ctgagcggga agaacgtctt   1320
catgggctag aaatggagcg ccggcgactg cacaaccagc tgcaggaact caagggcaac   1380
atccgtgtat tctgccgggt ccgccctgtc ctgccggggg agcccactcc accccctggc   1440
ctcctcctgt ttccctctgg ccctggtggg ccctctgatc ctccaacccg ccttagcctc   1500
tcccggtctg acgagcggcg tgggaccctg agtggggcac cagctccccc aactcgccat   1560
gatttttcct ttgaccgggt attcccacca ggaagtggac aggatgaagt gtttgaagag   1620
attgccatgc ttgtccagtc agccctggat ggctatccag tatgcatctt tgcctatggc   1680
cagacaggca gtggcaagac cttcacaatg gagggtgggc ctgggggaga cccccagttg   1740
gaggggctga tccctcgggc cctgcggcac ctcttctctg tggctcagga gctgagtggt   1800
cagggctgga cctacagctt tgtagcaagc tacgtagaga tctacaatga gactgtccgg   1860
gacctgctgg ccactggaac ccggaagggt caaggggggcg agtgtgagat tcgccgtgca   1920
gggccaggga gtgaggagct cactgtcacc aatgctcgat atgtccctgt ctcctgtgag   1980
aaagaagtgg acgccctgct tcatctggcc cgccagaatc gggctgtggc ccgcacagcc   2040
cagaatgaac ggtcatcacg cagccacagt gtattccagc tacagatttc tggggagcac   2100
tccagccgag gcctgcagtg tggggccccc ctcagtcttg tggacctggc cgggagtgag   2160
cgacttgacc ccggcttagc cctcggcccc gggagcggg aacgccttcg ggaaacacag   2220
gccattaaca gcagcctgtc cacgctgggg ctggttatca tggcccctgag caacaaggag   2280 tcccacgtgc cttaccggaa cagcaaactg acctacctgc tgcagaactc tctgggtggt   2340
agtgctaaga tgctcatgtt tgtgaacatt tctccactgg aagagaacgt ctccgagtcc   2400
ctcaactctc tacgctttgc ctccaaggtg aaccagtgtg ttattggtac tgctcaggcc   2460
aacaggaagt gaaagcggat ccagatctgt gtgtgtgtgt gtgtgtgtgt gtgtgtgtgt   2520
gtgtgtgtgt gtgtgtccct atgtctatgt atcgggtgag gggtgggagg gttgctggag   2580
```

```
ggtgctttat tgggtggagg gcaccatgtc ccagggctat caaataaaga atagtttggt      2640 tttttttta ataaaggtt ttattagcat ttgcccaaga aggcagatac tttcatatct        2700
gtaaaaaaaa aaaaaaaaa a                                                 2721

<210> SEQ ID NO 12
<211> LENGTH: 12507
<212> TYPE: DNA
<213> ORGANISM: Homo sapiens

<400> SEQUENCE: 12
taccgggcgg aggtgagcgc ggcgccggct cctcctgcgg cggactttgg gtgcgacttg        60
acgagcggtg gttcgacaag tggccttgcg ggccggatcg tcccagtgga agagttgtaa      120
atttgcttct ggccttcccc tacggattat acctggcctt ccctacgga ttatactcaa       180 cttactgttt agaaaatgtg gcccacgaga cgcctggtta ctatcaaaag gagcggggtc      240
gacggtcccc actttcccct gagcctcagc acctgcttgt ttggaagggg tattgaatgt      300
gacatccgta tccagcttcc tgttgtgtca aacaacatt gcaaaattga aatccatgag       360
caggaggcaa tattacataa tttcagttcc acaaatccaa cacaagtaaa tgggtctgtt      420
attgatgagc ctgtacggct aaaacatgga gatgtaataa ctattattga tcgttccttc     480
aggtatgaaa atgaaagtct tcagaatgga aggaagtcaa ctgaatttcc aagaaaaata      540
cgtgaacaga agccagcacg tcgtgtctca agatctagct tctcttctga ccctgatgag      600
aaagctcaag attccaaggc ctattcaaaa atcactgaag gaaaagtttc aggaaatcct      660
caggtacata tcaagaatgt caagaagac agtaccgcag atgactcaaa agacagtgtt       720
gctcagggaa caactaatgt tcattcctca gaacatgctg gacgtaatgg cagaaatgca     780
gctgatccca tttctgggga ttttaaagaa atttccagcg ttaaattagt gagccgttat      840
ggagaattga agtctgttcc cactacacaa tgtcttgaca atagcaaaaa aaatgaatct     900
cccttttgga agctttatga gtcagtgaag aaagagttgg atgtaaaatc acaaaaagaa      960
aatgtcctac agtattgtag aaaatctgga ttacaaactg attacgcaac agagaaagaa    1020
agtgctgatg gttacagggg ggagacccaa ctgttggtct cgcgtaagtc aagaccaaaa     1080
tctggtggga gcggccacgc tgtggcagag cctgcttcac ctgaacaaga gcttgaccag     1140
aacaagggga agggaagaga cgtggagtct gttcagactc ccagcaaggc tgtgggcgcc    1200
agctttcctc tctatgagcc ggctaaaatg aagaccctg tacaatattc acagcaacaa      1260
aattctccac aaaaacataa gaacaaagac ctgtatacta ctggtagaag agaatctgtg     1320
aatctgggta aaagtgaagg cttcaaggct ggtgataaaa ctcttactcc caggaagctt    1380
tcaactagaa atcgaacacc agctaaagtt gaagatgcag ctgactctgc cactaagcca     1440
gaaaatctct cttccaaaac cagaggaagt attcctacag atgtggaagt tctgcctacg    1500
gaaactgaaa ttcacaatga gccatttta actctgtggc tcactcaagt tgagaggaag     1560
atccaaaagg attccctcag caagcctgag aaattgggca ctacagctgg acagatgtgc    1620
tctgggttac ctggtcttag ttcagttgat atcaacaact ttggtgattc cattaatgag     1680
agtgagggaa taccctttgaa aagaaggcgt gtgtcctttg gtgggcacct aagacctgaa    1740
ctatttgatg aaaacttgcc tcctaatacg cctctcaaaa ggggagaagc cccaaccaaa    1800
agaaagtctc tggtaatgca cactccacct gtcctgaaga aaatcatcaa ggaacagcct    1860
caaccatcag gaaaacaaga gtcaggttca gaaatccatg tggaagtgaa ggcacaaagc   1920
ttggttataa gccctccagc tcctagtcct aggaaaactc cagttgccag tgatcaacgc    1980
```

```
cgtaggtcct gcaaaacagc ccctgcttcc agcagcaaat ctcagacaga ggttcctaag    2040
agaggaggga gaaagagtgg caacctgcct tcaaagagag tgtctatcag ccgaagtcaa    2100
catgatattt tacagatgat atgttccaaa agaagaagtg gtgcttcgga agcaaatctg    2160
attgttgcaa aatcatgggc agatgtagta aaacttggtg caaaacaaac acaaactaaa    2220
gtcataaaac atggtcctca aaggtcaatg aacaaaggc aaagaagacc tgctactcca    2280
aagaagcctg tgggcgaagt tcacagtcaa tttagtacag gccacgcaaa ctctccttgt    2340
accataataa tagggaaagc tcatactgaa aaagtacatg tgcctgctcg accctacaga    2400
gtgctcaaca acttcatttc caaccaaaaa atggacttta aggaagatct ttcaggaata    2460
gctgaaatgt tcaagacccc agtgaaggag caaccgcagt tgacaagcac atgtcacatc    2520
gctatttcaa attcagagaa tttgcttgga aaacagtttc aaggaactga ttcaggagaa    2580
gaacctctgc tccccacctc agagagtttt ggaggaaatg tgttcttcag tgcacagaat    2640
gcagcaaaac agccatctga taaatgctct gcaagccctc ccttaagacg gcagtgtatt    2700
agagaaaatg gaaacgtagc aaaaacgccc aggaacacct acaaaatgac ttctctggag    2760
acaaaaactt cagatactga gacagagcct tcaaaaacag tatccactgc aaacaggtca    2820
ggaaggtcta cagagttcag gaatatacag aagctacctg tggaaagtaa gagtgaagaa    2880
acaaatacag aaattgttga gtgcatccta aaaagaggtc agaaggcaac actactacaa    2940
caaaggagag aaggagagat gaaggaaata gaaagacctt ttgagacata taggaaaat    3000 attgaattaa agaaaacga tgaaaagatg aaagcaatga agagatcaag aacttggggg    3060
cagaaatgtg caccaatgtc tgacctgaca gacctcaaga gcttgcctga tacagaactc    3120
atgaaagaca cggcacgtgg ccagaatctc ctccaaaccc aagatcatgc caaggcacca    3180
aagagtgaga aaggcaaaat cactaaaatg ccctgccagt cattcaaacc agaaccaata    3240
aacaccccaa cacacacaaa acaacagttg aaggcatccc tggggaaagt aggtgtgaaa    3300
gaagagctcc tagcagtcgg caagttcaca cggacgtcag gggagaccac gcacacgcac    3360
agagagccag caggagatgg caagagcatc agaacgttta aggagtctcc aaagcagatc    3420
ctggacccag cagcccgtgt aactggaatg aagaagtggc caagaacgcc taaggaagag    3480
gcccagtcac tagaagacct ggctggcttc aaagagctct tccagacacc aggtccctct    3540
gaggaatcaa tgactgatga gaaaactacc aaaatagcct gcaaatctcc accaccagaa    3600
tcagtggaca ctccaacaag cacaaagcaa tggcctaaga gaagtctcag gaaagcagat    3660
gtagaggaag aattcttagc actcaggaaa ctaacaccat cagcagggaa agccatgctt    3720
acgcccaaac cagcaggagg tgatgagaaa gacattaaag catttatggg aactccagtg    3780
cagaaactgg acctggcagg aactttacct ggcagcaaaa gacagctaca gactcctaag    3840
gaaaaggccc aggctctaga gacctggct ggctttaaag agctcttcca gactcctggt    3900
cacaccgagg aattagtggc tgctggtaaa accactaaaa taccctgcga ctctccacag    3960
tcagacccag tggacacccc aacaagcaca aagcaacgac ccaagagaag tatcaggaaa    4020
gcagatgtag agggagaact cttagcgtgc aggaatctaa tgccatcagc aggcaaagcc    4080
atgcacacgc ctaaccatc agtaggtgaa gagaaagaca tcatcatatt tgtgggaact    4140
ccagtgcaga aactggacct gacagagaac ttaaccggca gcaagagacg gccacaaact    4200
cctaaggaag aggcccaggc tctggaagac ctgactggct ttaaagagct cttccagacc    4260
cctggtcata ctgaagaagc agtggctgct ggcaaaacta ctaaaatgcc ctgcgaatct    4320
```

```
tctccaccag aatcagcaga caccccaaca agcacaagaa ggcagcccaa gacaccttttg    4380 gagaaaaggg acgtacagaa ggagctctca gccctgaaga agctcacaca gacatcaggg    4440
gaaaccacac acacagataa agtaccagga ggtgaggata aaagcatcaa cgcgtttagg    4500
gaaactgcaa aacagaaact ggacccagca gcaagtgtaa ctggtagcaa gaggcaccca    4560
aaaactaagg aaaaggccca acccctagaa gacctggctg gcttgaaaga gctcttccag    4620
acaccagtat gcactgacaa gcccacgact cacgagaaaa ctaccaaaat agcctgcaga    4680
tcacaaccag acccagtgga cacaccaaca agctccaagc cacagtccaa gagaagtctc    4740
aggaaagtgg acgtagaaga agaattcttc gcactcagga acgaacacc atcagcaggc     4800 aaagccatgc acacacccaa accagcagta agtggtgaga aaaacatcta cgcatttatg    4860
ggaactccag tgcagaaact ggacctgaca gagaacttaa ctggcagcaa gagacggcta    4920
caaactccta aggaaaaggc ccaggctcta gaagacctgg ctggctttaa agagctcttc    4980
cagacacgag gtcacactga ggaatcaatg actaacgata aaactgccaa agtagcctgc    5040
aaatcttcac aaccagaccc agacaaaaac ccagcaagct ccaagcgacg gctcaagaca    5100
tccctgggga agtgggcgt gaaagaagag ctcctagcag ttggcaagct cacacagaca     5160
tcaggagaga ctacacacac acacacagag ccaacggaga tggtaagag catgaaagca     5220 tttatggagt ctccaaagca gatcttagac tcagcagcaa gtctaactgg cagcaagagg    5280
cagctgagaa ctcctaaggg aaagtctgaa gtccctgaag acctggccgg cttcatcgag    5340
ctcttccaga caccaagtca cactaaggaa tcaatgacta acgaaaaaac taccaaagta    5400
tcctacagag cttcacagcc agacctagtg gacacccca caagctccaa gccacagccc     5460
aagagaagtc tcaggaaagc agacactgaa gaagaatttt tagcatttag gaaacaaacg    5520
ccatcagcag gcaaagccat gcacacaccc aaaccagcag taggtgaaga gaaagacatc    5580
aacacgtttt tgggaactcc agtgcagaaa ctggaccagc caggaaattt acctggcagc    5640
aatagacggc tacaaactcg taaggaaaag gcccaggctc tagaagaact gactggcttc    5700
agagagcttt tccagacacc atgcactgat aaccccacga ctgatgagaa aactaccaaa    5760
aaaatactct gcaaatctcc gcaatcgac ccagcggaca ccccaacaaa cacaaagcaa     5820
cggcccaaga gaagcctcaa gaaagcagac gtagaggaag aatttttagc attcaggaaa    5880
ctaacaccat cagcaggcaa agccatgcac acgcctaaag cagcagtagg tgaaagaaa     5940 gacatcaaca catttgtggg gactccagtg gagaaactgg acctgctagg aaatttacct    6000
ggcagcaaga gacggccaca aactcctaaa gaaaaggcca aggctctaga agatctggct    6060
ggcttcaaag agctcttcca gacaccaggt cacactgagg aatcaatgac cgatgacaaa    6120
atcacagaag tatcctgcaa atctccacaa ccagacccag tcaaaacccc aacaagctcc    6180
aagcaacgac tcaagatatc cttggggaaa gtaggtgtga agaagaggt cctaccagtc     6240 ggcaagctca cacagacgtc agggaagacc acacagacac acagagagac agcaggagat    6300
ggaaagagca tcaaagcgtt taaggaatct gcaaagcaga tgctggaccc agcaaactat    6360
ggaactggga tggagaggtg gccaagaaca cctaaggaag aggcccaatc actagaagac    6420
ctggccggct tcaagagct cttccagaca ccagaccaca ctgaggaatc aacaactgat     6480
gacaaaacta ccaaaatagc ctgcaaatct ccaccaccag aatcaatgga cactccaaca    6540
agcacaagga ggcggcccaa aacacctttg ggaaaagggg atatagtgga agagctctca    6600
gccctgaagc agctcacaca gaccacacac acagacaaag taccaggaga tgaggataaa    6660
ggcatcaacg tgttcaggga aactgcaaaa cagaaactgg acccagcagc aagtgtaact    6720
```

```
ggtagcaaga ggcagccaag aactcctaag ggaaaagccc aacccctaga agacttggct    6780
ggcttgaaag agctcttcca gacaccaata tgcactgaca agcccacgac tcatgagaaa    6840
actaccaaaa tagcctgcag atctccacaa ccagacccag tgggtacccc aacaatcttc    6900
aagccacagt ccaagagaag tctcaggaaa gcagacgtag aggaagaatc cttagcactc    6960
aggaaacgaa caccatcagt agggaaagct atggacacac ccaaccagc aggaggtgat     7020 gagaaagaca tgaaagcatt tatgggaact ccagtgcaga aattggacct gccaggaaat    7080
ttacctggca gcaaaagatg gccacaaact cctaaggaaa aggcccaggc tctagaagac    7140
ctggctggct tcaaagagct cttccagaca ccaggcactg acaagcccac gactgatgag    7200
aaaactacca aaatagcctg caaatctcca caaccagacc cagtggacac cccagcaagc    7260
acaaagcaac ggcccaagag aaacctcagg aaagcagacg tagaggaaga atttttagca    7320
ctcaggaaac gaacaccatc agcaggcaaa gccatggaca caccaaaacc agcagtaagt    7380
gatgagaaaa atatcaacac atttgtggaa actccagtgc agaaactgga cctgctagga    7440
aatttacctg gcagcaagag acagccacag actcctaagg aaaaggctga ggctctagag    7500
gacctggttg gcttcaaaga actcttccag acaccaggtc acactgagga atcaatgact    7560
gatgacaaaa tcacagaagt atcctgtaaa tctccacagc cagagtcatt caaaacctca    7620
agaagctcca agcaaaggct caagataccc ctggtgaaag tggacatgaa agaagagccc    7680
ctagcagtca gcaagctcac acggacatca ggggagacta cgcaaacaca cacagagcca    7740
acaggagata gtaagagcat caaagcgttt aaggagtctc caaagcagat cctggaccca    7800
gcagcaagtg taactggtag caggaggcag ctgagaactc gtaaggaaaa ggcccgtgct    7860
ctagaagacc tggttgactt caaagagctc ttctcagcac caggtcacac tgaagagtca    7920
atgactattg acaaaaacac aaaaattccc tgcaaatctc ccccaccaga actaacagac    7980
actgccacga gcacaaagag atgccccaag acacgtccca ggaaagaagt aaaagaggag    8040
ctctcagcag ttgagaggct cacgcaaaca tcagggcaaa gcacacacac acacaaagaa    8100
ccagcaagcg gtgatgaggg catcaaagta ttgaagcaac gtgcaaagaa gaaaccaaac    8160
ccagtagaag aggaacccag caggagaagg ccaagagcac taaggaaaaa ggcccaaccc    8220
ctggaagacc tggccggctt cacagagctc tctgaaacat caggtcacac tcaggaatca    8280
ctgactgctg gcaaagccac taaaataccc tgcgaatctc ccccactaga agtggtagac    8340
accacagcaa gcacaaagag gcatctcagg acacgtgtgc agaaggtaca agtaaaagaa    8400
gagccttcag cagtcaagtt cacacaaaca tcaggggaaa ccacggatgc agacaaagaa    8460
ccagcaggtg aagataaagg catcaaagca ttgaggaat ctgcaaaaca gacaccggct     8520
ccagcagcaa gtgtaactgg cagcaggaga cggccaagag cacccaggga agtgcccaa    8580 gccatagaag acctagctgg cttcaaagac ccagcagcag gtcacactga gaatcaatg    8640 actgatgaca aaaccactaa aatacccctgc aaatcatcac cagaactaga agacaccgca   8700
acaagctcaa agagacggcc caggacacgt gcccagaaag tagaagtgaa ggaggagctg    8760
ttagcagttg gcaagctcac acaaacctca ggggagacca cgcacaccga caagagccg     8820 gtaggtgagg gcaaaggcac gaaagcattt aagcaacctg caaagcggaa gctgacgca    8880 gaagatgtaa ttggcagcag gagacagcca agagcaccta ggaaaaggc ccaacccctg     8940 gaagatctgg ccagcttcca agagctctct caaacaccag gccacactga ggaactggca    9000
aatggtgctg ctgatagctt tacaagcgct ccaaagcaaa cacctgacag tggaaaacct    9060
```

```
ctaaaaatat ccagaagagt tcttcgggcc cctaaagtag aacccgtggg agacgtggta    9120
agcaccagag accctgtaaa atcacaaagc aaaagcaaca cttccctgcc cccactgccc    9180
ttcaagaggg gaggtggcaa agatggaagc gtcacgggaa ccaagaggct gcgctgcatg    9240
ccagcaccag aggaaattgt ggaggagctg ccagccagca agaagcagag ggttgctccc    9300
agggcaagag gcaaatcatc cgaacccgtg gtcatcatga agagaagttt gaggacttct    9360
gcaaaaagaa ttgaacctgc ggaagagctg aacagcaacg acatgaaaac caacaaagag    9420
gaacacaaat tacaagactc ggtccctgaa aataagggaa tatccctgcg ctccagacgc    9480
caaaataaga ctgaggcaga acagcaaata actgaggtct ttgtattagc agaaagaata    9540
gaaataaaca gaaatgaaaa aagcccatg aagacctccc cagagatgga cattcagaat    9600
ccagatgatg gagcccggaa acccatacct agagacaaag tcactgagaa caaaaggtgc    9660
ttgaggtctg ctagacagaa tgagagctcc cagcctaagg tggcagagga gagcggaggg    9720
cagaagagtg cgaaggttct catgcagaat cagaaaggga aggagaagc aggaaattca    9780 gactccatgt gcctgagatc aagaaagaca aaaagccagc ctgcagcaag cactttggag    9840
agcaaatctg tgcagagagt aacgcggagt gtcaagaggt gtgcagaaaa tccaaagaag    9900
gctgaggaca atgtgtgtgt caagaaaata agaaccagaa gtcataggga cagtgaagat    9960
atttgacaga aaaatcgaac tgggaaaaat ataataaagt tagttttgtg ataagttcta    10020
gtgcagtttt tgtcataaat tacaagtgaa ttctgtaagt aaggctgtca gtctgcttaa    10080
gggaagaaaa ctttggattt gctgggtctg aatcggcttc ataaactcca ctgggagcac    10140
tgctgggctc ctggactgag aatagttgaa caccgggggc tttgtgaagg agtctgggcc    10200
aaggtttgcc ctcagctttg cagaatgaag ccttgaggtc tgtcaccacc cacagccacc    10260
ctacagcagc cttaactgtg acacttgcca cactgtgtcg tcgtttgttt gcctatgtcc    10320
tccagggcac ggtggcagga acaactatcc tcgtctgtcc caacactgag caggcactcg    10380
gtaaacacga atgaatggat gagcgcacgg atgaatggag cttacaagat ctgtctttcc    10440
aatggccggg ggcatttggt ccccaaatta aggctattgg acatctgcac aggacagtcc    10500
tatttttgat gtcctttcct ttctgaaaat aaagttttgt gctttggaga atgactcgtg    10560
agcacatctt tagggaccaa gagtgacttt ctgtaaggag tgactcgtgg cttgccttgg    10620
tctcttggga atacttttct aactagggtt gctctcacct gagacattct ccacccgcgg    10680
aatctcaggg tcccaggctg tgggccatca cgacctcaaa ctggctccta atctccagct    10740
ttcctgtcat tgaaagcttc ggaagtttac tggctctgct cccgcctgtt ttctttctga    10800
ctctatctgg cagcccgatg ccacccagta caggaagtga caccagtact ctgtaaagca    10860
tcatcatcct tggagagact gagcactcag caccttcagc cacgatttca ggatcgcttc    10920
cttgtgagcc gctgcctccg aaatctcctt tgaagcccag acatctttct ccagcttcag    10980
acttgtagat ataactcgtt catcttcatt tactttccac tttgccccct gtcctctctg    11040
tgttccccaa atcagagaat agcccgccat cccccaggtc acctgtctgg attcctcccc    11100
attcacccac cttgccaggt gcaggtgagg atggtgcacc agacagggta gctgtccccc    11160
aaaatgtgcc ctgtgcgggc agtgcccgt ctccacgttt gtttcccag tgtctggcgg    11220 ggagccaggt gacatcataa atacttgctg aatgaatgca gaaatcagcg gtactgactt    11280
gtactatatt ggctgccatg ataggggttct cacagcgtca tccatgatcg taagggagaa    11340
tgacattctg cttgagggag ggaatagaaa ggggcaggga ggggacatct gagggcttca    11400
cagggctgca aagggtacag ggattgcacc agggcagaac aggggagggt gttcaaggaa    11460
```

```
gagtggctct tagcagaggc actttggaag gtgtgaggca taaatgcttc cttctacgta    11520
ggccaacctc aaaactttca gtaggaatgt tgctatgatc aagttgttct aacactttag    11580
acttagtagt aattatgaac ctcacataga aaaatttcat ccagccatat gcctgtggag    11640
tggaatattc tgtttagtag aaaaatcctt tagagttcag ctctaaccag aaatcttgct    11700
gaagtatgtc agcacctttt ctcaccctgg taagtacagt atttcaagag cacgctaagg    11760
gtggttttca ttttacaggg ctgttgatga tgggttaaaa atgttcattt aagggctacc    11820
cccgtgttta atagatgaac accacttcta cacaaccctc cttggtactg ggggagggag    11880
agatctgaca aatactgccc attccccctag gctgactgga tttgagaaca aatacccacc    11940
catttccacc atggtatggt aacttctctg agcttcagtt tccaagtgaa tttccatgta    12000
ataggacatt cccattaaat acaagctgtt tttactttttt cgcctcccag ggcctgtggg    12060
atctggtccc ccagcctctc ttgggctttc ttacactaac tctgtaccta ccatctcctg    12120
cctcccttag gcaggcacct ccaaccacca cacactccct gctgttttcc ctgcctggaa    12180
ctttccctcc tgccccacca agatcatttc atccagtcct gagctcagct taagggaggc    12240
ttcttgcctg tgggttccct caccccatg cctgtcctcc aggctgggc aggttcttag    12300 tttgcctgga attgttctgt acctctttgt agcacgtagt gttgtggaaa ctaagccact    12360
aattgagttt ctggctcccc tcctgggggtt gtaagttttg ttcattcatg agggccgact    12420
gcatttcctg gttactctat cccagtgacc agccacagga gatgtccaat aaagtatgtg    12480
atgaaatggt cttaaaaaaa aaaaaaa                                        12507

<210> SEQ ID NO 13
<211> LENGTH: 2161
<212> TYPE: DNA
<213> ORGANISM: Homo sapiens

<400> SEQUENCE: 13
gcgacggtta acgggggccc aaggcagggg tggcgggtca gtgctgctcg ggggcttctc      60
catccaggtc cctggagttc ctggtccctg gagctccgca cttggcggcg caacctgcgt     120
gaggcagcgc gactctggcg actggccggc catgccttcc cgggctgagg actatgaagt     180
gttgtacacc attggcacag gctcctacgg ccgctgccag aagatccgga ggaagagtga     240
tggcaagata ttagttttgga aagaacttga ctatggctcc atgacagaag ctgagaaaca     300
gatgcttgtt tctgaagtga atttgcttcg tgaactgaaa catccaaaca tcgttcgtta     360
ctatgatcgg attattgacc ggaccaatac aacactgtac attgtaatgg aatattgtga     420 aggagggggat ctggctagtg taattacaaa gggaaccaag gaaaggcaat acttagatga     480
agagtttgtt cttcgagtga tgactcagtt gactctggcc ctgaaggaat gccacagacg     540
aagtgatggt ggtcataccg tattgcatcg ggatctgaaa ccagccaatg ttttcctgga     600
tggcaagcaa aacgtcaagc ttggagactt gggctagct agaatattaa accatgacac     660
gagttttgca aaaacatttg ttggcacacc ttattacatg tctcctgaac aaatgaatcg     720
catgtcctac aatgagaaat cagatatctg gtcattgggc tgcttgctgt atgagttatg     780
tgcattaatg cctccatta cagcttttag ccagaaagaa ctcgctggga aaatcagaga     840
aggcaaattc aggcgaattc ataccgttta ctctgatgaa ttgaatgaaa ttattacgag     900
gatgttaaac ttaaaggatt accatcgacc ttctgttgaa gaaattcttg agaacccttt     960
aatagcagat ttggttgcag acgagcaaag aagaaatctt gagagaagag ggcgacaatt    1020
```

```
aggagagcca gaaaaatcgc aggattccag ccctgtattg agtgagctga aactgaagga    1080
aattcagtta caggagcgag agcgagctct caaagcaaga gaagaaagat tggagcagaa    1140
agaacaggag ctttgtgttc gtgagagact agcagaggac aaactggcta gagcagaaaa    1200
tctgttgaag aactacagct tgctaaagga acggaagttc ctgtctctgg caagtaatcc    1260
agaacttctt aatcttccat cctcagtaat aagaagaaa gttcatttca gtggggaaag    1320
taaagagaac atcatgagga gtgagaattc tgagagtcag ctcacatcta agtccaagtg    1380
caaggacctg aagaaaaggc ttcacgctgc ccagctgcgg gctcaagccc tgtcagatat    1440
tgagaaaaat taccaactga aaagcagaca gatcctgggc atgcgctagc caggtagaga    1500
gacacagagc tgtgtacagg atgtaatatt accaaccttt aaagactgat attcaaatgc    1560
tgtagtgttg aatacttggt tccatgagcc atgcctttct gtatagtaca catgatattt    1620
cggaattggt tttactgttc ttcagcaact attgtacaaa atgttcacat ttaattttc    1680 tttcttcttt taagaacata ttataaaaag aatactttct tggttgggct tttaatcctg    1740
tgtgtgatta ctagtaggaa catgagatgt gacattctaa atcttgggag aaaaaataat    1800
gttaggaaaa aaatatttat gcaggaagag tagcactcac tgaatagttt taaatgactg    1860
agtggtatgc ttcaattgt catgtctaga tttaaatttt aagtctgaga ttttaaatgt    1920
ttttgagctt agaaaaccca gttagatgca atttggtcat taataccatg acatcttgct    1980
tataaatatt ccattgctct gtagttcaaa tctgttagct ttgtgaaaat tcatcactgt    2040
gatgtttgta ttcttttttt ttttctgttt aacagaatat gagctgtctg tcatttacct    2100
acttctttcc cactaaataa aagaattctt cagtttccct gtaaaaaaaa aaaaaaaaa    2160 a                                                                    2161

<210> SEQ ID NO 14
<211> LENGTH: 2471
<212> TYPE: DNA
<213> ORGANISM: Homo sapiens

<400> SEQUENCE: 14
gcgttacagg ccctttggcg cctgcgtatt cgtgaagtgt gaaaaaagcg cgcctctgtt      60
gggacgggaa atcagccttt ctattggtca gggttagaaa ccccgccttt gaggcatttt     120
caaccaatgg aagcgcggca ttcttcattt aaactgtcta taaatttctg cctagtcaaa     180
gttaagagtg gcgccaggga tttgaaccgc gctgacgaag tttggtgatc catcttccga     240
gtatcgccgg gatttcgaat cgcgatgatc atcccctctc tagaggagct ggactccctc     300
aagtacagtg acctgcagaa cttagccaag agtctgggtc tccgggccaa cctgagggca     360
accaagttgt taaagccctt gaaaggctac attaaacatg aggcaagaaa aggaaatgag     420
aatcaggatg aaagtcaaac ttctgcatcc tcttgtgatg agactgagat acagatcagc     480
aaccaggaag aagctgagag acagccactt ggccatgtca ccaaaacaag agaaggtgc      540 aagactgtcc gtgtggaccc tgactcacag cagaatcatt cagagataaa aataagtaat     600
cccactgaat tccagaatca tgaaaagcag gaaagccagg atctcagagc tactgcaaaa     660
gttccttctc caccagacga gcaccaagaa gctgagaatg ctgtttcctc aggtaacaga     720
gattcaaagg taccttcaga aggaaagaaa tctctctaca cagatgagtc atccaaacct     780
ggaaaaaata aaagaactgc aatcactact ccaaacttta agaagcttca tgaagctcat     840
tttaaggaaa tggagtccat tgatcaatat attgagagaa aaagaaaca ttttgaagaa     900 cacaattcca tgaatgaact gaagcagcag cccatcaata agggaggggt caggactcca     960
```

```
gtacctccaa gaggaagact ctctgtggct tctactccca tcagccaacg acgctcgcaa    1020
ggccggtctt gtggccctgc aagtcagagt accttgggtc tgaaggggtc actcaagcgc    1080
tctgctatct ctgcagctaa aacgggtgtc aggttttcag ctgctactaa agataatgag    1140
cataagcgtt cactgaccaa gactccagcc agaaagtctg cacatgtgac cgtgtctggg    1200
ggcaccccaa aaggcgaggc tgtgcttggg acacacaaat taaagaccat cacggggaat    1260
tctgctgctg ttattacccc attcaagttg acaactgagg caacgcagac tccagtctcc    1320
aataagaaac cagtgtttga tcttaaagca gtttgtctc gtccctcaa ctatgaacca      1380 cacaaaggaa agctaaaacc atgggggcaa tctaaagaaa ataattatct aaatcaacat    1440
gtcaacagaa ttaacttcta caagaaaact acaaacaac cccatctcca gacaaaggaa     1500
gagcaacgga gaaacgcga gcaagaacga aggagaaga aagcaaaggt tttgggaatg      1560
cgaaggggcc tcattttggc tgaagattaa taatttttta acatcttgta aatattcctg    1620
tattctcaac ttttttcctt ttgtaaattt tttttttttg ctgtcatccc cactttagtc    1680
acgagatctt tttctgctaa ctgttcatag tctgtgtagt gtccatgggt tcttcatgtg    1740
ctatgatctc tgaaaagacg ttatcacctt aaagctcaaa ttctttggga tggttttttac   1800 ttaagtccat taacaattca ggtttctaac gagacccatc ctaaaattct gtttctagat    1860
ttttaatgtc aagttcccaa gttccccctg ctggttctaa tattaacaga actgcagtct    1920
tctgctagcc aatagcattt acctgatggc agctagttat gcaagcttca ggagaatttg    1980
aacaataaca agaatagggt aagctgggat agaaaggcca cctcttcact ctctatagaa    2040
tatagtaacc tttatgaaac ggggccatat agtttggtta tgacatcaat attttaccta   2100
ggtgaaattg tttaggctta tgtaccttcg ttcaaatatc ctcatgtaat tgccatctgt    2160
cactcactat attcacaaaa ataaaactct acaactcatt ctaacattgc ttacttaaaa    2220
gctacatagc cctatcgaaa tgcgaggatt aatgctttaa tgcttttaga gacagggtct    2280
cactgtgttg cccaggctgg tctcaaactc caccaaatgt acttcttatt cattttatgg    2340
aaaagactag gctttgctta gtatcatgtc catgttcct tcacctcagt ggagcttctg     2400
agttttatac tgctcaagat cgtcataaat aaaattttt ctcattgtca tagaaaaaaa    2460
aaaaaaaaaa a                                                         2471
```

<210> SEQ ID NO 15  
<211> LENGTH: 1249  
<212> TYPE: DNA  
<213> ORGANISM: Homo sapiens

<400> SEQUENCE: 15

```
gagctgtgct tggggcgggg cctggcgtgt attcgaaagg aaggcgccgg ctgcgggaag      60
atggcggctc agccgctgcg gcatcgctca cgttgtgcaa cgccgccccg ggggacttt     120 tgtggtggca ctgagagggc gattgaccaa gcttctttta cgacctccat ggagtgggat    180
acgcaggtgg tgaaggggtc ctcgccgctc ggccccgcag ggctgggggc tgaggagcca    240
gccgccggcc cgcagctgcc gtcttggctg cagcctgaga ggtgcgctgt gttccagtgc    300
gcacagtgtc acgcagtgct cgccgactcg gtgcacctcg cctgggacct gtcgcggtcc    360
ctcggggccg tggtcttctc cagagttaca aataacgtcg ttttggaagc gcccttccta    420
gttggcattg aaggttcact caaaggcagt acttacaacc ttttattctg tggttcttgt    480
gggattcccg ttggtttcca tctgtattct acccatgctg ccctggctgc cttgagaggt    540
```

| | |
|---|---:|
| cacttctgcc tttccagtga caaaatggtg tgctatctct taaaaacaaa agccatagta | 600 |
| aatgcatcag agatggatat tcaaaatgtt cctctatcag aaaagattgc agagctgaaa | 660 |
| gagaagatag tgctaacgca caatcgctta aaatcactaa tgaagattct gagtgaagtg | 720 |
| actcctgacc agtccaagcc agaaaactga tcctgtacca agcttgagt gtcaggttca | 780 |
| ggctttattg ctgtcttcaa caacaggtgc tgcttagtca tttcttgaaa aagattggct | 840 |
| tcaagaatgg aggggaaatg cagtttctat ttacctttag gctgattttc caaattattt | 900 |
| gtgaagctgt ttttagaaga tgagagacta aggattcttc tcttttatag ctatttgcct | 960 |
| taagaactta ctttagattc ttattgaatt cataatactt atctctgaaa atgtctttga | 1020 |
| ctgtaaattt aggaattaag atgcagagtc ccatgtgtcc tctgatctaa agttgcatgg | 1080 |
| ttggtctgaa aatagagttg gcttaatgt tgacttctat tactcctgca tggagcagtt | 1140 |
| gttatgaata ctaatacatc acttttttaac ttctgtaaaa tacagatcat aatattctat | 1200 |
| aggtaatgtt taataaattg cctgaataat atacaaaaaa aaaaaaaaa | 1249 |

<210> SEQ ID NO 16
<211> LENGTH: 3207
<212> TYPE: DNA
<213> ORGANISM: Homo sapiens

<400> SEQUENCE: 16

| | |
|---|---:|
| gattgcgcac ccgcgacttc agcccgaggg gcggggattt tcttggagcg acgggacgcg | 60 |
| acgccaatcg cgacgaggct tcgccccgtg gcgcggtttg aaattttgcg gggctcaacg | 120 |
| gctcgcggag cggctacgcg gagtgacatc gccggtgttt gcgggtggtt gttgctctcg | 180 |
| gggccgtgtg gagtaggtct ggacctggac tcacggctgc ttggagcgtc cgccatgagg | 240 |
| agaagtgagg tgctggcgga ggagtccata gtatgtctgc agaaagccct aaatcacctt | 300 |
| cgggaaatat gggagctaat tgggattcca gaggaccagc ggttacaaag aactgaggtg | 360 |
| gtaaagaagc atatcaagga actcctggat atgatgattg ctgaagagga aagcctgaag | 420 |
| gaaagactca tcaaaagcat atccgtctgt cagaaagagc tgaacactct gtgcagcgag | 480 |
| ttacatgttg agccatttca ggaagaagga gagacgacca tcttgcaact agaaaaagat | 540 |
| ttgcgcaccc aagtggaatt gatgcgaaaa cagaaaaagg agagaaaaca ggaactgaag | 600 |
| ctacttcaag agcaagatca agaactgtgc gaaattcttt gtatgcccca ctatgatatt | 660 |
| gacagtgcct cagtgcccag cttagaagag ctgaaccagt tcaggcaaca tgtgacaact | 720 |
| ttgagggaaa caaaggcttc taggcgtgag gagtttgtca gtataaagag acagatcata | 780 |
| ctgtgtatgg aagaattaga ccacaccca gacacaagct ttgaaagaga tgtggtgtgt | 840 |
| gaagacgaag atgcctttg tttgtctttg gagaatattg caacactaca aaagttgcta | 900 |
| cggcagctgg aaatgcagaa atcacaaaat gaagcagtgt gtgagggct gcgtactcaa | 960 |
| atccgagagc tctgggacag gttgcaaata cctgaagaag aaagagaagc tgtggccacc | 1020 |
| attatgtctg ggtcaaaggc caaggtccgg aaagcgctgc aattagaagt ggatcggttg | 1080 |
| gaagaactga aaatgcaaaa catgaagaaa gtgattgagg caattcgagt ggagctggtt | 1140 |
| cagtactggg accagtgctt ttatagccag gagcagagac aagcttttgc ccctttctgt | 1200 |
| gctgaggact acacagaaag tctgctccag ctccacgatg ctgagattgt gcggttaaaa | 1260 |
| aactactatg aagttcacaa ggaactcttt gaaggtgtcc agaagtggga agaaacctgg | 1320 |
| aggcttttct tagagtttga gagaaaagct tcagatccaa atcgatttac aaaccgagga | 1380 |
| ggaaatcttc taaaagaaga aaacaacga gccaagctcc agaaaatgct gcccaagctg | 1440 |

-continued

```
gaagaagagt tgaaggcacg aattgaattg tgggaacagg aacattcaaa ggcatttatg    1500
gtgaatgggc agaaattcat ggagtatgtg gcagaacaat gggagatgca tcgattggag    1560
aaagagagag ccaagcagga aagacaactg aagaacaaaa aacagacaga gacagagatg    1620
ctgtatggca gcgctcctcg aacacctagc aagcggcgag gactggctcc caatacaccg    1680
ggcaaagcac gtaagctgaa cactaccacc atgtccaatg ctacggccaa tagtagcatt    1740
cggcctatct ttggagggac agtctaccac tcccccgtgt ctcgacttcc tccttctggc    1800
agcaagccag tcgctgcttc cacctgttca gggaagaaaa caccccgtac tggcaggcat    1860
ggagccaaca aggagaacct ggagctcaac ggcagcatcc tgagtggtgg gtaccctggc    1920 tcggccccccc tccagcgcaa cttcagcatt aattctgttg ccagcaccta ttctgagttt    1980
gcgaaggatc cgtccctctc tgacagttcc actgttgggc ttcagcgaga actttcaaag    2040
gcttccaaat ctgatgctac ttctggaatc ctcaattcaa ccaacatcca gtcctgagaa    2100
gccctgatca gtcaaccagc tgtggcttcc tgtgcctaga ctggacctaa ttatatgggg    2160
gtgactttag tttttcttca gcttaggcgt gcttgaaacc ttggccaggt tccatgacca    2220
tgggcctaac ttaaagatgt gaatgagtgt tacagttgaa agcccatcat aggtttagtg    2280
gtcctaggag acttggtttt gacttatata catgaaaagt ttatggcaag aagtgcaaat    2340
tttagcatat ggggcctgac ttctctacca cataattcta cttgctgaag catgatcaaa    2400
gcttgtttta tttcaccact gtaggaaaat gattgactat gcccatccct gggggtaatt    2460
ttggcatgta tacctgtaac tagtaattaa catctttttt gtttaggcat gttcaattaa    2520
tgctgtagct atcatagctt tgctcttacc tgaagccttg tccccaccac acaggacagc    2580
cttcctcctg aagagaatgt ctttgtgtgt ccgaagttga gatggcctgc cctactgcca    2640
aagaggtgac aggaaggctg ggagcagctt tgttaaattg tgttcagttc tgttacacag    2700
tgcattgccc tttgttgggg gtatgcatgt atgaacacac atgcttgtcg gaacgctttc    2760
tcggcgtttg tcccttggct ctcatctccc ccattcctgt gcctactttg cctgagttct    2820 tctaccccccg cagttgccag ccacattggg agtctgtttg ttccaatggg ttgagctgtc    2880
tttgtcgtgg agatctggaa ctttgcacat gtcactactg gggaggtgtt cctgctctag    2940
cttccacgat gaggcgccct ctttacctat cctctcaatc actactcttc ttgaagcact    3000
attatttatt cttccgctgt ctgcctgcag cagtactact gtcaacatag tgtaaatggt    3060
tctcaaaagc ttaccagtgt ggacttggtg ttagccacgc tgtttactca tacagtacgt    3120
gtcctgtttt taaaatatac aattattctt aaaaataaat taaaatctgt atacttacat    3180
ttcaaaaaga aaaaaaaaa aaaaaaa                                         3207
```

<210> SEQ ID NO 17
<211> LENGTH: 3284
<212> TYPE: DNA
<213> ORGANISM: Homo sapiens

<400> SEQUENCE: 17

```
cccgtgcacc ctgtcccagc cgtcctgtcc tggctgctcg ctctgcttcg ctgcgcctcc      60
actatgctct ccctccgtgt cccgctcgcg cccatcacgg accgcagca gctgcagctc     120 tcgccgctga aggggctcag cttggtcgac aaggagaaca cgccgccggc cctgagcggg     180
acccgcgtcc tggccagcaa gaccgcgagg aggatcttcc aggagcccac ggagccgaaa     240
actaaagcag ctgcccccgg cgtggaggat gagccgctgc tgagagaaaa ccccccgccgc     300
```

```
tttgtcatct tccccatcga gtaccatgat atctggcaga tgtataagaa ggcagaggct    360
tccttttgga ccgccgagga ggtggacctc tccaaggaca ttcagcactg ggaatccctg    420
aaacccgagg agagatattt tatatcccat gttctggctt tctttgcagc aagcgatggc    480
atagtaaatg aaaacttggt ggagcgattt agccaagaag ttcagattac agaagcccgc    540
tgtttctatg gcttccaaat tgccatggaa acatacatt ctgaaatgta tagtcttctt    600
attgacactt acataaaaga tcccaaagaa agggaatttc tcttcaatgc cattgaaacg    660
atgccttgtg tcaagaagaa ggcagactgg gccttgcgct ggattgggga caaagaggct    720
acctatggtg aacgtgttgt agcctttgct gcagtggaag gcattttctt ttccggttct    780
tttgcgtcga tattctggct caagaaacga ggactgatgc ctggcctcac attttctaat    840
gaacttatta gcagagatga gggtttacac tgtgattttg cttgcctgat gttcaaacac    900
ctggtacaca aaccatcgga ggagagagta agagaaataa ttatcaatgc tgttcggata    960
gaacaggagt tcctcactga ggccttgcct gtgaagctca ttgggatgaa ttgcactcta   1020
atgaagcaat acattgagtt tgtggcagac agacttatgc tggaactggg ttttagcaag   1080
gttttcagag tagagaaccc atttgacttt atggagaata tttcactgga aggaaagact   1140
aacttctttg agaagagagt aggcgagtat cagaggatgg gagtgatgtc aagtccaaca   1200
gagaattctt ttaccttgga tgctgacttc taaatgaact gaagatgtgc ccttacttgg   1260 ctgattttt ttttccatct cataagaaaa atcagctgaa gtgttaccaa ctagccacac   1320
catgaattgt ccgtaatgtt cattaacagc atctttaaaa ctgtgtagct acctcacaac   1380
cagtcctgtc tgtttatagt gctggtagta tcaccttttg ccagaaggcc tggctggctg   1440
tgacttacca tagcagtgac aatggcagtc ttggctttaa agtgaggggt gaccctttag   1500
tgagcttagc acagcgggat taaacagtcc tttaaccagc acagccagtt aaaagatgca   1560
gcctcactgc ttcaacgcag attttaatgt ttacttaaat ataaacctgg cactttacaa   1620
acaaataaac attgtttgta ctcacaaggc gataatagct tgatttattt ggtttctaca   1680
ccaaatacat tctcctgacc actaatggga gccaattcac aattcactaa gtgactaaag   1740
taagttaaac ttgtgtagac taagcatgta atttttaagt tttatttaa tgaattaaaa    1800 tatttgttaa ccaactttaa agtcagtcct gtgtatacct agatattagt cagttggtgc   1860
cagatagaag acaggttgtg tttttatcct gtggcttgtg tagtgtcctg ggattctctg   1920
ccccctctga gtagagtgtt gtgggataaa ggaatctctc agggcaagga gcttcttaag   1980
ttaaatcact agaaatttag gggtgatctg ggccttcata tgtgtgagaa gccgtttcat   2040
tttatttctc actgtatttt cctcaacgtc tggttgatga gaaaaaattc ttgaagagtt   2100
ttcatatgtg ggagctaagg tagtattgta aaatttcaag tcatccttaa acaaaatgat   2160
ccacctaaga tcttgcccct gttaagtggt gaaatcaact agaggtggtt cctacaagtt   2220
gttcattcta gttttgtttg gtgtaagtag gttgtgtgag ttaattcatt tatatttact   2280
atgtctgtta aatcagaaat ttttattat ctatgttctt ctagatttta cctgtagttc   2340
atacttcagt cacccagtgt cttattctgg cattgtctaa atctgagcat tgtctagggg   2400
gatcttaaac tttagtagga aaccatgagc tgttaataca gtttccattc aaatattaat   2460
ttcagaatga aacataattt ttttttttt ttttgagatg gagtctcgct ctgttgccca   2520
ggctggagtg cagtggcgcg attttggctc actgtaacct ccatctcctg ggttcaagca   2580
attctcctgt ctcagcctcc ctagtagctg ggactgcagg tatgtgctac cacacctggc   2640
taatttttgt attttagta gagatggagt ttcaccatat tggtcaggct ggtcttgaac   2700
```

| | |
|---|---|
| tcctgacctc aggtgatcca cccacctcgg cctcccaaag tgctgggatt gcaggcgtga | 2760 |
| taaacaaata ttcttaatag ggctactttg aattaatctg cctttatgtt tgggagaaga | 2820 |
| aagctgagac attgcatgaa agatgatgag agataaatgt tgatcttttg gccccatttg | 2880 |
| ttaattgtat tcagtatttg aacgtcgtcc tgtttattgt tagttttctt catcatttat | 2940 |
| tgtatagaca attttaaat ctctgtaata tgatacattt tcctatcttt taagttattg | 3000 |
| ttacctaaag ttaatccaga ttatatggtc cttatatgtg tacaacatta aaatgaaagg | 3060 |
| ctttgtcttg cattgtgagg tacaggcgga agttggaatc aggttttagg attctgtctc | 3120 |
| tcattagctg ataatgtga ggattaactt ctgccagctc agaccatttc ctaatcagtt | 3180 |
| gaaagggaaa caagtatttc agtctcaaaa ttgaataatg cacaagtctt aagtgattaa | 3240 |
| aataaaactg ttcttatgtc agtttcaaaa aaaaaaaaaa aaaa | 3284 |

<210> SEQ ID NO 18
<211> LENGTH: 2355
<212> TYPE: DNA
<213> ORGANISM: Homo sapiens

<400> SEQUENCE: 18

| | |
|---|---|
| gaatgtggcg gcggtagttc caggcgacgg cggacggtgg tacggtcctg gagggcccag | 60 |
| tgcgcgggc tagccgtggc tggagagctt cgaagagcct tgaaatgtga ggaggaggaa | 120 |
| gatagctgtt gcagaagtag tggccaaggc aaaagatggc caaggaaaga tgcctgaaaa | 180 |
| agtcctttca agatagtctt gaagacataa agaagcgaat gaaagagaaa aggaataaaa | 240 |
| acttggcaga gattggcaaa cgcaggtctt ttatagctgc accatgccaa ataatcacca | 300 |
| acacttctac actgctgaaa aattaccaag acaacaacaa aatgttagtt ttagctttgg | 360 |
| aaaatgaaaa atccaaagtg aaagaagccc aagatatcat cctacagctg agaaaagaat | 420 |
| gttactatct cacatgtcag ctatatgcat tgaaaggaaa acttacatca caacaaacag | 480 |
| tagaacctgc tcagaaccag gaaatatgtt cctctggaat ggaccccaat agtgatgaca | 540 |
| gctccagaaa tttatttgtg aaggatttac cgcaaattcc tcttgaagaa actgaacttc | 600 |
| caggacaagg agaatcattt caaatagaag atcagatacc tactattcct caagacacac | 660 |
| tgggagttga ttttgattca ggtgaagcta agtctactga taatgtctta cctagaactg | 720 |
| tatctgttcg tagcagttta aagaaacatt gtaacagtat atgtcagttt gatagcttgg | 780 |
| atgattttga aaccagtcat ttggcaggga gtctttttga attcgaaaga gttggatttt | 840 |
| tagacccact agtaaacatg cacatacctg aaaatgtaca acacaatgct tgtcaatgga | 900 |
| gcaaggacca agttaactta tcaccaaagc tgattcagcc aggaacgttt actaaaacaa | 960 |
| aagaagacat tttagaatct aaatctgaac aaactaaaag taagcaaaga gatacacaag | 1020 |
| aaagaaaaag agaagagaaa agaaaagcta acaggagaaa atcaaaacgt atgtcaaaat | 1080 |
| ataaagagaa taaagcgaa aataaaaaaa ctgttcccca aaaaaaaatg cacaaatctg | 1140 |
| tcagttccaa tgatgcttac aatttttaatt tggaagaggg tgttcatctt actcctttcc | 1200 |
| gacaaaaagt gagcaatgac tctaatagag aagaaaacaa cgagtctgaa gtgagcctct | 1260 |
| gtgaatcaag tggttcagga gatgattccg atgacctcta tttgcccact tgcaagtaca | 1320 |
| ttcagaatcc cacgagcaat tcagatagac cagtcaccag gcctctagct aaaagagcac | 1380 |
| tgaaatacac agatgaaaaa gagacggagg ttctaagcc aacaaaaact cctaccacta | 1440 |
| caccacctga aactcagcag tcacctcatc ttagcctgaa ggatatcacc aatgtctcct | 1500 |

```
tgtatcctgt tgtgaaaatc agaagacttt ctctttctcc aaaaaagaat aaagcaagcc   1560
cagcagtggc tctgcctaaa cgtaggtgca cagccagcgt gaactataag gagcccaccc   1620
tcgcttcgaa actgagaaga ggggacccct ttacagattt gtgtttttg aattctccta    1680 ttttcaagca gaaaaggat ttgagacgtt ctaaaaaaag agccctggag gtatcacctg    1740
ccaaagaagc aatttttatt ttatattatg ttcgagaatt tgtttcgaga ttcccagact   1800
gtaggaaatg taaacttgaa acccacatct gcttgaggta aagtccacgg gcttcacatc   1860
cttagaaaac ttttttagtc catgcattca ctaatgtatg cagacccttta atagattcta  1920 gctttatgtg ttgggggaga gatggagggg tgttgacagt ctgtttcact cagcctacat   1980
acataataaa atctaagccc tttaattaga gatagcaact ttcccagggt gaccgaggaa   2040
tcagtacgtg ttgaacccct cttttaagtt tccttttggt tgtgtcactt ggagattgcc   2100
ttttctttct tgtaagctca gctgtgtcct caaatatatt gcattttacc cagcatttcc   2160
aggtgttttc aggggtcaaa gttttttaagt tatcttagtc tttgatattg tgtaagcgaa   2220
attctccaat cccatctcct agatgatttt tttttaaatc acaaaatgtg attatgctta   2280
acagctgttt cctgtttctc ttaaaataaa atccatttcc tatttctctt aaaataaaat   2340
ccattattct taaaa                                                    2355

<210> SEQ ID NO 19
<211> LENGTH: 1375
<212> TYPE: DNA
<213> ORGANISM: Homo sapiens

<400> SEQUENCE: 19
gtttgaaatc ggaaagttgg cggggctgcg ggagctgagc ctagagtccg gctgttggct     60
agagtgggcg cggatctggt gtggggaagg cggcgggact caggcctgcc tgcgaagcat    120
tgtcctacat aatggtagag gacgaactgg cacttttcga taaaagcata aatgaatttt    180
ggaataaatt caaagtacg gacacctcct gtcagatggc gggactaaga gatacctaca    240
aggattccat caaagcattt gcagaaaagc tgtctgtgaa attaaggaa gaagaacgaa     300 tggttgagat gtttctggaa tatcaaaatc agatcagcag gcaaaataag ctcattcaag    360
aaaaaaagga taacttgtta aaattgattg ctgaagtaaa aggcaaaaag caggaattgg    420
aagtactgac tgcaaatatc caggatctta aggaagaata ttctaggaag aaggaaacta    480
tttctactgc taataaagcg aatgcagaga ggttgaaaag gctgcagaaa tctgcagact    540
tgtataaaga tcgacttgga ctagaaattc gaaaaattta tggtgagaaa ttgcagttta    600
ttttcactaa tattgacccct aagaatcctg agagcccatt tatgttttcc ttacatctca    660
atgaagcaag ggactatgaa gtgtcagata gtgccccctca tcttgagggc ctagcagaat   720
ttcaagagaa tgtaaggaag accaacaatt tttcagcttt tcttgccaat gttcggaaag   780
cttttactgc cacggtttat aattaacata caaatagtgt atataaaaac ggtttatttt   840
tcttctctat tacatatctc ttttttttctt gtttttatta ttattatact ttaagttta   900 gggtacatgt gcacaatgtg caggtttgtt acatatgtat acatgtgcca tattggtgtg   960
ctgcacccat taactcgtca tttcattagg tatatctcct aatgctatcc ctccccctc   1020 ccccaaccca caacagtccc cgttgtgtga tgttcccctt cctgtgtcca tgtgttctca   1080
ttgttcaatt cccacctagg agtgagaata tgtggtgttt ggttttttgt cctttcgata   1140
gtttgctgag aatgatggtt tccagcttca tccatgttcc tacaaaggac atgaactcat   1200 cctttttat ggctgcatag tattccatgg tgtatatgtg ccacattttc ttaatccagt    1260
```

```
ctatcattgt tggacatttg ggttggttcc aagtctttgc tattgtgaat agtgccgaaa    1320
taaacatacg tgtgcatgtg tctttaaaaa aaaaaaaaaa aaaaaaaaaa aaaaa         1375

<210> SEQ ID NO 20
<211> LENGTH: 5753
<212> TYPE: DNA
<213> ORGANISM: Homo sapiens

<400> SEQUENCE: 20
gattggctgg tctgcttcgg gcgggctaaa ggaaggttca agtggagctc tcctaaccga      60
cgcgcgtctg tggagaagcg gcttggtcgg gggtggtctc gtggggtcct gcctgtttag     120
tcgctttcag ggttcttgag ccccttcacg accgtcacca tggaagtgtc accattgcag     180
cctgtaaatg aaaatatgca agtcaacaaa ataaagaaaa atgaagatgc taagaaaaga     240
ctgtctgttg aaagaatcta tcaaaagaaa acacaattgg aacatatttt gctccgccca     300
gacacctaca ttggttctgt ggaattagtg acccagcaaa tgtgggttta cgatgaagat     360
gttggcatta actataggga agtcactttt gttcctggtt tgtacaaaat ctttgatgag     420
attctagtta atgctgcgga caacaaacaa agggacccaa aaatgtcttg tattagagtc     480
acaattgatc cggaaaacaa tttaattagt atatggaata atggaaaagg tattcctgtt     540
gttgaacaca aagttgaaaa gatgtatgtc ccagctctca tatttggaca gctcctaact     600
tctagtaact atgatgatga tgaaaagaaa gtgacaggtg gtcgaaatgg ctatggagcc     660
aaattgtgta acatattcag taccaaattt actgtggaaa cagccagtag agaatacaag     720
aaaatgttca acagacatg gatggataat atgggaagag ctggtgagat ggaactcaag     780
cccttcaatg gagaagatta tacatgtatc acctttcagc ctgatttgtc taagtttaaa     840
atgcaaagcc tggacaaaga tattgttgca ctaatggtca aagagcata tgatattgct     900 ggatccacca aagatgtcaa agtctttctt aatggaaata aactgccagt aaaaggattt     960
cgtagttatg tggacatgta tttgaaggac aagttggatg aaactggtaa ctccttgaaa    1020
gtaatacatg aacaagtaaa ccacaggtgg gaagtgtgtt taactatgag tgaaaaaggc    1080
tttcagcaaa ttagctttgt caacagcatt gctacatcca gggtggcag acatgttgat    1140 tatgtagctg atcagattgt gactaaaactt gttgatgttg tgaagaagaa gaacaagggt    1200
ggtgttgcag taaagcaca tcaggtgaaa aatcacatgt ggatttttgt aaatgcctta    1260
attgaaaacc caacctttga ctctcagaca aaagaaaaca tgactttaca acccaagagc    1320
tttggatcaa catgccaatt gagtgaaaaa tttatcaaag ctgccattgg ctgtggtatt    1380
gtagaaagca tactaaactg ggtgaagttt aaggcccaag tccagttaaa caagaagtgt    1440
tcagctgtaa aacataatag aatcaaggga attcccaaac tcgatgatgc caatgatgca    1500
gggggccgaa actccactga gtgtacgctt atcctgactg agggagattc agccaaaact    1560
ttggctgttt caggccttgg tgtggttggg agagacaaat atgggttttt ccctcttaga    1620
ggaaaaatac tcaatgttcg agaagcttct cataagcaga tcatggaaaa tgctgagatt    1680
aacaatatca tcaagattgt gggtcttcag tacaagaaaa actatgaaga tgaagattca    1740
ttgaagacgc ttcgttatgg gaagataatg attatgacag atcaggacca agatggttcc    1800
cacatcaaag gcttgctgat taattttatc catcacaact ggccctctct tctgcgacat    1860
cgttttctgg aggaatttat cactcccatt gtaaaggtat ctaaaaacaa gcaagaaatg    1920 gcatttaca gccttcctga atttgaagag tggaagagtt ctactccaaa tcataaaaaa    1980
```

-continued

```
tggaaagtca aatattacaa aggtttgggc accagcacat caaaggaagc taaagaatac    2040
tttgcagata tgaaaagaca tcgtatccag ttcaaatatt ctggtcctga agatgatgct    2100
gctatcagcc tggcctttag caaaaaacag atagatgatc gaaaggaatg gttaactaat    2160
ttcatggagg atagaagaca acgaaagtta cttgggcttc ctgaggatta cttgtatgga    2220
caaactacca catatctgac atataatgac ttcatcaaca aggaacttat cttgttctca    2280
aattctgata acgagagatc tatcccttct atggtggatg gtttgaaacc aggtcagaga    2340
aaggttttgt ttacttgctt caaacggaat gacaagcgag aagtaaaggt tgcccaatta    2400
gctggatcag tggctgaaat gtcttcttat catcatggtg agatgtcact aatgatgacc    2460
attatcaatt tggctcagaa ttttgtgggt agcaataatc taaacctctt gcagcccatt    2520
ggtcagtttg gtaccaggct acatggtggc aaggattctg ctagtccacg atacatcttt    2580
acaatgctca gctctttggc tcgattgtta tttccaccaa aagatgatca cacgttgaag    2640
tttttatatg atgacaacca gcgtgttgag cctgaatggt acattcctat tattcccatg    2700
gtgctgataa atggtgctga aggaatcggt actgggtggg cctgcaaaat ccccaacttt    2760
gatgtgcgtg aaattgtaaa taacatcagg cgtttgatgg atggagaaga accttttgcca   2820 atgcttccaa gttacaagaa cttcaagggt actattgaag aactggctcc aaatcaatat    2880
gtgattagtg gtgaagtagc tattcttaat tctacaacca ttgaaatctc agagcttccc    2940
gtcagaacat ggacccagac atacaaagaa caagttctag aacccatgtt gaatggcacc    3000
gagaagacac ctcctctcat aacagactat agggaatacc atacagatac cactgtgaaa    3060
tttgttgtga agatgactga agaaaaactg gcagaggcag agagagttgg actacacaaa    3120
gtcttcaaac tccaaactag tctcacatgc aactctatgg tgcttttttga ccacgtaggc   3180 tgtttaaaga aatatgacac ggtgttggat attctaagag actttttttga actcagactt    3240 aaatattatg gattaagaaa agaatggctc ctaggaatgc ttggtgctga atctgctaaa    3300
ctgaataatc aggctcgctt tatcttagag aaaatagatg gcaaaataat cattgaaaat    3360
aagcctaaga aagaattaat taaagttctg attcagaggg gatatgattc ggatcctgtg    3420
aaggcctgga agaagcccca gcaaaaggtt ccagatgaag aagaaaatga agagagtgac    3480
aacgaaaagg aaactgaaaa gagtgactcc gtaacagatt ctggaccaac cttcaactat    3540
cttcttgata tgcccccttg gtatttaacc aaggaaaaga aagatgaact ctgcaggcta    3600
agaaatgaaa aagaacaaga gctggacaca ttaaaaagaa agagtccatc agatttgtgg    3660
aaagaagact tggctacatt tattgaagaa ttggaggctg ttgaagccaa ggaaaaacaa    3720
gatgaacaag tcggacttcc tgggaagggg gggaaggcca aggggaaaaa aacacaaatg    3780
gctgaagttt tgccttctcc gcgtggtcaa agagtcattc cacgaataac catagaaatg    3840
aaagcagagg cagaaaagaa aaataaaaag aaaattaaga atgaaaatac tgaaggaagc    3900
cctcaagaag atggtgtgga actagaaggc ctaaaacaaa gattagaaaa gaaacagaaa    3960
agagaaccag gtacaaagac aaagaaacaa actacattgg catttaagcc aatcaaaaaa    4020
ggaaagaaga gaaatccctg gtctgattca gaatcagata ggagcagtga cgaaagtaat    4080
tttgatgtcc ctccacgaga aacagagcca cggagagcag caacaaaaac aaaattcaca    4140
atggatttgg attcagatga agatttctca gattttgatg aaaaaactga tgatgaagat    4200
tttgtcccat cagatgctag tccacctaag accaaaactt ccccaaaact tagtaacaaa    4260
gaactgaaac cacagaaaag tgtcgtgtca gaccttgaag ctgatgatgt taagggcagt    4320
gtaccactgt cttcaagccc tcctgctaca catttcccag atgaaactga aattacaaac    4380
```

```
ccagttccta aaaagaatgt gacagtgaag aagacagcag caaaaagtca gtcttccacc   4440
tccactaccg gtgccaaaaa aagggctgcc ccaaaaggaa ctaaaaggga tccagctttg   4500
aattctggtg tctctcaaaa gcctgatcct gccaaaacca agaatcgccg caaaaggaag   4560
ccatccactt ctgatgattc tgactctaat tttgagaaaa ttgtttcgaa agcagtcaca   4620
agcaagaaat ccaaggggga gagtgatgac ttccatatgg actttgactc agctgtggct   4680
cctcgggcaa aatctgtacg ggcaaagaaa cctataaagt acctggaaga gtcagatgaa   4740
gatgatctgt tttaaaatgt gaggcgatta ttttaagtaa ttatcttacc aagcccaaga   4800
ctggttttaa agttacctga agctcttaac ttcctcccct ctgaatttag tttggggaag   4860 gtgttttttag tacaagacat caaagtgaag taaagcccaa gtgttcttta gcttttata   4920 atactgtcta aatagtgacc atctcatggg cattgttttc ttctctgctt tgtctgtgtt   4980
ttgagtctgc tttcttttgt ctttaaaacc tgattttaa gttcttctga actgtagaaa   5040
tagctatctg atcacttcag cgtaaagcag tgtgtttatt aaccatccac taagctaaaa   5100
ctagagcagt ttgatttaaa agtgtcactc ttcctccttt tctactttca gtagatatga   5160
gatagagcat aattatctgt tttatcttag ttttatacat aatttaccat cagatagaac   5220
tttatggttc tagtacagat actctactac actcagcctc ttatgtgcca agttttctt   5280 taagcaatga gaaattgctc atgttcttca tcttctcaaa tcatcagagg ccgaagaaaa   5340
acactttggc tgtgtctata acttgacaca gtcaatagaa tgaagaaaat tagagtagtt   5400
atgtgattat ttcagctctt gacctgtccc ctctggctgc ctctgagtct gaatctccca   5460
aagagagaaa ccaattcta agaggactgg attgcagaag actcggggac aacatttgat   5520
ccaagatctt aaatgttata ttgataacca tgctcagcaa tgagctatta gattcatttt   5580
gggaaatctc cataatttca atttgtaaac tttgttaaga cctgtctaca ttgttatatg   5640
tgtgtgactt gagtaatgtt atcaacgttt ttgtaaatat ttactatgtt tttctattag   5700
ctaaattcca acaattttgt actttaataa aatgttctaa acattgcaac cca           5753

<210> SEQ ID NO 21
<211> LENGTH: 3010
<212> TYPE: DNA
<213> ORGANISM: Homo sapiens

<400> SEQUENCE: 21
agcattgacc aataggagac cgtagtgata gcgacgggga aattcaaacg tgtttgcgga     60
aaggagtttg ggttccatct tttcatttcc ccagcgcagc tttctgtaga aatggaatcc    120
gaggatttaa gtggcagaga attgacaatt gattccataa tgaacaaagt gagagacatt    180
aaaaataagt ttaaaaatga agaccttact gatgaactaa gcttgaataa aatttctgct    240
gatactacag ataactcggg aactgttaac caaattatga tgatggcaaa caacccagag    300
gactggttga gtttgttgct caaactagag aaaaacagtg ttccgctaag tgatgctctt    360
ttaaataaat tgattggtcg ttacagtcaa gcaattgaag cgcttccccc agataaatat    420
ggccaaaatg agagttttgc tagaattcaa gtgagatttg ctgaattaaa agctattcaa    480
gagccagatg atgcacgtga ctactttcaa atggccagag caaactgcaa gaatttgct    540 tttgttcata tatcttttgc acaatttgaa ctgtcacaag gtaatgtcaa aaaaagtaaa    600
caacttcttc aaaaagctgt agaacgtgga gcagtaccac tagaaatgct ggaaattgcc    660
ctgcggaatt taaacctcca aaaaagcag ctgctttcag aggaggaaaa gaagaattta    720
```

```
tcagcatcta cggtattaac tgcccaagaa tcattttccg gttcacttgg gcatttacag    780
aataggaaca acagttgtga ttccagagga cagactacta aagccaggtt tttatatgga    840
gagaacatgc caccacaaga tgcagaaata ggttaccgga attcattgag acaaactaac    900
aaaactaaac agtcatgccc atttggaaga gtcccagtta accttctaaa tagcccagat    960
tgtgatgtga agacagatga ttcagttgta ccttgtttta tgaaaagaca aacctctaga    1020
tcagaatgcc gagatttggt tgtgcctgga tctaaaccaa gtggaaatga ttcctgtgaa    1080
ttaagaaatt taaagtctgt tcaaaatagt catttcaagg aacctctggt gtcagatgaa    1140
aagagttctg aacttattat tactgattca ataaccctga agaataaaac ggaatcaagt    1200
cttctagcta aattagaaga aactaaagag tatcaagaac cagaggttcc agagagtaac    1260
cagaaacagt ggcaatctaa gagaaagtca gagtgtatta accagaatcc tgctgcatct    1320
tcaaatcact ggcagattcc ggagttagcc cgaaaagtta atacagagca gaaacatacc    1380
acttttgagc aacctgtctt ttcagtttca aaacagtcac caccaatatc aacatctaaa    1440
tggtttgacc caaaatctat ttgtaagaca ccaagcagca ataccttgga tgattacatg    1500
agctgtttta gaactccagt tgtaaagaat gactttccac ctgcttgtca gttgtcaaca    1560
ccttatggcc aacctgcctg tttccagcag caacagcatc aaatacttgc cactccactt    1620
caaaatttac aggttttagc atcttcttca gcaaatgaat gcatttcggt taaggaaga    1680 atttattcca tattaaagca gataggaagt ggaggttcaa gcaaggtatt tcaggtgtta    1740
aatgaaaaga acagatata tgctataaaa tatgtgaact tagaagaagc agataaccaa    1800
actcttgata gttaccggaa cgaaatagct tatttgaata aactacaaca acacagtgat    1860
aagatcatcc gactttatga ttatgaaatc acggaccagt acatctacat ggtaatggag    1920
tgtgaaaata ttgatcttaa tagttggctt aaaaagaaaa aatccattga tccatgggaa    1980
cgcaagagtt actggaaaaa tatgttagag gcagttcaca caatccatca acatggcatt    2040
gttcacagtg atcttaaacc agctaacttt ctgatagttg atggaatgct aaagctaatt    2100
gattttggga ttgcaaacca atgcaaccca gatacaacaa gtgttgttaa agattctcag    2160
gttggcacag ttaattatat gccaccagaa gcaatcaaag atatgtcttc ctccagagag    2220
aatgggaaat ctaagtcaaa gataagcccc aaaagtgatg tttggtcctt aggatgtatt    2280
ttgtactata tgacttacgg gaaaacacca tttcagcaga taattaatca gatttctaaa    2340
ttacatgcca taattgatcc taatcatgaa attgaatttc ccgatattcc agagaaagat    2400
cttcaagatg tgttaaagtg ttgtttaaaa agggacccaa aacagaggat atccattcct    2460
gagctcctgg ctcatccata tgttcaaatt caaactcatc cagttaacca aatggccaag    2520
ggaaccactg aagaaatgaa atatgttctg ggccaacttg ttggtctgaa ttctcctaac    2580
tccattttga agctgctaa aactttatat gaacactata gtggtggtga aagtcataat    2640
tcttcatcct ccaagacttt tgaaaaaaaa aggggaaaaa aatgatttgc agttattcgt    2700
aatgtcagat accacctata aaatatattg gactgttata ctcttgaatc cctgtggaaa    2760
tctacatttg aagacaacat cactctgaag tgttatcagc aaaaaaaatt cagtagatta    2820
tctttaaaag aaaactgtaa aaatagcaac cacttatggc actgtatata ttgtagactt    2880
gttttctctg ttttatgctc ttgtgtaatc tacttgacat cattttactc ttggaatagt    2940
gggtggatag caagtatatt ctaaaaaact ttgtaaataa agttttgtgg ctaaaatgac    3000
actaacattt                                                           3010
```

-continued

```
<210> SEQ ID NO 22
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward primer sequence of CENPA

<400> SEQUENCE: 22
tattggccct acaagaggca gcag                                          24

<210> SEQ ID NO 23
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse primer sequence of CENPA

<400> SEQUENCE: 23
gccagttgca catcctttgg gaag                                          24

<210> SEQ ID NO 24
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward primer sequence of E2F8

<400> SEQUENCE: 24
acgaagtggc agaggaactt aatg                                          24

<210> SEQ ID NO 25
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse primer sequence of E2F8

<400> SEQUENCE: 25
aggcggctca ccatatgtaa actc                                          24

<210> SEQ ID NO 26
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward primer sequence of MKI67

<400> SEQUENCE: 26
agcacctgct tgtttggaag gg                                            22

<210> SEQ ID NO 27
<211> LENGTH: 23
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<223> OTHER INFORMATION: Reverse primer sequence of MKI67

<400> SEQUENCE: 27
acacaacagg aagctggata cgg                                                 23

<210> SEQ ID NO 28
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward primer sequence of NEK2

<400> SEQUENCE: 28
agatccggag gaagagtgat gg                                                  22

<210> SEQ ID NO 29
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse primer sequence of NEK2

<400> SEQUENCE: 29
tgtttctcag cttctgtcat ggag                                                24

<210> SEQ ID NO 30
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward primer sequence of AURKB

<400> SEQUENCE: 30
tgagagtgca tcacacaacg agac                                                24

<210> SEQ ID NO 31
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse primer sequence of AURKB

<400> SEQUENCE: 31
gggaacttta ggtccacctt gacg                                                24

<210> SEQ ID NO 32
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

```
<223> OTHER INFORMATION: Forward primer sequence of GAPDH

<400> SEQUENCE: 32
gagtcaacgg atttggtcgt                                              20

<210> SEQ ID NO 33
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse primer sequence of GAPDH

<400> SEQUENCE: 33
gacaagcttc ccgttctcag                                              20

<210> SEQ ID NO 34
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward primer sequence of EREG

<400> SEQUENCE: 34
aggaggatgg agatgctctg tg                                           22

<210> SEQ ID NO 35
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse primer sequence of EREG

<400> SEQUENCE: 35
actgcctgta gaagatggaa accc                                         24

<210> SEQ ID NO 36
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward primer sequence of CXCL2

<400> SEQUENCE: 36
cccaaaccga agtcatagcc acac                                         24

<210> SEQ ID NO 37
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse primer sequence of CXCL2

<400> SEQUENCE: 37
gccaccaata agcttcctcc ttcc                                         24
```